(12) United States Patent
Reglos et al.

(10) Patent No.: US 8,206,293 B2
(45) Date of Patent: Jun. 26, 2012

(54) RETRACTOR

(75) Inventors: Joey Camia Reglos, Lake Forest, CA (US); Moti Altarac, Irvine, CA (US); Stanley Kyle Hayes, Mission Viejo, CA (US); Jean A. Harnapp, Irvine, CA (US)

(73) Assignee: Exactech, Inc., Gainesville, FL (US)

( * ) Notice: Subject to any disclaimer, the term of this patent is extended or adjusted under 35 U.S.C. 154(b) by 1025 days.

(21) Appl. No.: 12/080,388

(22) Filed: Mar. 31, 2008

(65) Prior Publication Data

US 2008/0249372 A1 Oct. 9, 2008

Related U.S. Application Data

(60) Provisional application No. 60/921,128, filed on Mar. 30, 2007, provisional application No. 60/937,732, filed on Jun. 29, 2007.

(51) Int. Cl.
*A61B 1/32* (2006.01)

(52) U.S. Cl. ......... 600/210; 600/201; 600/214; 600/215

(58) Field of Classification Search ................. 600/201, 600/205, 210–212, 214–216, 219, 224, 225, 600/245

See application file for complete search history.

(56) References Cited

U.S. PATENT DOCUMENTS

| | | | |
|---|---|---|---|
| 5,363,841 A | 11/1994 | Coker | |
| 5,688,223 A | 11/1997 | Rosendahl | |
| 5,902,233 A | 5/1999 | Farley et al. | |
| 5,984,867 A | 11/1999 | Deckman et al. | |
| 6,074,343 A | 6/2000 | Nathanson et al. | |
| 6,139,493 A * | 10/2000 | Koros et al. | 600/215 |
| 7,210,485 B2 | 5/2007 | Zinkel | |
| 7,261,688 B2 | 8/2007 | Smith et al. | |
| 7,537,565 B2 | 5/2009 | Bass | |
| 7,691,057 B2 | 4/2010 | Miles et al. | |
| 2006/0224044 A1 * | 10/2006 | Marchek et al. | 600/233 |
| 2007/0073111 A1 * | 3/2007 | Bass | 600/215 |

FOREIGN PATENT DOCUMENTS

WO 2008121421 10/2008

OTHER PUBLICATIONS

International Search Report and Written Opinion for application No. PCT/US08/04253, Mail Date: Jul. 28, 2008. 3 pages.

* cited by examiner

*Primary Examiner* — Thomas C. Barrett
*Assistant Examiner* — Christine Nelson
(74) *Attorney, Agent, or Firm* — Meyertons, Hood, Kivlin, Kowert & Goetzel, P.C.; Eric B. Meyertons

(57) ABSTRACT

The retractor system for use in spinal surgery and other types of surgical procedures that is a simple and efficient solution for minimally invasive access to thoracolumbar spine is disclosed. The fully customizable design allows the surgeon to independently angle the retractor blades and expand the retractor in both cephalad-caudal and medial-lateral directions. With an offering of a range of blade lengths, access can be tailored to the patient's anatomy. Auxiliary instruments such as the retractor inserter, universal hex driver and blade removal instrument allow quick and controlled access to the surgical site. The retractor system provides versatility and control ensuring minimal tissue trauma.

16 Claims, 53 Drawing Sheets

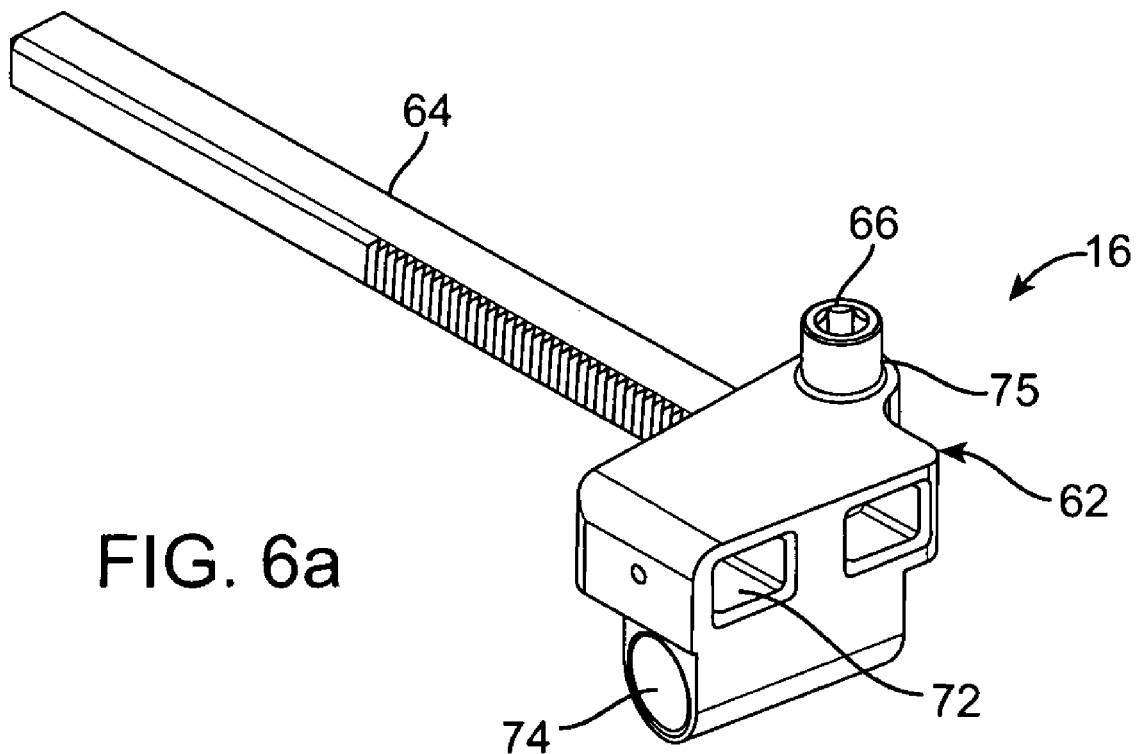

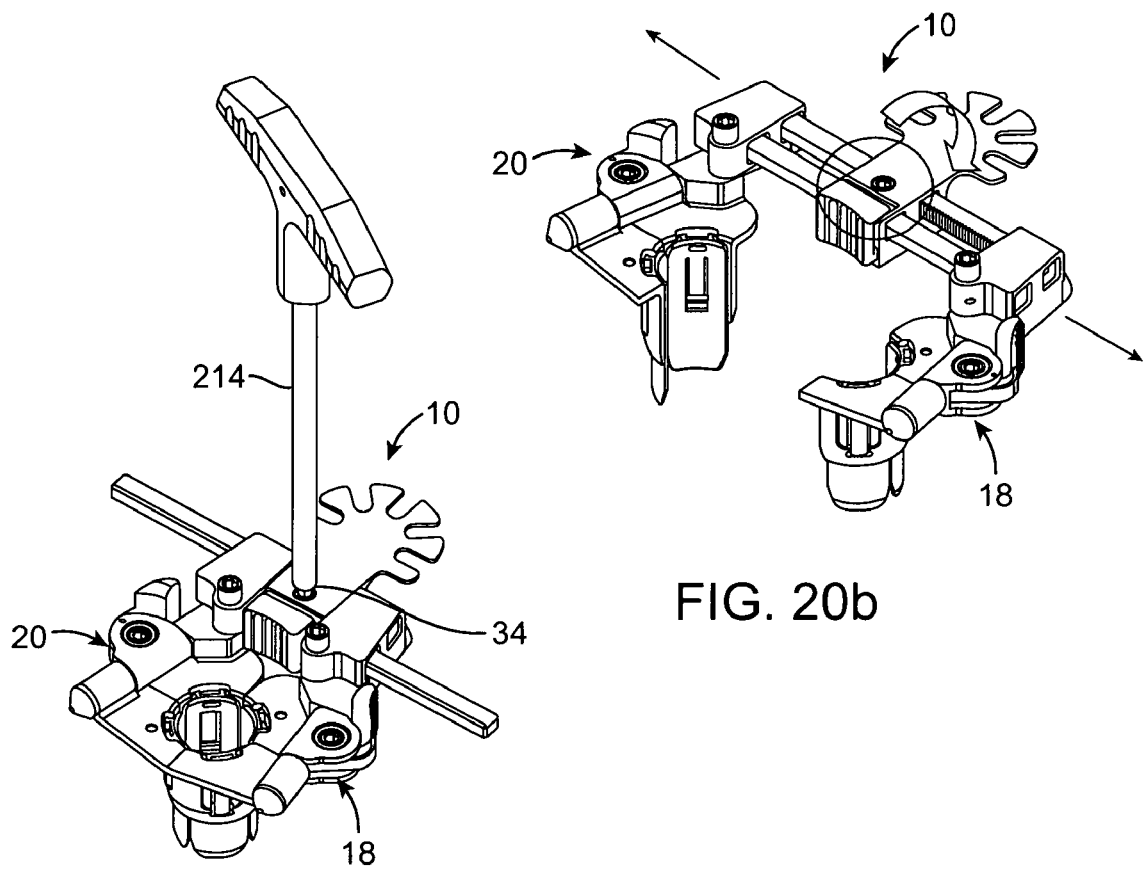
FIG. 20b
FIG. 20a
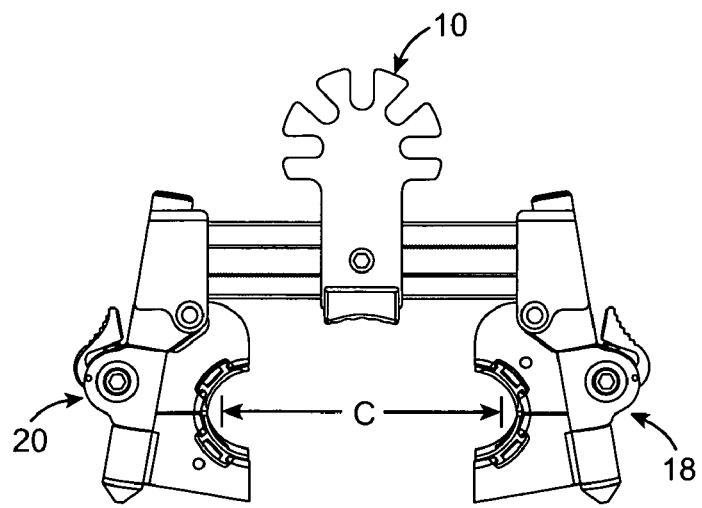
FIG. 20c

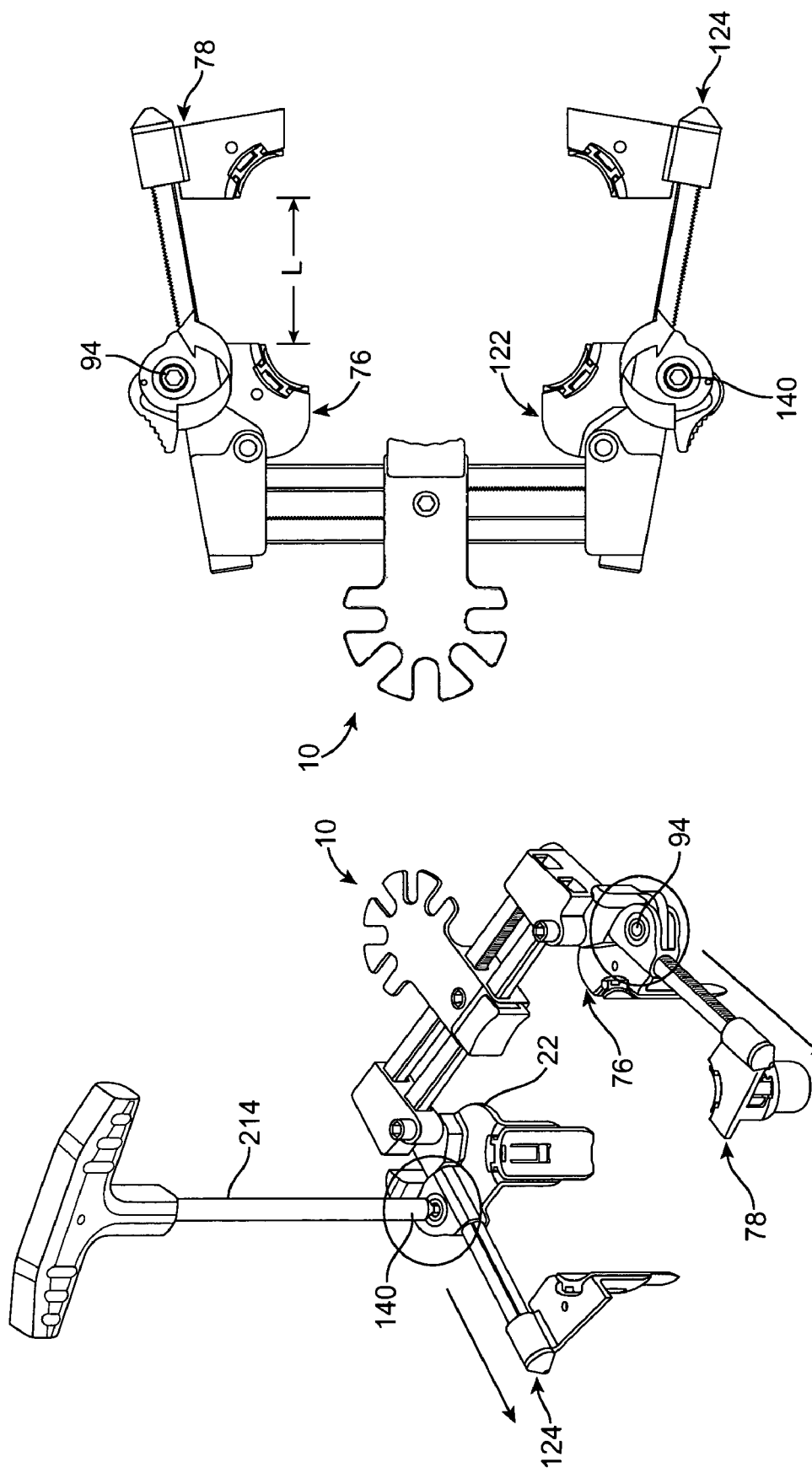

| Maximum Spans ||
| --- | --- |
| Blade Length (mm) | Distal Span* (mm) |
| 30 | 110 |
| 40 | 120 |
| 50 | 130 |
| 60 | 140 |
| 70 | 150 |
| 80 | 160 |
| 90 | 170 |

FIG. 23

SECTION A-A

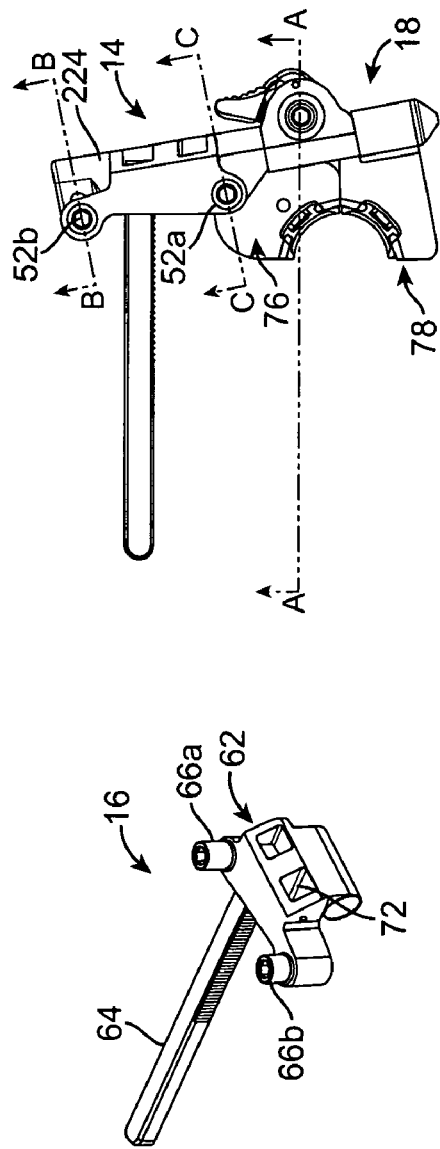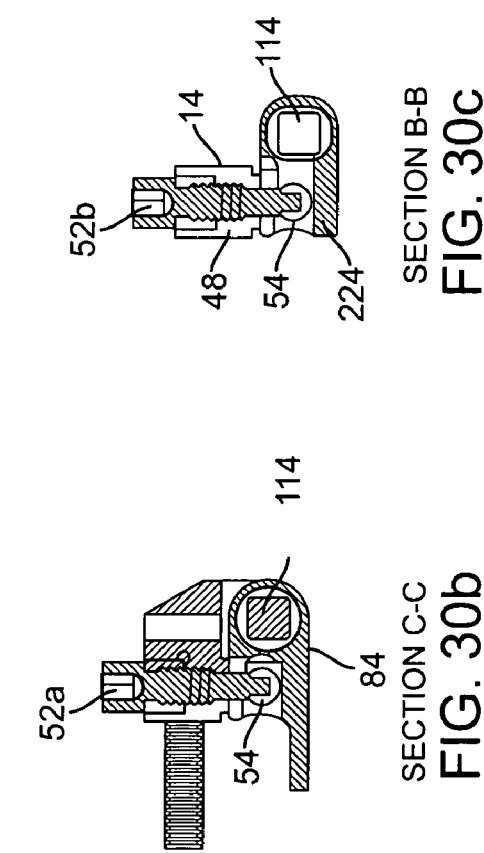

SECTION C-C

SECTION D-D

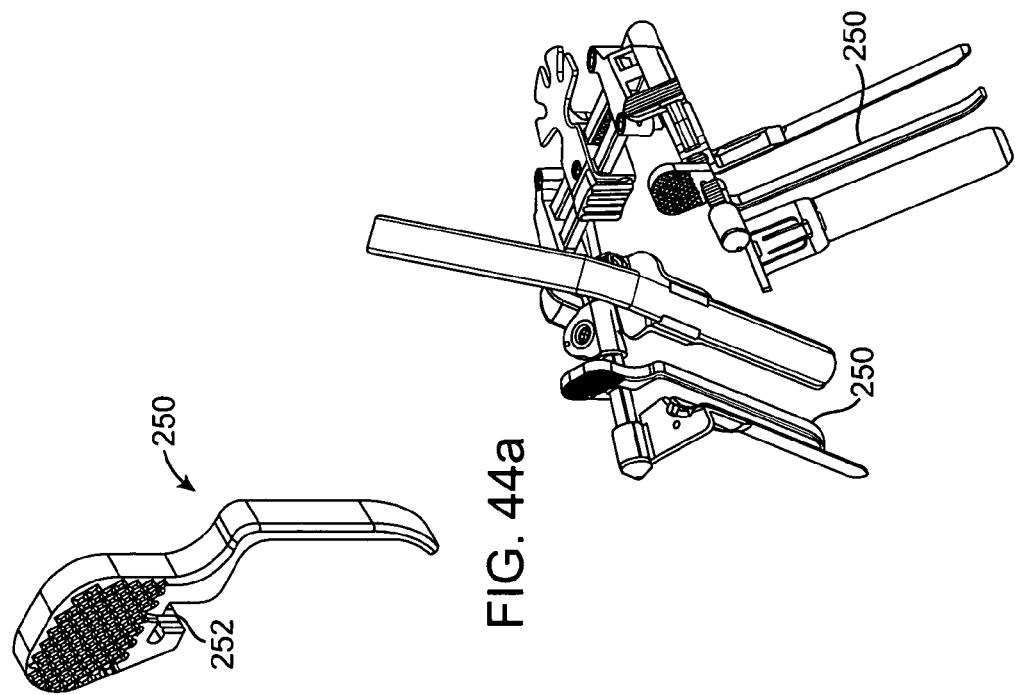
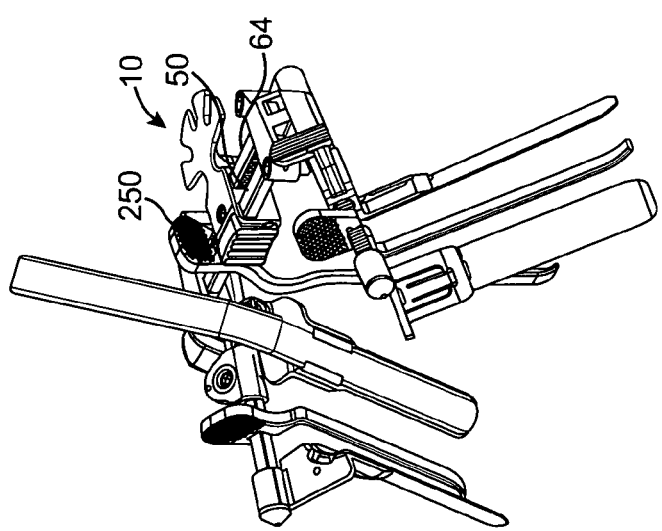
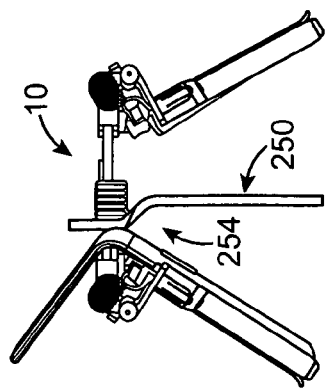
FIG. 44a
FIG. 44b
FIG. 44c
FIG. 44d

RETRACTOR

CROSS-REFERENCE TO RELATED APPLICATIONS

This application claims priority to and is a continuation-in-part of U.S. Provisional Patent Application Ser. No. 60/921,128 entitled "Retractor" filed on Mar. 30, 2007, hereby incorporated by reference in its entirety. This application also claims priority to and is a continuation-in-part of U.S. Provisional Patent Application Ser. No. 60/937,732 entitled "Retractor" filed on Jun. 29, 2007, hereby incorporated by reference in its entirety.

FIELD

The present invention generally relates to surgical instruments and methods. More particularly, but not exclusively, the present invention relates to surgical retractors for use in spinal surgery and other types of surgical procedures.

BACKGROUND

Surgical procedures often require the creation of a surgical exposure to clear the field for the surgeon and to provide access to the desired area. The surgical exposure is usually started with an incision of a suitable depth. Surgical instruments known as retractors are then inserted into the incision and used to pull back skin, muscle and other soft tissue to permit access to the region of interest, reach deeper regions of the body, protect adjacent tissues and provide the surgeon with clear visibility of the area of the surgical field.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades can be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

The retractors in use today retract the opening created in the body of the patient in a uniform manner. If the surgeon needs a large opening near the spine, for instance, the opening in the body of the patient is typically retracted in a uniform manner. In an "open" spinal surgical procedure, large bands of muscles in the back are stripped free from the spine and retracted off to each side. This allows for excellent visualization of the spine and easy access for the surgeon. The downside of "open" surgery is that there can be considerable back pain from the muscle retraction. Also, the muscles develop some degree of permanent scar formation and damage as a result of the necessary retraction. This creates significant trauma for the patient and increases the patient's recovery time.

What is needed is a surgical retractor customized for spinal surgery that gives a surgeon a suitable area within the body to work on the patient while reducing the required incision size. This reduces trauma to the patient and reduces the patient's recovery time.

SUMMARY

According to one aspect of the invention, a surgical retractor is disclosed. The retractor includes a main body and a main body plane. Connected to the right side of the main body is a right track assembly that is configured to be movable inwardly and outwardly with respect to the main body. A left track assembly is connected to the left side of the main body and is configured to be movable inwardly and outwardly with respect to the main body. The retractor further includes a right blade assembly comprising a right upper blade assembly connected to a right lower blade assembly. The right blade assembly is connected to the right track assembly such that right blade assembly moves with the right track assembly. The right upper blade assembly includes a first blade support and a first removable blade connected to the first blade support such that the first blade extends perpendicularly to the main body plane. The right lower blade assembly includes a second blade support and a second removable blade connected to the second blade support such that the second blade extends perpendicularly to the main body plane. The retractor further includes a left blade assembly comprising a left upper blade assembly connected to a left lower blade assembly. The left blade assembly is connected to the left track assembly such that the left blade assembly moves with the left track assembly. The left upper blade assembly includes a third blade support and a third removable blade connected to the third blade support such that the third blade extends perpendicularly to the main body plane. The left lower blade assembly includes a fourth blade support and a fourth removable blade connected to the fourth blade support such that the fourth blade extends perpendicularly to the main body plane. The right upper blade assembly includes a right mounting arm having a longitudinal axis. The right lower blade assembly is movable inwardly and outwardly with respect to the right upper blade along the longitudinal axis of the right mounting arm. The left upper blade assembly includes a left mounting arm having a longitudinal axis. The left lower blade assembly is movable inwardly and outwardly with respect to the left upper blade along the longitudinal axis of the left mounting arm.

According to another aspect of the present invention, a surgical retractor is disclosed. The retractor includes a main body having a longitudinal axis, a transverse axis and a main body plane. The retractor further includes a right assembly comprising a right upper blade and right lower blade. The right upper and lower blades extend generally perpendicular to the main body plane. The right assembly slides longitudinally with respect to the main body carrying the right upper and right lower blades. The right lower blade slides with respect to the right upper blade along a right mounting arm longitudinal axis. The retractor further includes a left assembly comprising a left upper blade and left lower blade. The left upper and lower blades extend generally perpendicular to the main body plane. The left assembly slides longitudinally with respect to the main body carrying the left upper and left lower blades. The left lower blade slides with respect to the left upper blade along a left mounting arm longitudinal axis. The right mounting arm longitudinal axis is angled with respect to the main body longitudinal axis and the left mounting arm longitudinal axis is angled with respect to the main body longitudinal axis.

Other advantages will be apparent from the description that follows, including the drawings and claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. All figures herein illustrate surgical retractors according to the present invention.

FIG. 6a illustrates a perspective view of an upper left rack assembly according to the present invention.

FIG. 20a illustrates a perspective view of a T-shaped driver connected to the middle pinion of the retractor according to the present invention.

FIG. 20b illustrates a perspective view of the left and right assemblies of the retractor expanded apart according to the present invention FIG. 20c illustrates a top view of the left and right assemblies of the retractor expanded apart according to the present invention.

FIG. 21a illustrates a perspective view of a T-shaped driver connected to a pinion of an upper left blade support assembly with the lower right and lower left blade supports expanded apart from the upper right and upper left blade supports, respectively, according to the present invention.

FIG. 21b illustrates a top view of a retractor with the lower right and lower left blade supports expanded apart from the upper right and upper left blade supports, respectively, by a distance L according to the present invention.

FIG. 23 is a table of maximum distal spans for various blade lengths according to the present invention.

FIG. 29 illustrates the upper left rack assembly of the retractor according to the present invention.

FIGS. 30a-30c illustrate the various views of the upper right track assembly connected to the right assembly of the retractor according to the present invention.

FIG. 30d illustrates a first end piece of the retractor according to the present invention.

FIGS. 34a-34c illustrate the upper left blade support assembly of the retractor according to the present invention.

FIG. 44a illustrates a medial blade of the retractor according to the present invention.

FIG. 44b illustrates two medial blades and one illuminator connected to the retractor according to the present invention.

FIGS. 44c-44d illustrate three medial blades and one illuminator connected to the retractor according to the present invention.

DETAILED DESCRIPTION

Figure 1A:
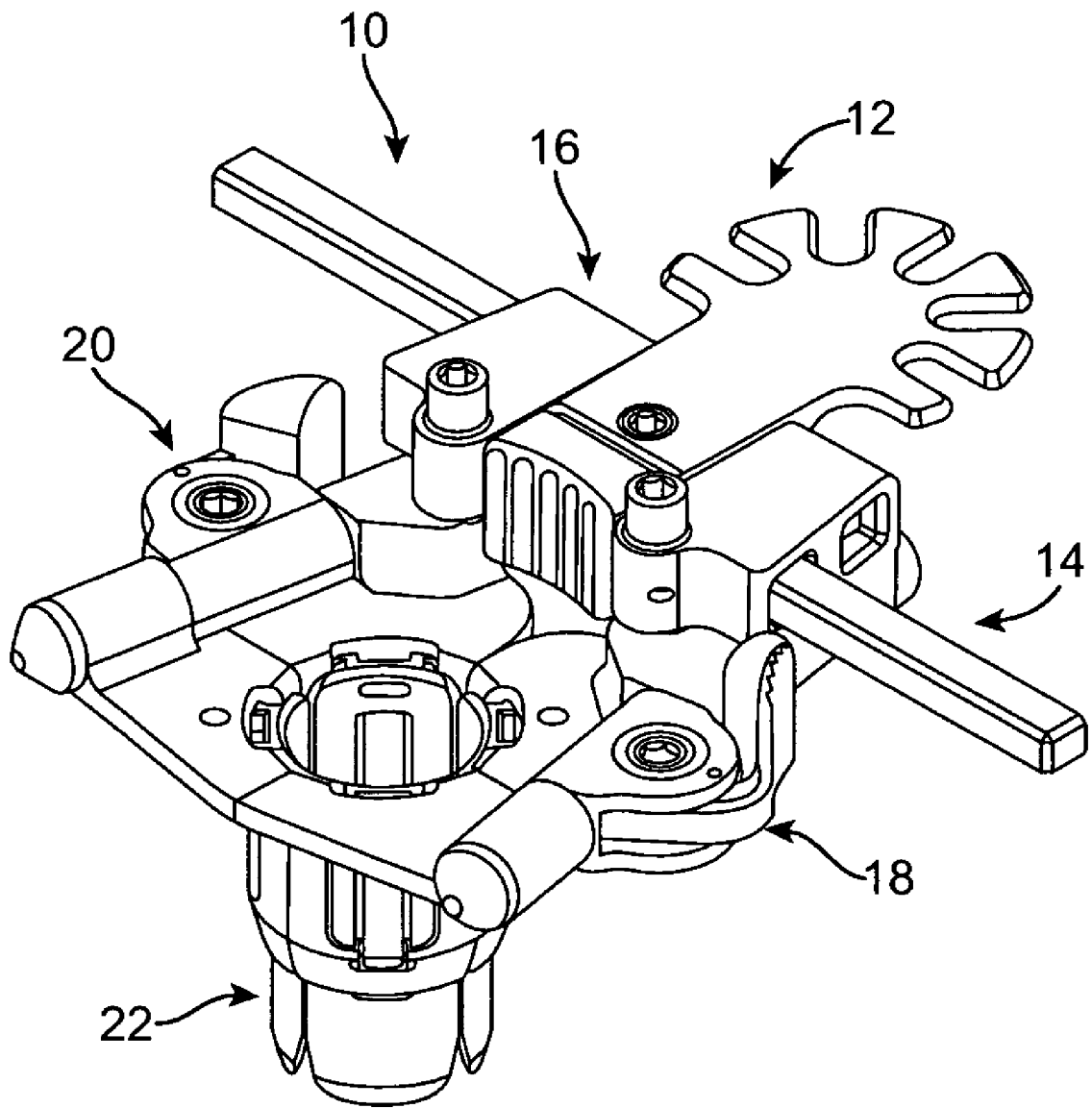
FIG. 1a illustrates a perspective view of the retractor according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of surgical retractors.

In use, the whole retractor assembly shown in the figures is introduced into the surgical field. Upon introduction, the initial configuration of the retractor is in a closed position such that the retractor blades extend downwardly and all of the distal ends of each blade are in close proximity to one another to allow ease of introduction. Once inserted at the desired location, the retractor forms a small field of visibility. The surgeon then causes the blades to be expanded outwardly by operating the various constructs shown in the figures to customize the degree and directions of retraction. One or more of the blades rotate outwardly and/or translate along multi-axial directions. Once in position, the blades are then locked to achieve a custom retraction according to surgeon preference and patient anatomy. The expanded blades act to spread the muscle and tissue further to provide retraction beyond the ring of view formed when the retractor is first inserted. The retractor of the present invention is customized for the demands of spinal surgery and reduces the "creep" of muscle or other tissue into the surgical field leaving a larger and more secure surgical area to be exposed for surgical access, increased visibility and stability.

The entire device may be constructed of surgical steel, or alternatively, various components of the device may be constructed of one or more materials selected from the group consisting of stainless steel, titanium and plastics.

With reference to the figures the retractor will now be described in detail. Various views of a retractor 10 according to the present invention are shown in FIGS. 1a through 1e. The retractor 10 includes a middle assembly 12, an upper right rack assembly 14, an upper left rack assembly 16, a right assembly 18, a left assembly 20 and blades 22. The upper right and left rack assemblies 14, 16 are connected to the middle assembly 12. Blades 22 are connected to the right and left assemblies 18, 20. The right and left assemblies 18, 20 are connected to the upper right and left rack assemblies 14, 16, respectively.

Figure 2A:
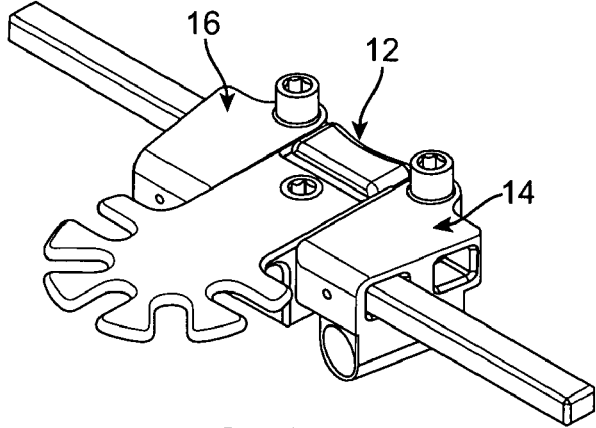
FIG. 2a illustrates a rear perspective view of the middle assembly connected to the upper right rack and upper left rack assemblies according to the present invention.
Figure 2B:
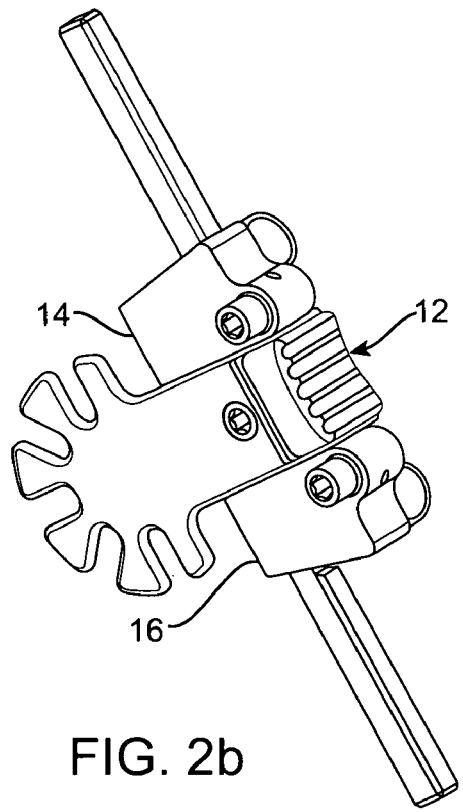
FIG. 2b illustrates a front perspective view of the middle assembly connected to the upper right rack and upper left rack assemblies according to the present invention.
Figure 2C:
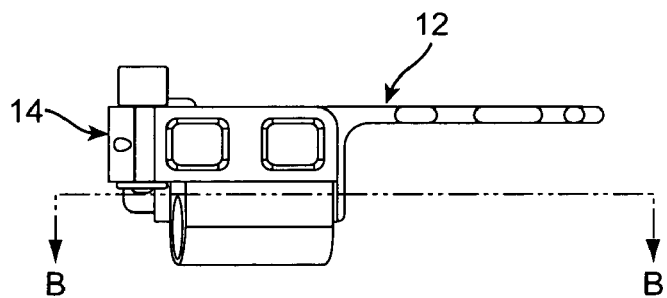
FIG. 2c illustrates a side view of the middle assembly connected to the upper right rack and upper left rack assemblies according to the present invention.

Turning now to FIG. 2a, there is shown the middle assembly 12 connected to the upper right rack assembly 14 and upper left rack assembly 16 of the retractor 10 according to the present invention. The middle assembly 12 includes a main body assembly 24 and a main body sub-assembly 26.

Figure 1B:
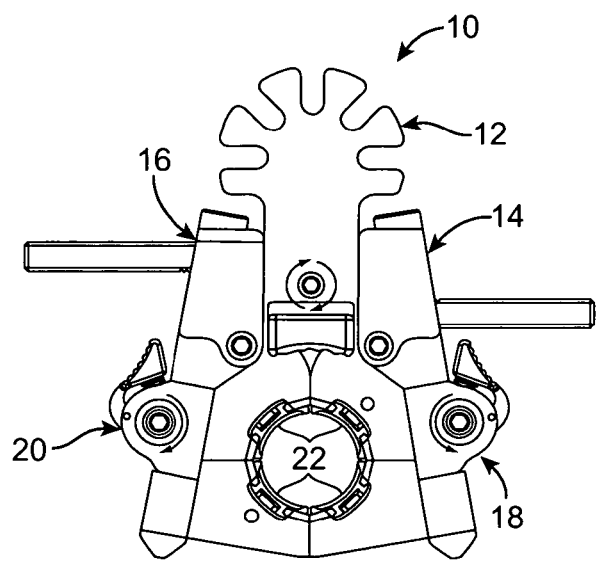
FIG. 1b illustrates a top view of the retractor according to the present invention.
Figure 1C:
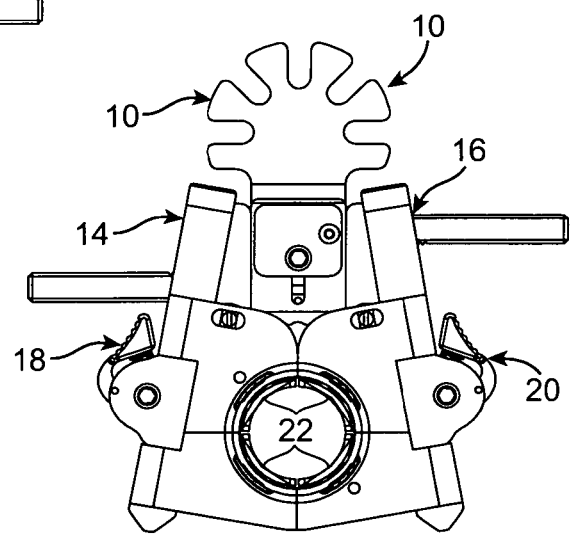
FIG. 1c illustrates a bottom view of the retractor according to the present invention.
Figure 1D:
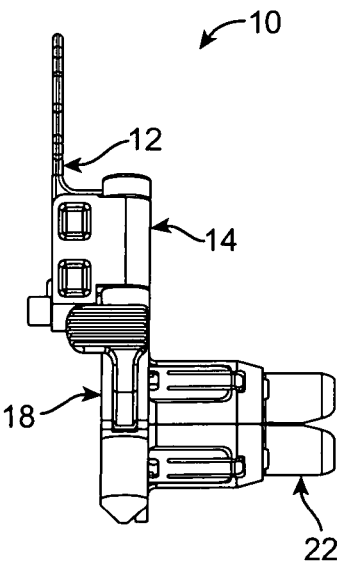
FIG. 1d illustrates a side view of the retractor according to the present invention.
Figure 1E:
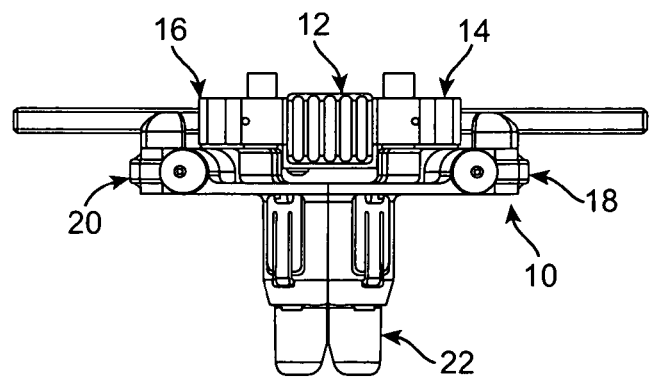
FIG. 1e illustrates an end view of the retractor according to the present invention.
Figure 3B:
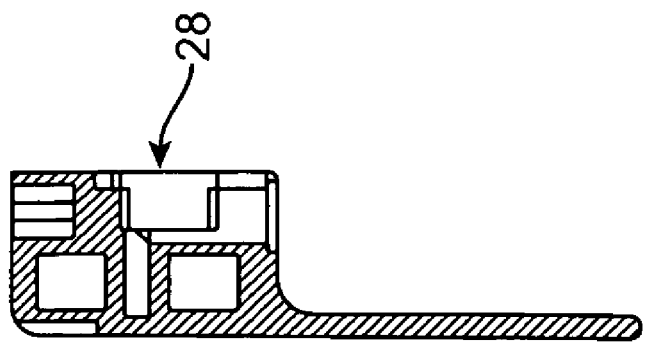
FIG. 3b illustrates a side cross-sectional view of the main body of the middle assembly according to the present invention.
Figure 3A:
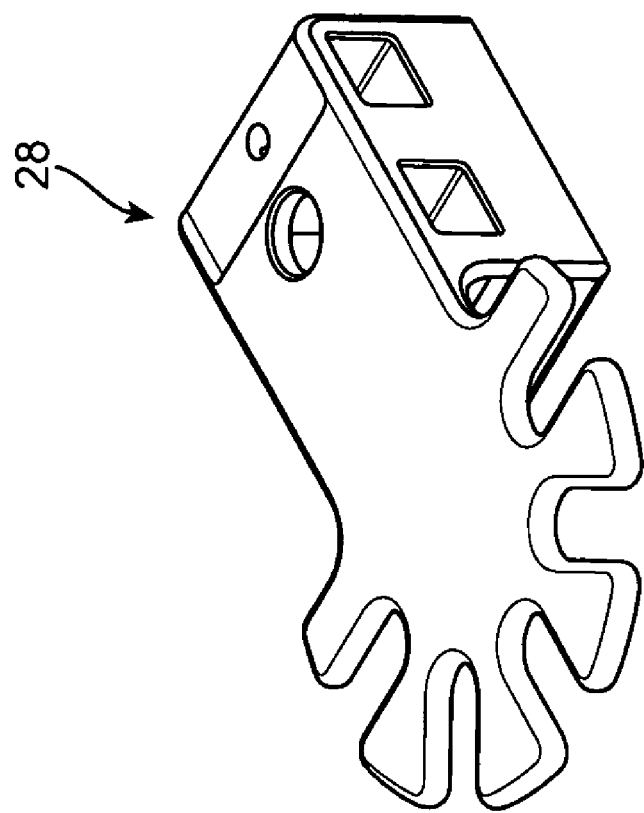
FIG. 3a illustrates a perspective view of the main body of the middle assembly according to the present invention.
Figure 3C:
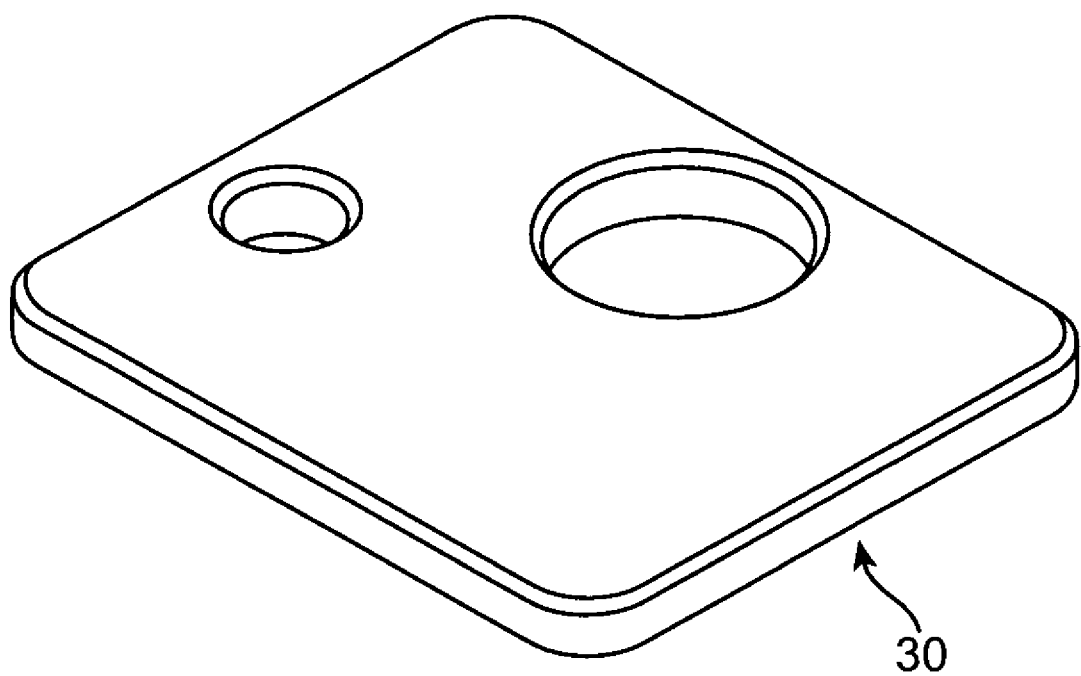
FIG. 3c illustrates a perspective view of the cover of the main body of the middle assembly according to the present invention.
Figure 3D:
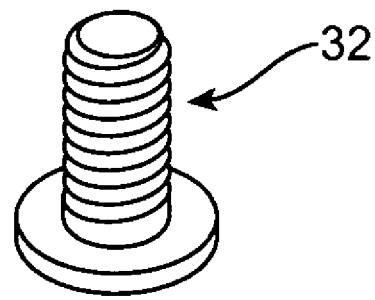
FIG. 3d illustrates a perspective view of a fastener of the main body of the middle assembly according to the present invention.

Referring now to FIGS. 3a, 3b, 3c, and 3d, the main body assembly 24 includes a main body 28 (shown in FIGS. 3a and 3b) and cover 30 (shown in FIG. 3c) with fastener 32 (shown in FIG. 3d). The main body assembly 24 houses the main body sub-assembly 26 as shown in FIG. 2a. The main body includes a main body plane which is coincident with the plane of the paper in which FIG. 1b and FIG. 1c are drawn. In FIGS. 1d and 1e, the main body plane is perpendicular to the plane of the paper on which these figures are drawn.

Figure 4A:
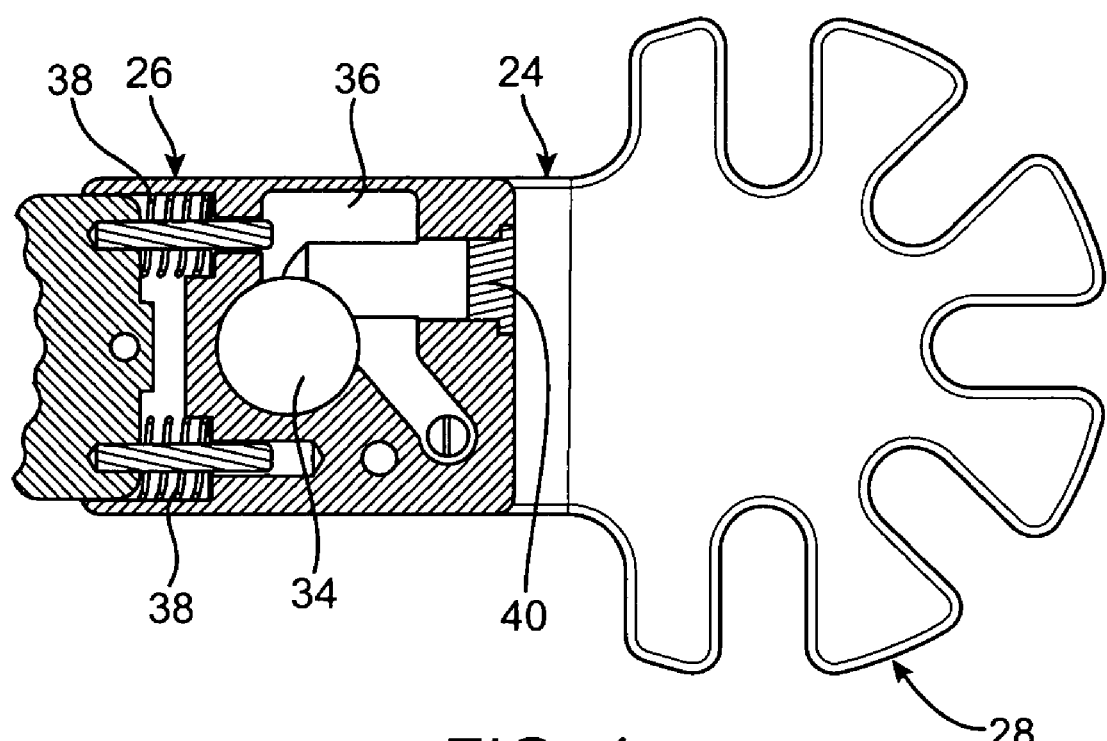
FIG. 4a illustrates a partial cross-sectional view of the main body assembly and main body sub-assembly according to the present invention.
Figure 4B:
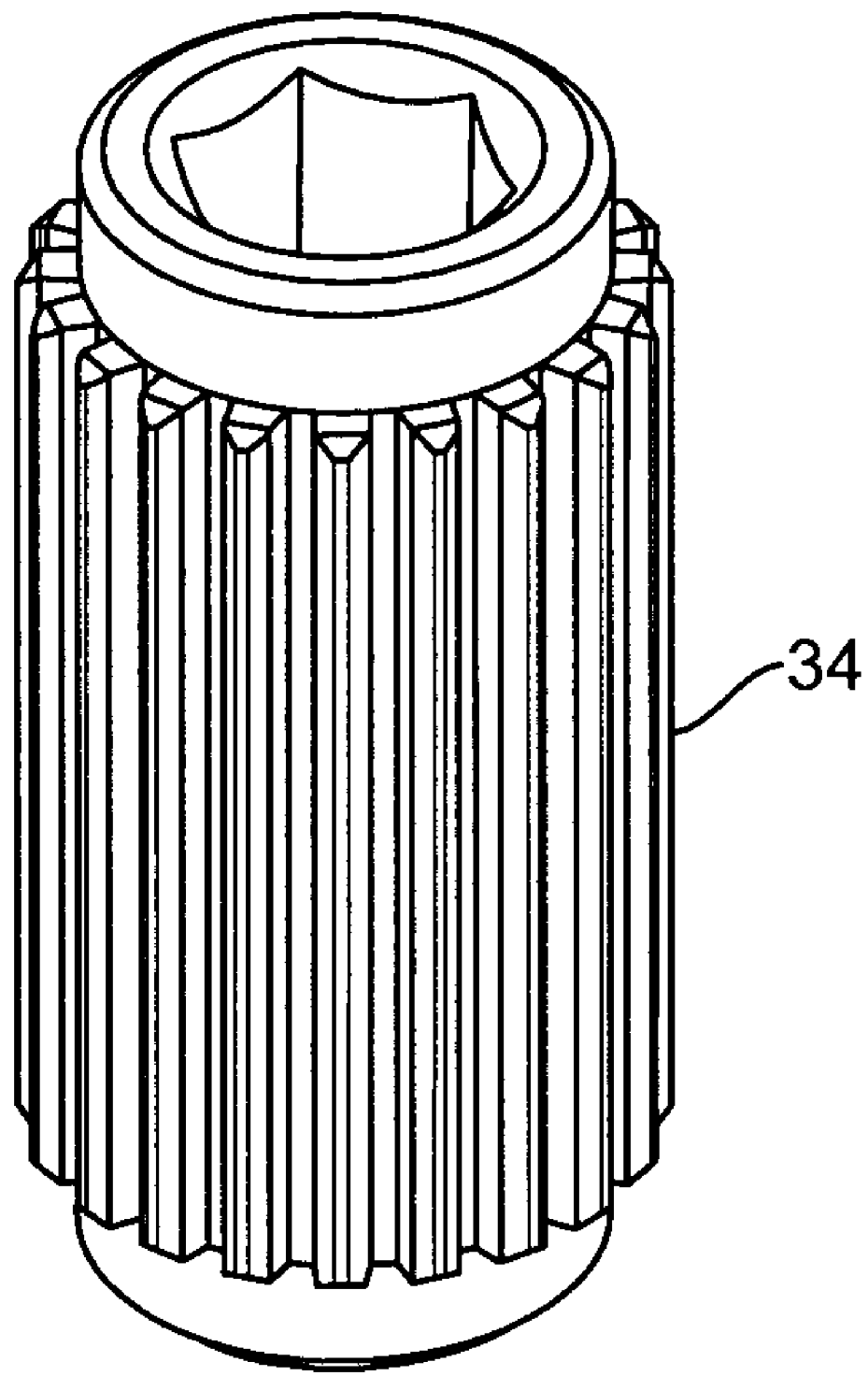
FIG. 4b illustrates a perspective view of a pinion of the main body sub-assembly according to the present invention.
Figure 4C:
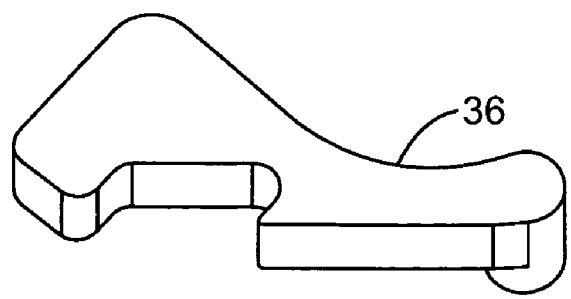
FIG. 4c illustrates a perspective view of the middle pinion lock of the main body sub-assembly according to the present invention.
Figure 4D:
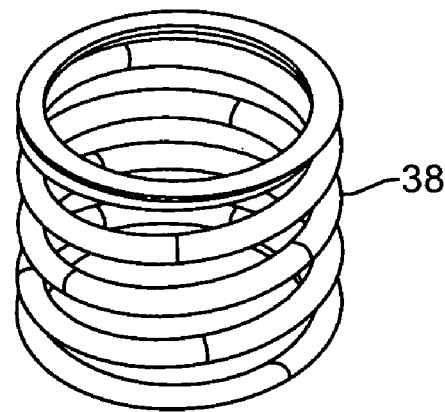
FIG. 4d illustrates a perspective view of a spring of the main body sub-assembly according to the present invention.
Figure 4E:
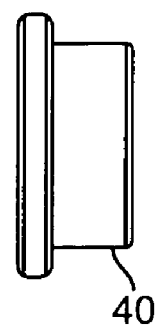
FIG. 4e illustrates a side view of a spring cap of the main body sub-assembly according to the present invention.
Figure 4F:
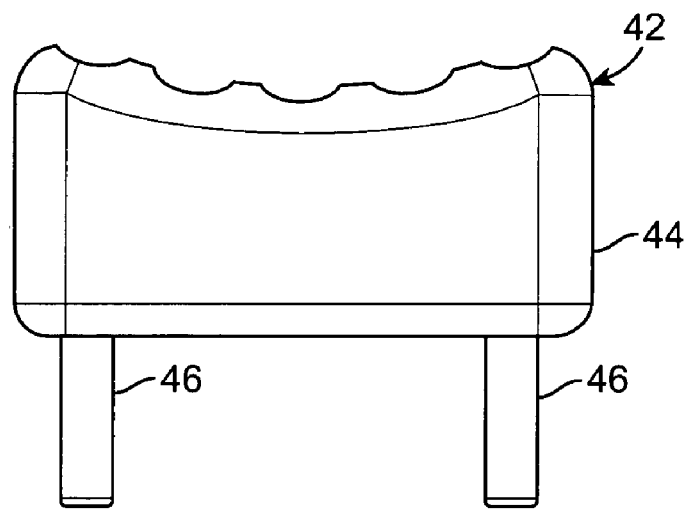
FIG. 4f illustrates a top view of a middle housing release assembly according to the present invention.
Figure 4G:
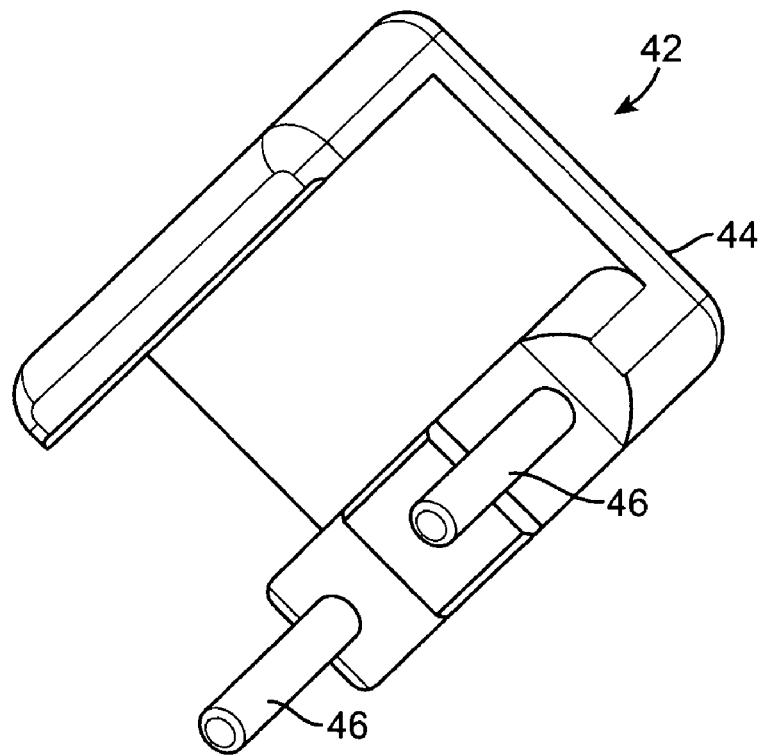
FIG. 4g illustrates a rear perspective view of the middle housing release assembly according to the present invention.
Figure 4H:
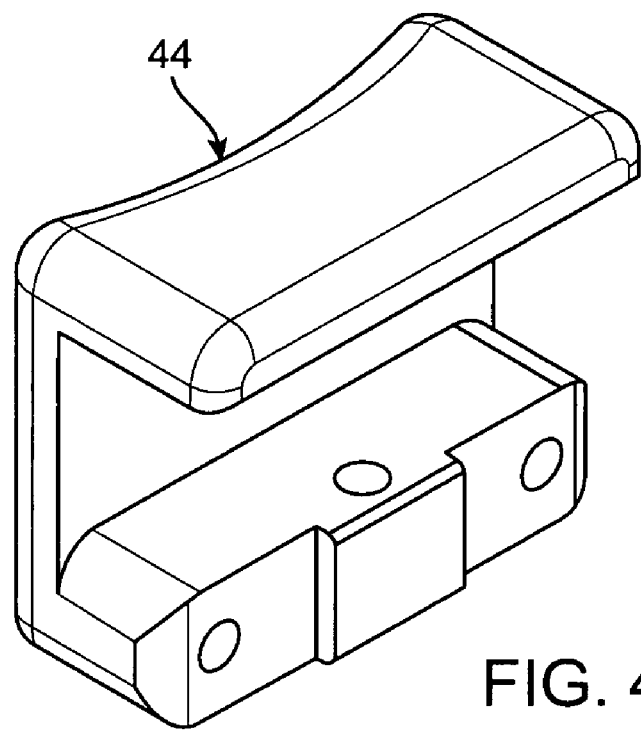
FIG. 4h illustrates a rear perspective view of the release body of the middle housing release assembly according to the present invention.

Referring now to FIGS. 4a, 4b, 4c, 4d, 4e, 4f, and 4g, the components of the main body sub-assembly 26 will now be described. The main body sub-assembly 26 includes a middle pinion 34 (shown in FIG. 4b), a middle pinion lock 36 (shown in FIG. 4c), springs 38 (one shown in FIG. 4d), a spring cap 40 (shown in FIG. 4e), and a middle housing release assembly 42 (shown in FIGS. 4f, 4g, and 4h). The middle housing release assembly 42 includes a release body 44 and pins 46 connected thereto as shown in FIGS. 4f and 4g.

Figure 2D:
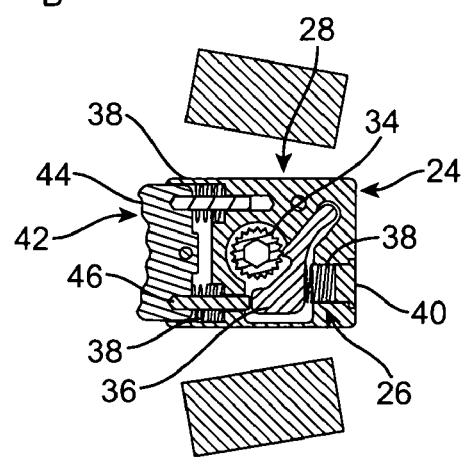
FIG. 2d illustrates a cross-sectional view of the middle assembly along line B-B of FIG. 2c according to the present invention.

Referring back to FIG. 2d, the assembly of the main body sub-assembly 26 inside the main body 28 will now be described. The middle pinion 34 is disposed inside the main body 28 and the middle pinion lock 36 is configured to engage the middle pinion 34. The middle pinion lock 36 is biased by a spring 38 which is held in position by the spring cap 40 inside the main body 28. The lock 36 permits rotation of the middle pinion 34 in one direction locking it from rotation in an opposite direction. The middle housing release assembly 42 is connected to the main body assembly 24 and configured such that two springs 38 bias the release body 44 outwardly and such one of the pins 46 engage the lock 36 when the release body 44 is depressed to thereby unlock the middle pinion 34 allowing it to rotate in the opposite direction.

Referring now to FIGS. 5a, 5b, 5c, 5d, 5e, 5f, and 5h the upper right rack assembly 14 will now be described. The upper right rack assembly 14 includes a rack support 48 (shown in FIGS. 5b and 5c), a straight rack 50 (shown in FIG.

Figure 5A:
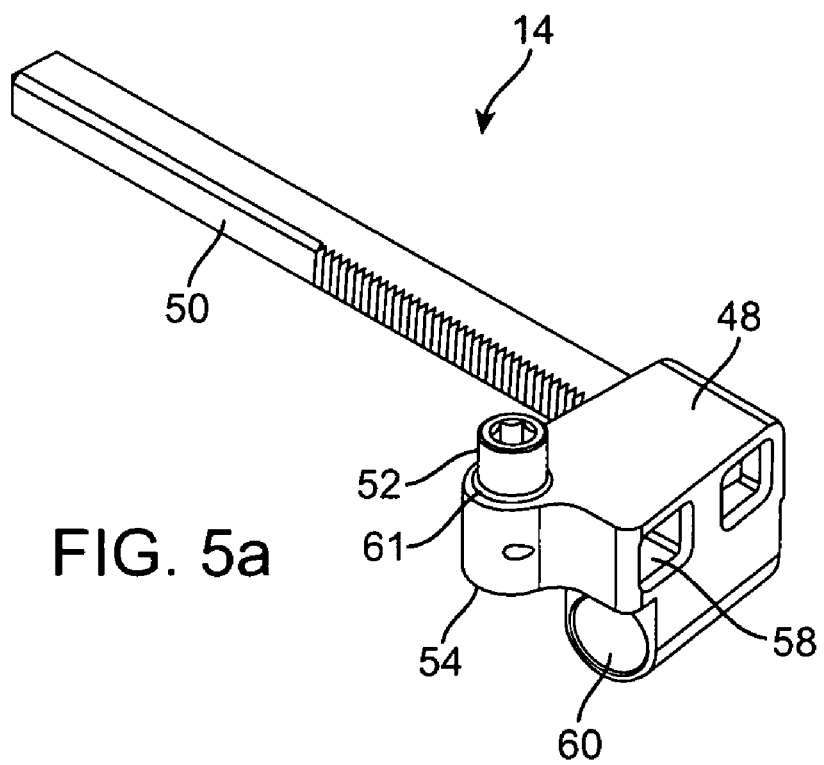
FIG. 5a illustrates a perspective view of an upper right rack assembly according to the present invention.
Figure 5B:
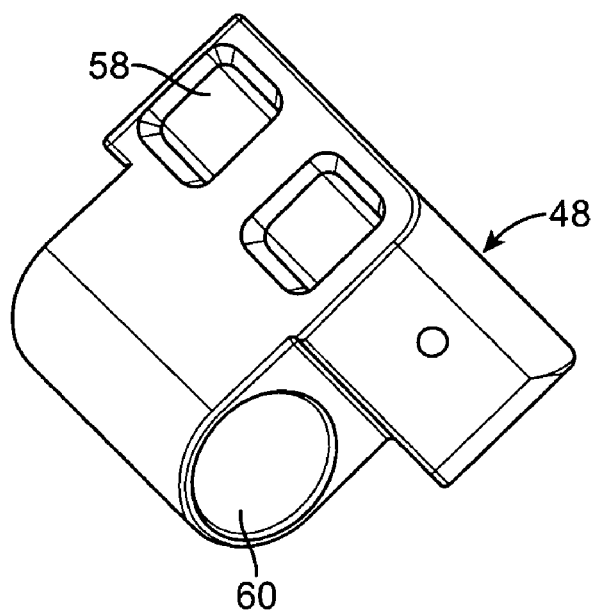
FIG. 5b illustrates a perspective view of a rack support of an upper right rack assembly according to the present invention.
Figure 5C:
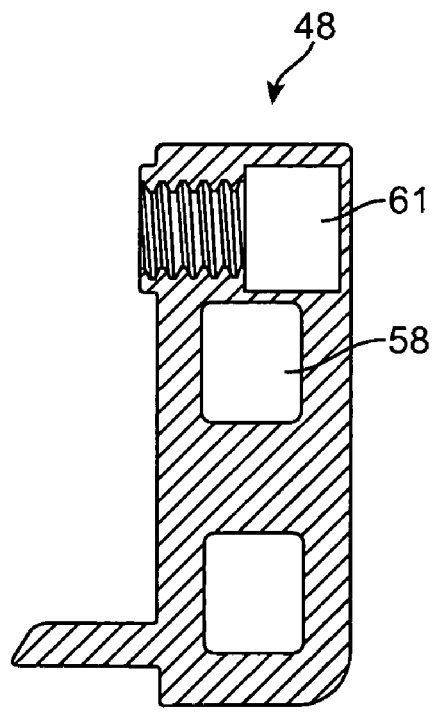
FIG. 5c illustrates a cross-sectional view of a rack support of an upper right rack assembly according to the present invention.
Figure 5D:
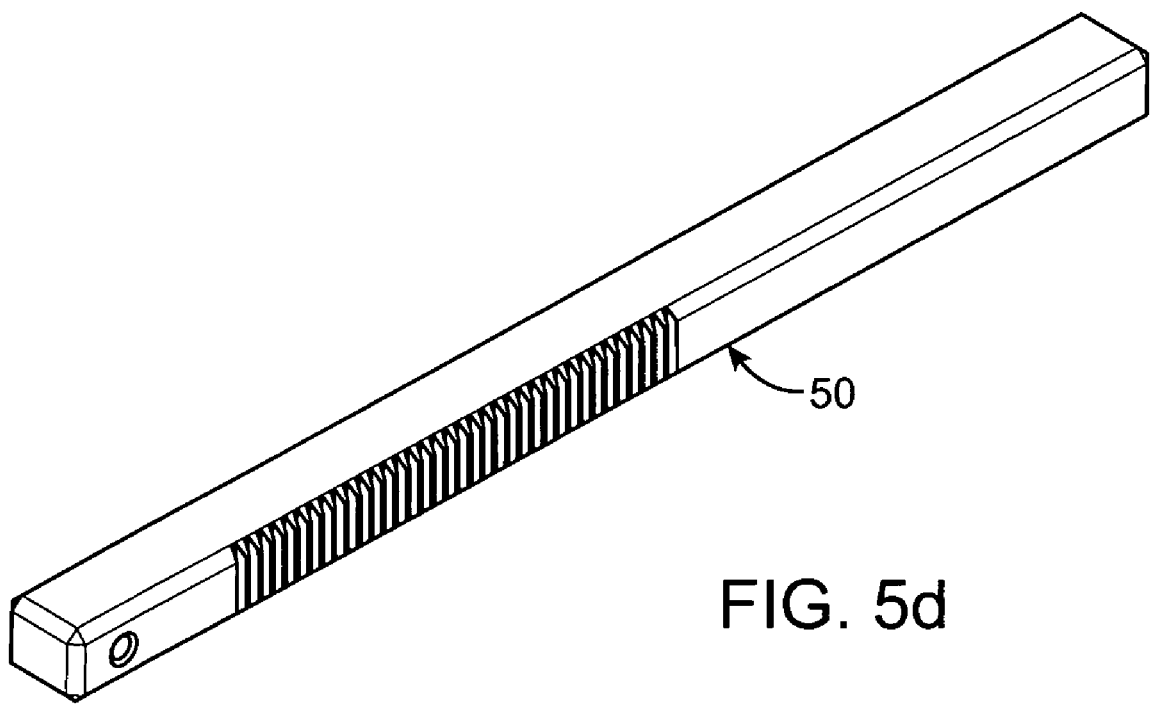
FIG. 5d illustrates a perspective view of a straight rack of an upper right rack assembly according to the present invention.
Figure 5E:
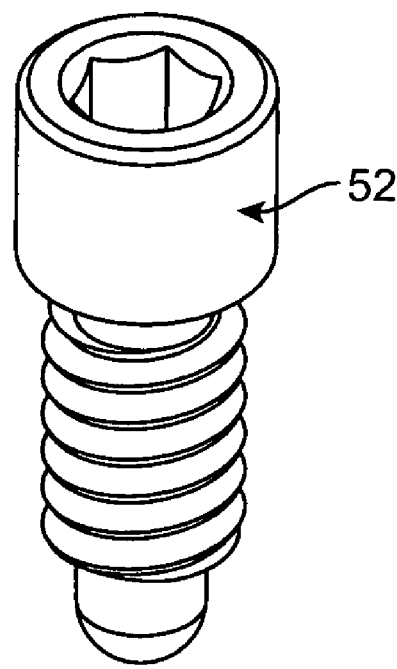
FIG. 5e illustrates a perspective view of a tow angle post of an upper right rack assembly according to the present invention.
Figure 5F:
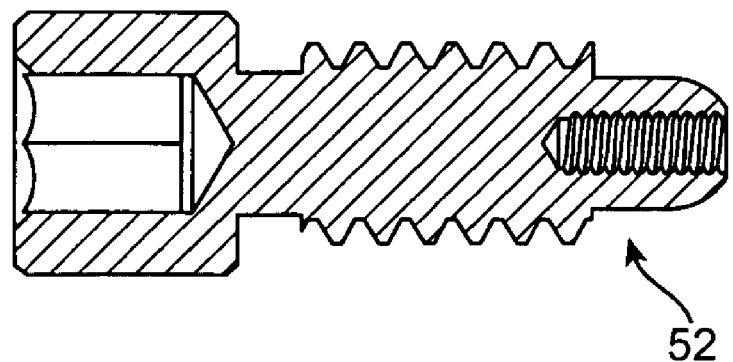
FIG. 5f illustrates a cross-sectional view of a tow angle post of an upper right rack assembly according to the present invention.
Figure 5G:
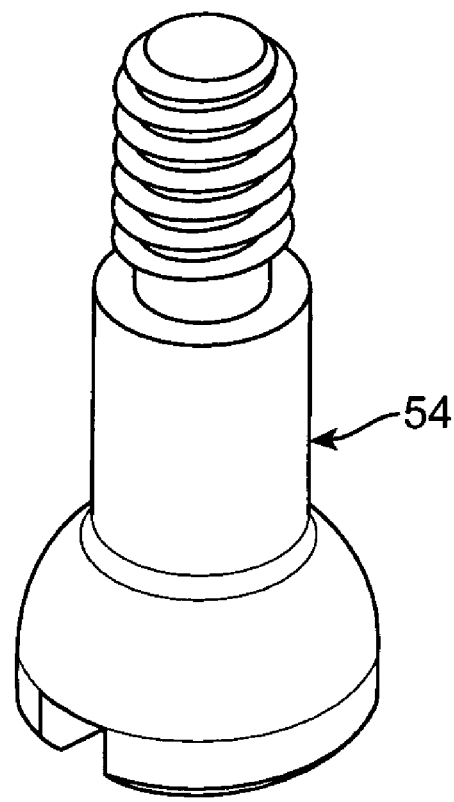
FIG. 5g illustrates a perspective view of a tow angle return of an upper right rack assembly according to the present invention.
Figure 5H:
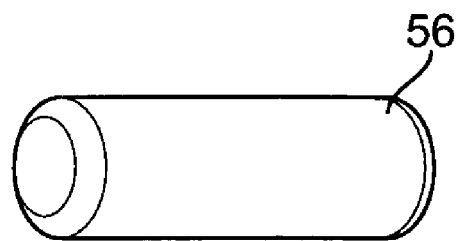
FIG. 5h illustrates a perspective view of a pin of an upper right rack assembly according to the present invention.

5*d*), tow angle post 52 (shown in FIGS. 5*e* and 5*f*), and tow angle return 54 (shown in FIG. 5*g*). The straight rack 50 is inserted into the rack support 48 and connected by a pin 56 like the one shown in FIG. 5*h*. As shown in FIG. 5*b*, the rack support 48 includes a passageway 58 for receiving a straight rack 50 of the upper left rack assembly 16. The rack support 48 also includes a second passageway 60 for receiving and connecting to the right assembly 18. The tow angle post 52 is inserted into a threaded aperture 61 in the rack support 48 and threadingly connected thereto. The tow angle return 54 is inserted into and threadingly connected to the distal end of the tow angle post 52. As such, the tow angle post 52 and the tow angle return 54 are configured to capture the right assembly 18 therebetween to control the angulation and rotation of the right assembly 18 with respect to the upper right rack assembly 14 as will be described in greater detail below.

Figure 6B:
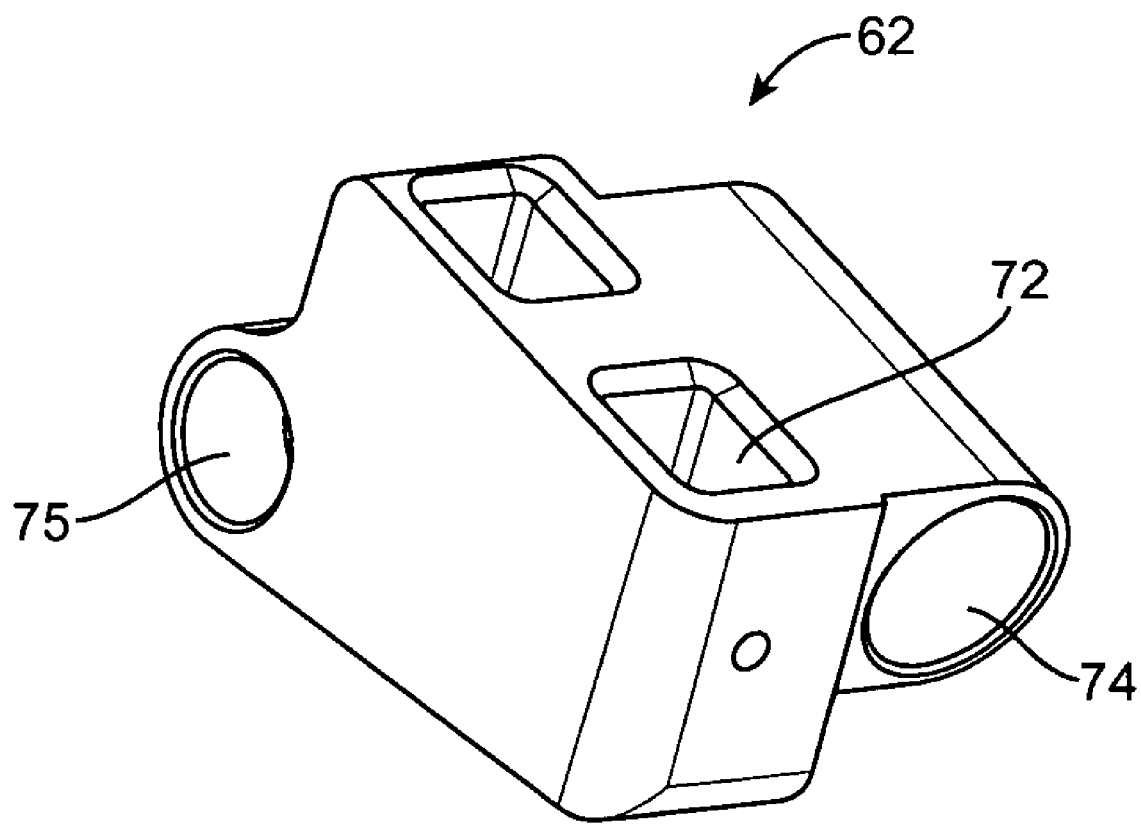
FIG. 6b illustrates a perspective view of a rack support of an upper left rack assembly according to the present invention.

Turning now to FIGS. 6*a* and 6*b*, the upper left rack assembly 16 will now be described. The upper left rack assembly 16 includes a rack support 62 (shown in FIG. 6*b*), a straight rack 64, tow angle post 66, and tow angle return (not shown). The straight rack 64 is inserted into the rack support 62 and connected by a pin (not shown but like the one shown in FIG. 5*h*). The rack support 62 includes a passageway 72 for receiving the straight rack 50 of the upper right rack assembly 14. The rack support 62 also includes a second passageway 74 for receiving and connecting to the left assembly 20. The tow angle post 66 is inserted into a threaded aperture 75 formed in the rack support 62 and threadingly connected thereto. The tow angle return 68 is inserted into and threadingly connected to the distal end of the tow angle post 66 similarly as described above with respect the upper right rack assembly 14. As such, the tow angle post 66 and the tow angle return 68 are configured to capture the left assembly 20 therebetween to control the angulation and rotation of the left assembly 20 with respect to the upper left rack assembly 16 as will be described in greater detail below.

Figure 7:
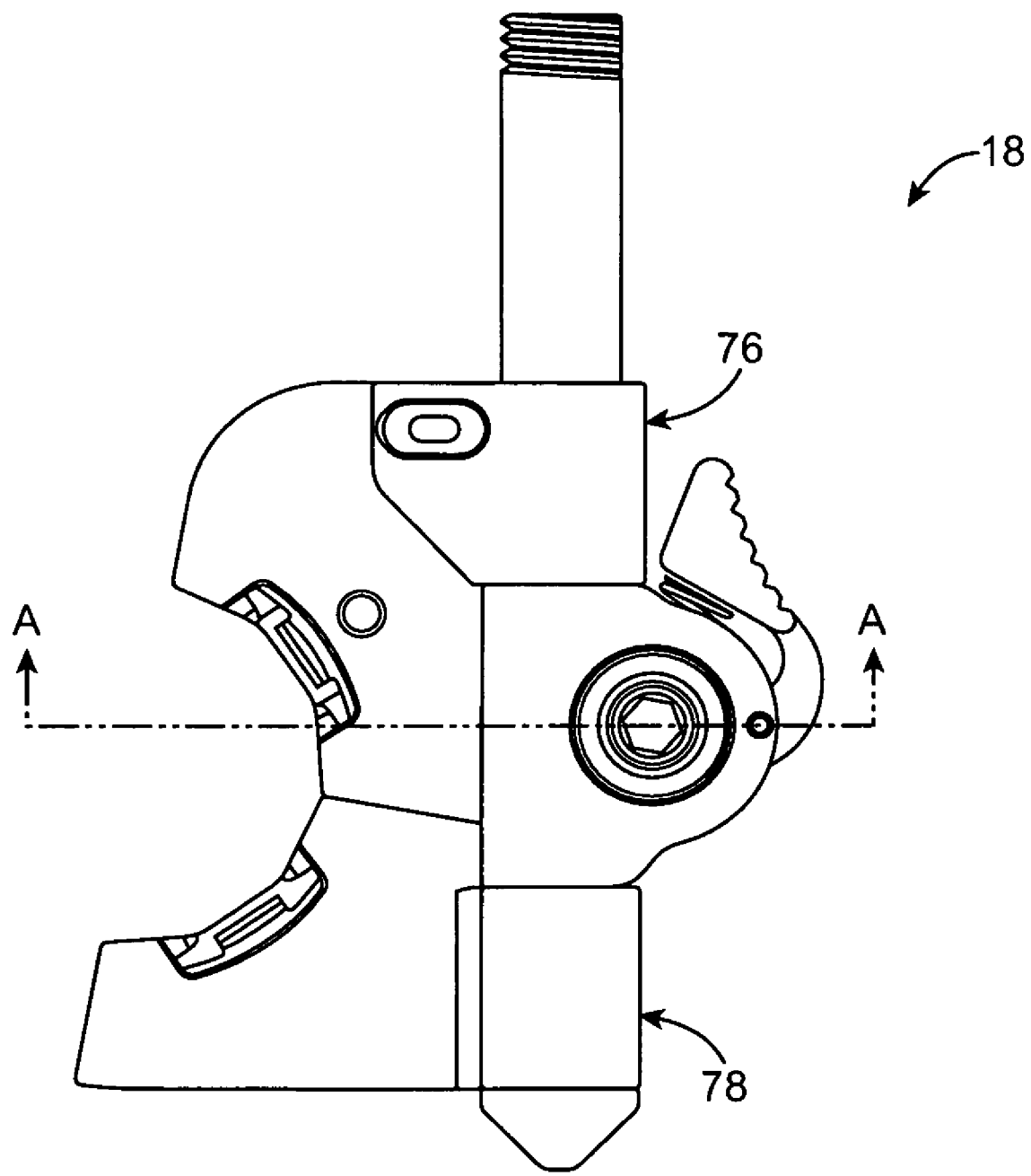
FIG. 7 illustrates a top view of a right assembly according to the present invention.

Turning now to FIG. 7, the right assembly 18 will now be described. The right assembly 18 includes an upper right blade support assembly 76 connected to a lower right blade support assembly 78.

Figure 8H:
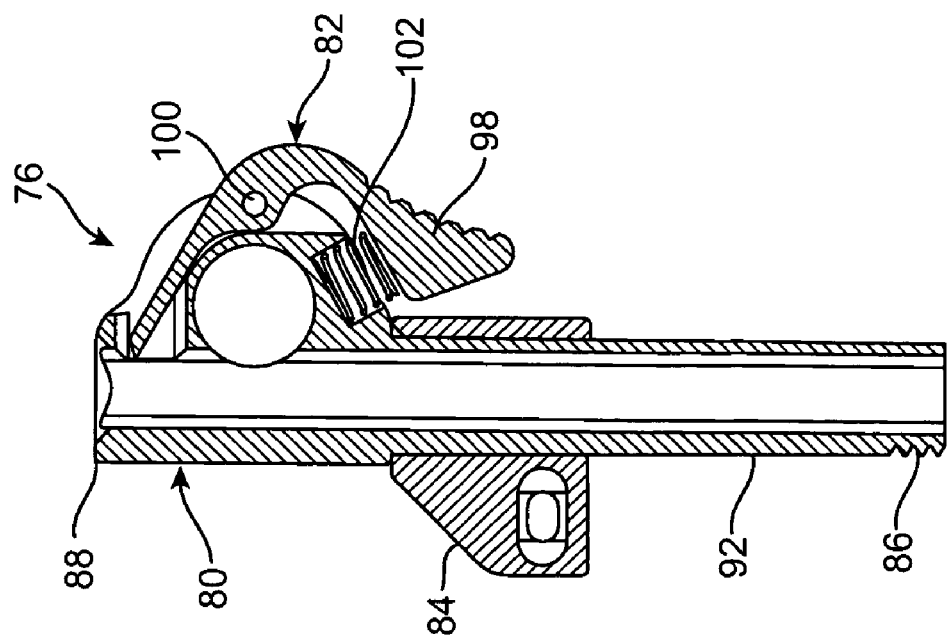
FIG. 8h illustrates a cross-sectional view of an upper right blade support assembly according to the present invention.
Figure 8A:
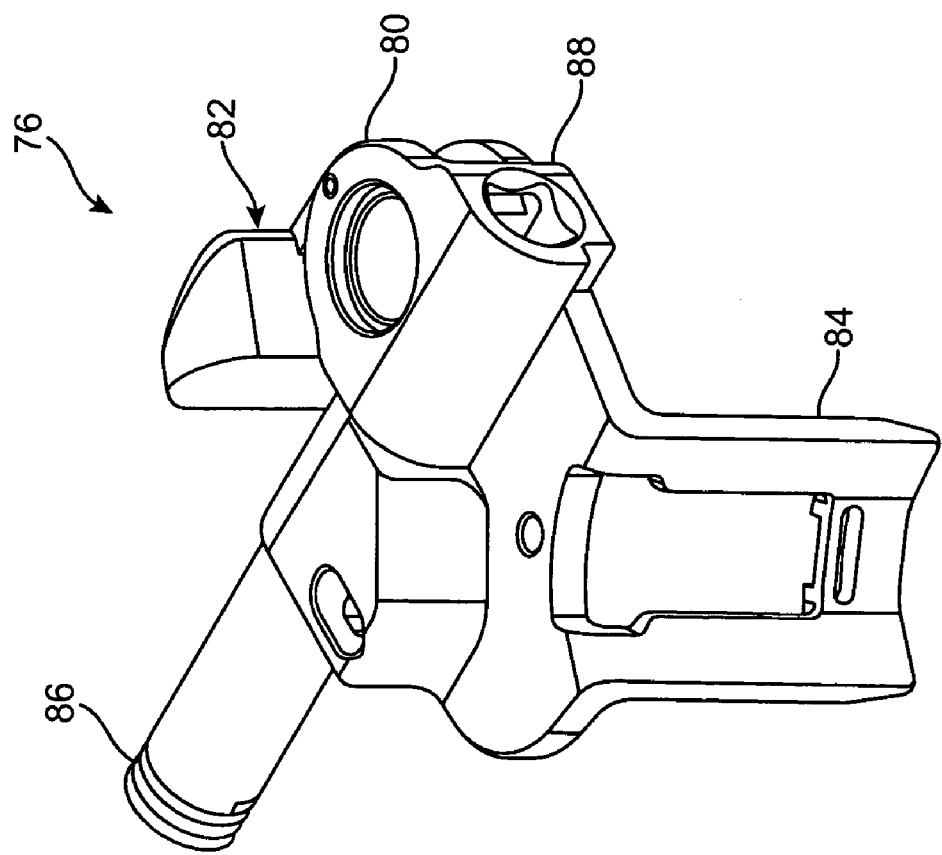
FIG. 8a illustrates a perspective view of an upper right blade support assembly according to the present invention.

Turning now to FIG. 8*a*, the upper right blade support assembly 76 will now be described. The upper right blade support assembly 76 includes a mounting arm 80 connected to a mounting arm sub-assembly 82 and blade support 84.

Figure 8B:
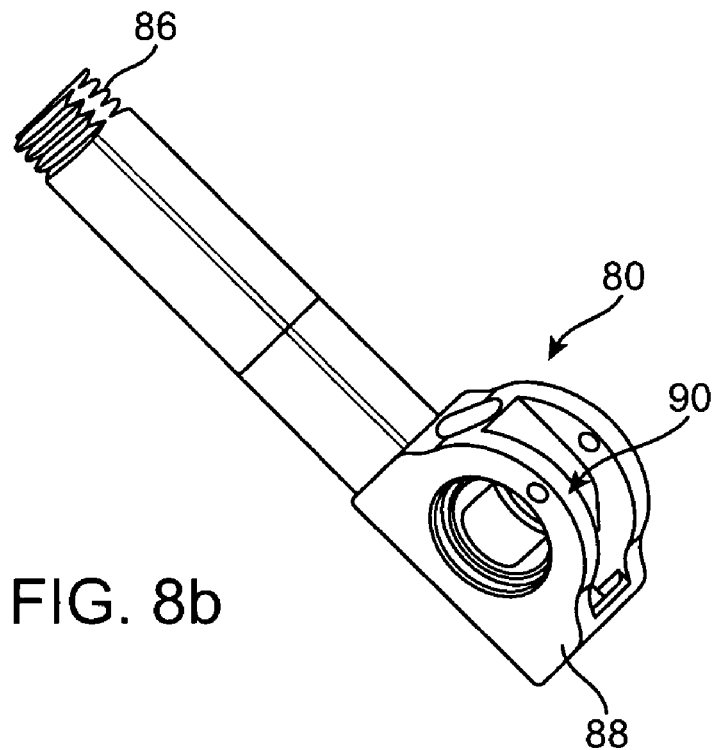
FIG. 8b illustrates a perspective view of a mounting arm of an upper right blade support assembly according to the present invention.
Figure 8C:
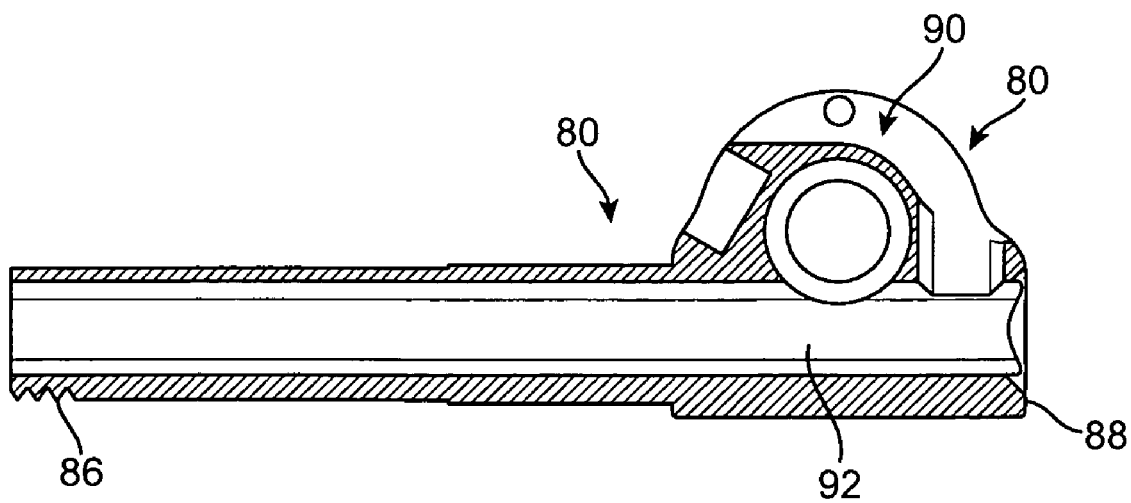
FIG. 8c illustrates a cross-sectional view of a mounting arm of an upper right blade support assembly according to the present invention
Figure 8D:
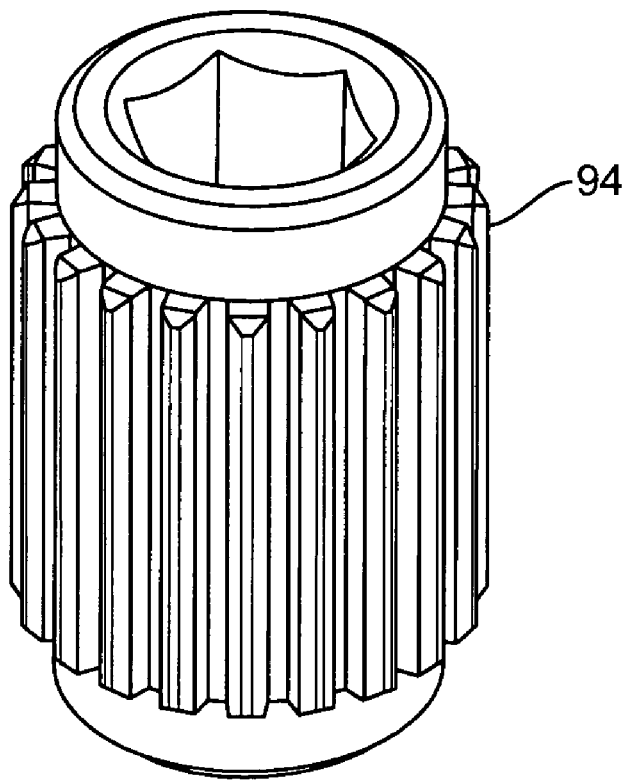
FIG. 8d illustrates a pinion of a mounting arm sub-assembly according to the present invention.
Figure 8E:
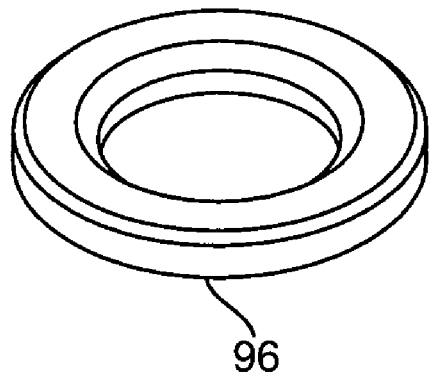
FIG. 8e illustrates a perspective view of a retaining collar of a mounting arm sub-assembly according to the present invention.
Figure 8F:
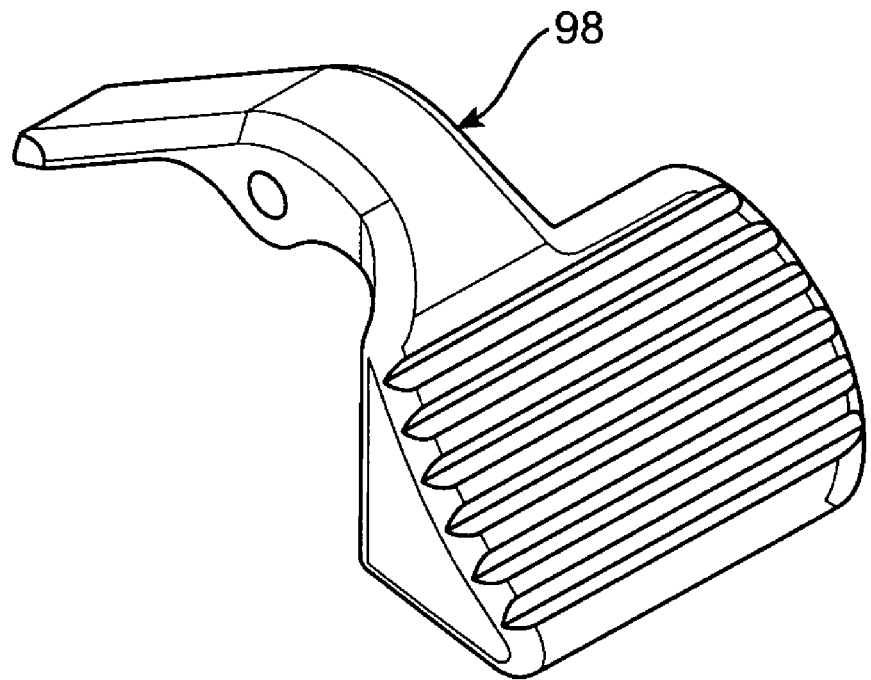
FIG. 8f illustrates a perspective view of a gear lock of a mounting arm sub-assembly according to the present invention.
Figure 8G:
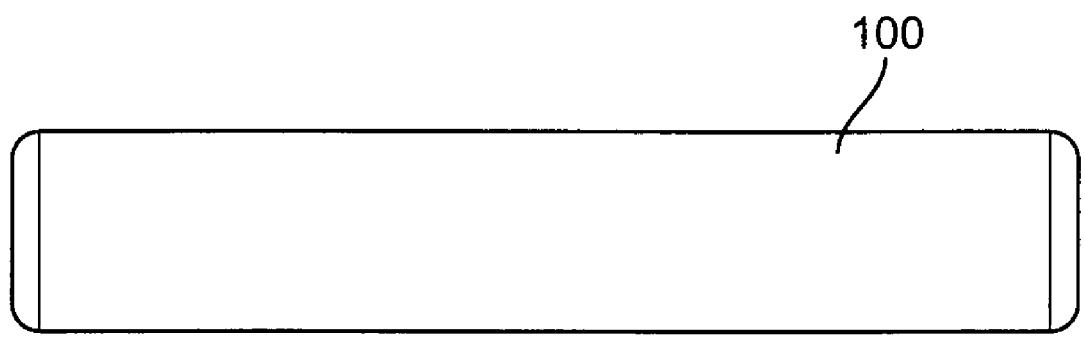
FIG. 8g illustrates a side view of a pin of a mounting arm sub-assembly according to the present invention.

Turning now to FIGS. 8*b* and 8*c*, there is shown a mounting arm 80 according to the present invention. The mounting arm 80 includes a mounting arm longitudinal axis, a threaded proximal end 86, a distal end 88, a mounting arm sub-assembly receiving portion 90 located near the distal end 88 and a central bore 92 extending between the proximal end 86 and distal end 88. The mounting arm 80 is configured to be received within passageway 60 of the upper right rack assembly 14.

Turning now to FIGS. 8*d*, 8*e*, 8*f*, 8*g*, and 8*h*, the mounting arm sub-assembly 82 will now be described. The mounting arm sub-assembly 82 includes a pinion 94 (shown in FIG. 8*d*), retaining collar 96 (shown in FIG. 8*e*), gear lock 98 (shown in FIG. 8*f*), and a pin 100 (shown in FIG. 8*g*). The pinion 94 is disposed inside the mounting arm 80 and retained therein with the retaining collar 96. With particular reference back to FIG. 8*h*, the gear lock 98 is connected to the mounting arm 80 via pin 100 and configured for contact with a ratcheting pin (not shown) and in turn with the pinion. A spring 102 is employed to bias the gear lock 98 against a ratcheting pin (not shown) in the central bore 92 to lock the ratcheting pin and pinion 94 in position. The gear lock 98 is configured such that pinion which is interconnected to the ratcheting via teeth is allowed to rotate in one direction locking it from rotation in an opposite direction. The gear lock 98 can be depressed to thereby unlock the pinion 94 allowing it to rotate in the opposite direction.

Figure 8J:
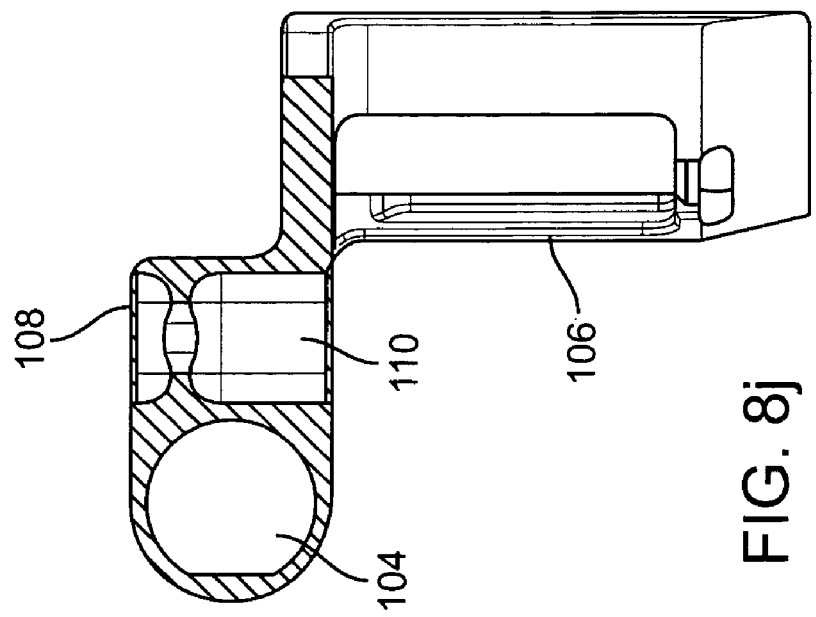
FIG. 8j illustrates a partial cross-sectional view of a blade support according to the present invention.
Figure 8I:
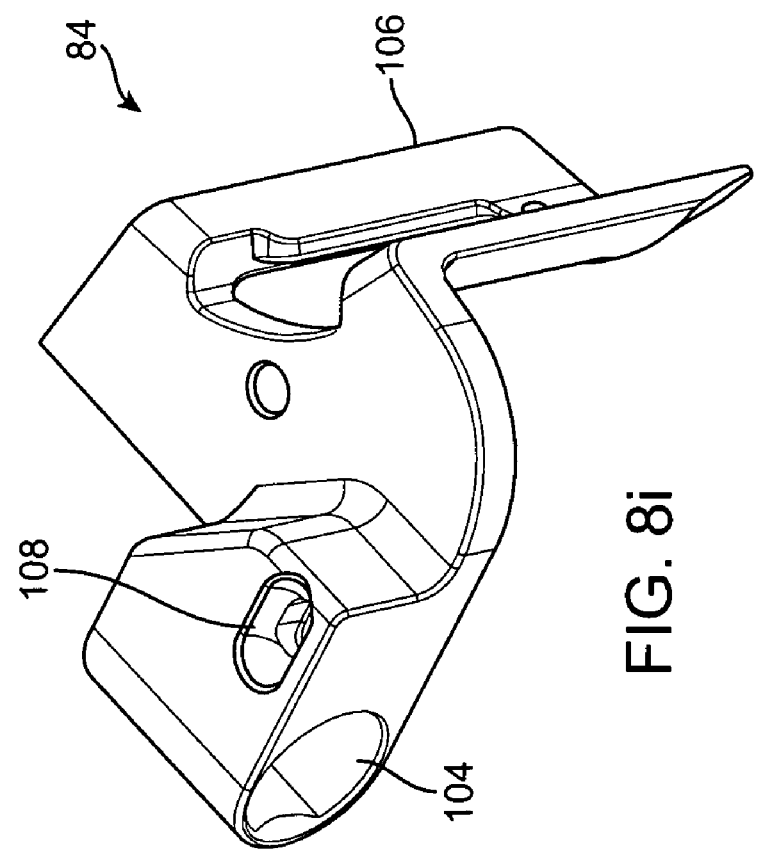
FIG. 8i illustrates a perspective view of a blade support according to the present invention.

Turning now to FIGS. 8*i* and 8*j*, there is shown the blade support 84 according to the present invention. The blade support 84 includes a mounting arm receiving portion 104, a blade flange 106 configured for attachment to a blade 22, a tow angle post receiving portion 108 and a tow angle return receiving portion 110, both the tow angle post receiving portion 108 and the tow angle return receiving portion 110 both comprising a single bore extending through the blade support 84.

Figure 8K:
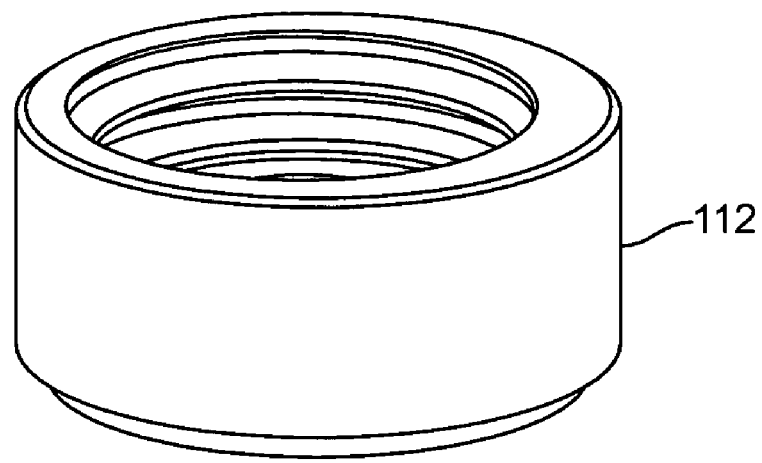
FIG. 8k illustrates a perspective view of a threaded end cap according to the present invention.

The mounting arm 80 is inserted into the mounting arm receiving portion 104 and the mounting arm 80 is inserted into the second passageway 60 of the upper right rack assembly 14. The threaded proximal end 86 is capped with an internally threaded end cap 112 shown in FIG. 8*k*. The mounting arm 80 is oriented and the tow angle post 52 is inserted into the tow angle post receiving portion 108. The tow angle return 54 is inserted into the tow angle return receiving portion 110 and threaded into the tow angle post 52 capturing the blade support 84 therebetween.

Figure 9A:
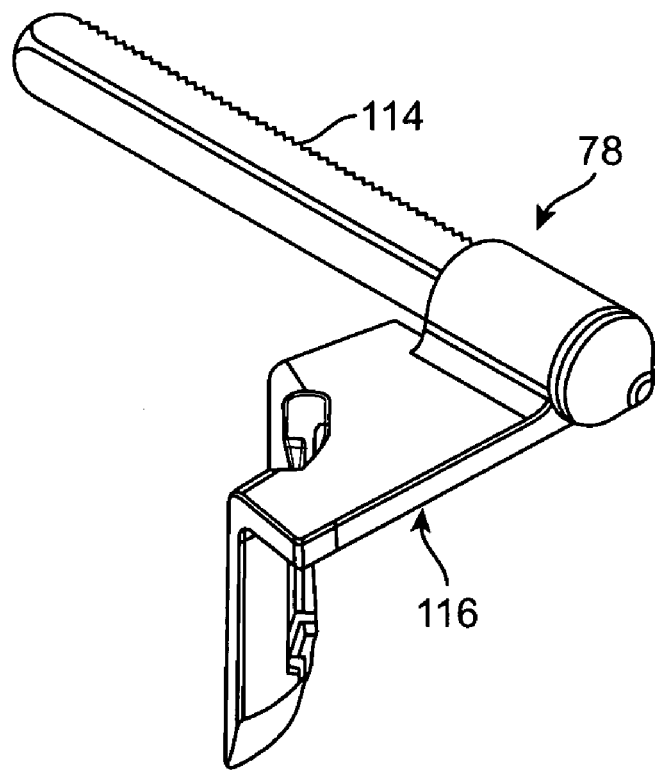
FIG. 9a illustrates a perspective view of a lower right blade support assembly according to the present invention.
Figure 9B:
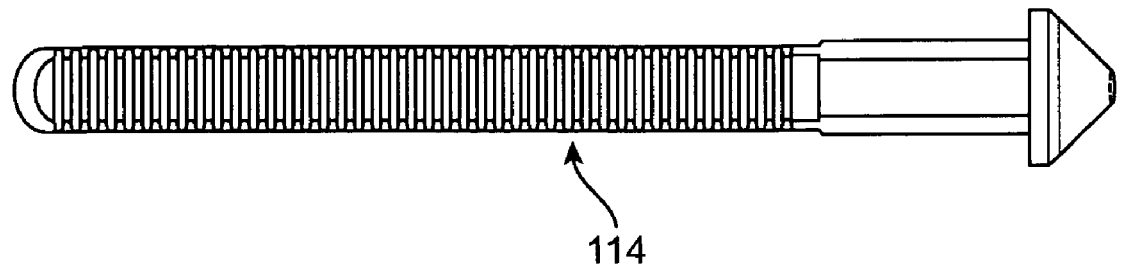
FIG. 9b illustrates a side view of a ratcheting pin according to the present invention.
Figure 9C:
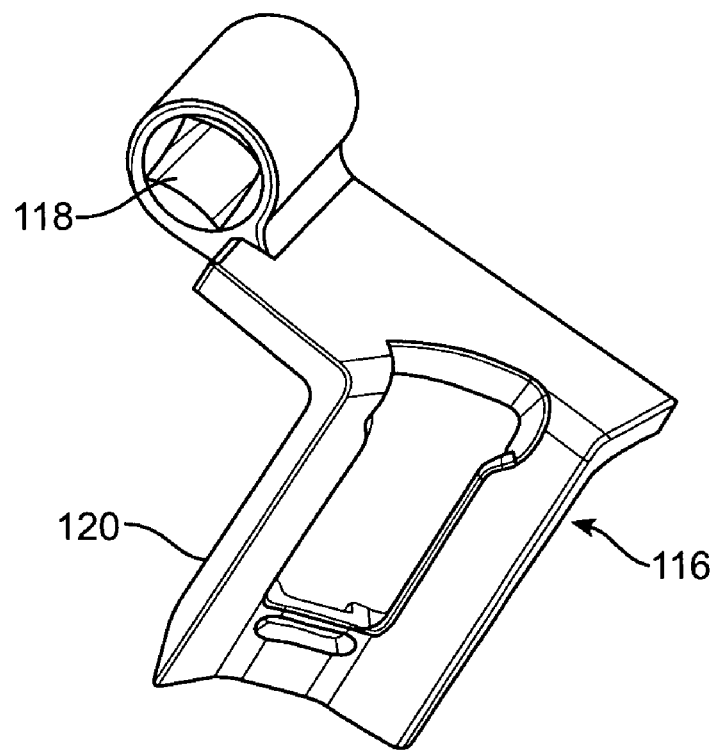
FIG. 9c illustrates a perspective view of a lower right blade support according to the present invention.

Turning now to FIGS. 9*a*, 9*b* and 9*c*, there is shown the lower right blade support assembly 78. The lower right blade support assembly 78 includes a toothed ratcheting pin 114 (shown in FIG. 9*b*) connected to a lower right blade support 116 (shown in FIG. 9*c*).

With particular reference to FIG. 9*c*, the lower right blade support includes a ratcheting pin receiving portion 118 connected to a blade flange 120 configured for attachment to a blade 22. The ratcheting pin 114 is inserted into the ratcheting pin receiving portion 118, one end of which includes a stop and the other end being inserted into the central bore 92 of the mounting arm 80 such that the toothed ratcheting pin 114 engages the teeth of the pinion 94 and is permitted to slide with respect to the upper right blade support assembly 76 upon turning of the pinion 94.

Figure 10:
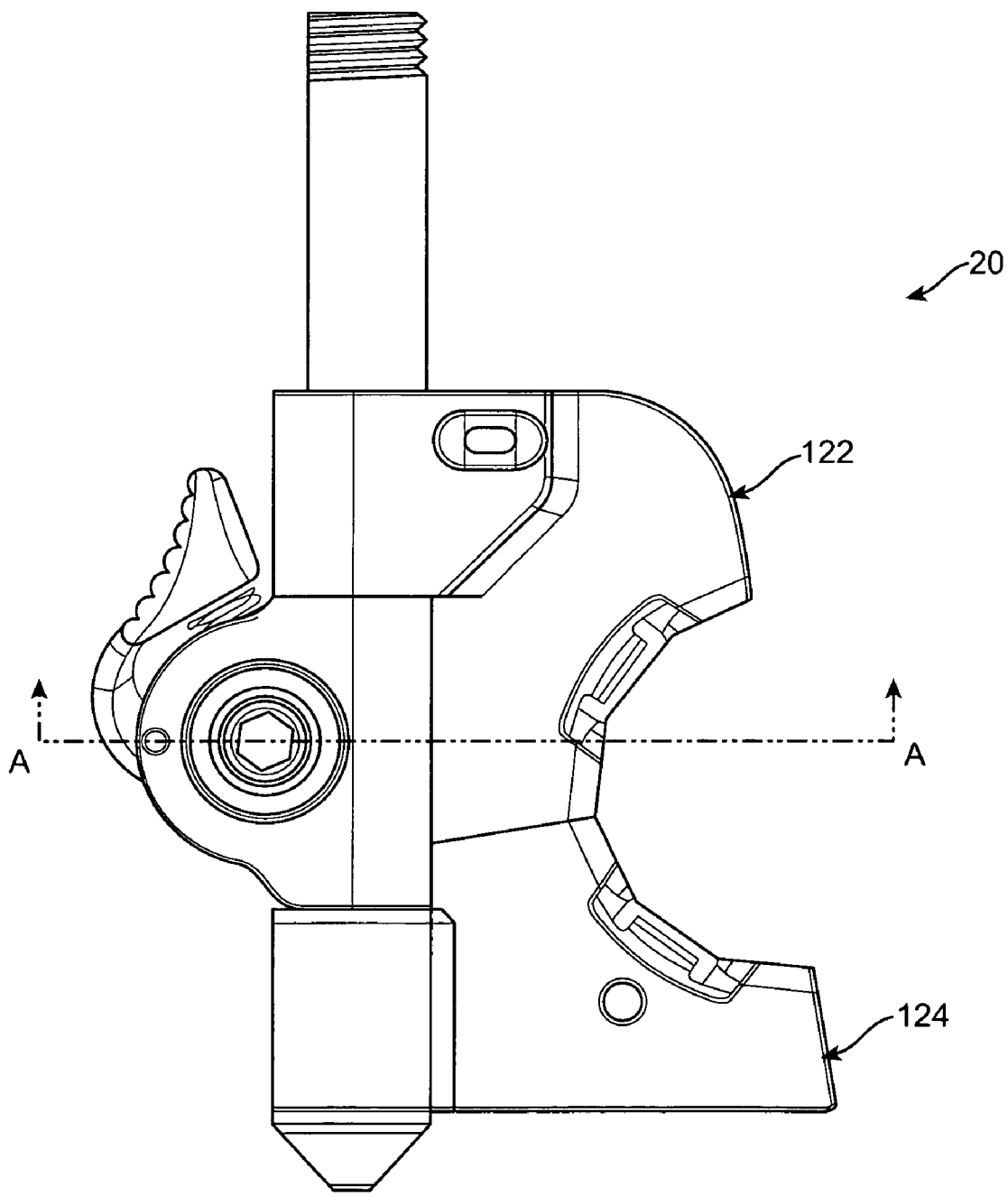
FIG. 10 illustrates a top view of a left assembly according to the present invention.

Turning now to FIG. 10, there is shown the left assembly 20. The left assembly 20 includes an upper left blade support assembly 122 connected to a lower left blade support assembly 124.

Figure 11A:
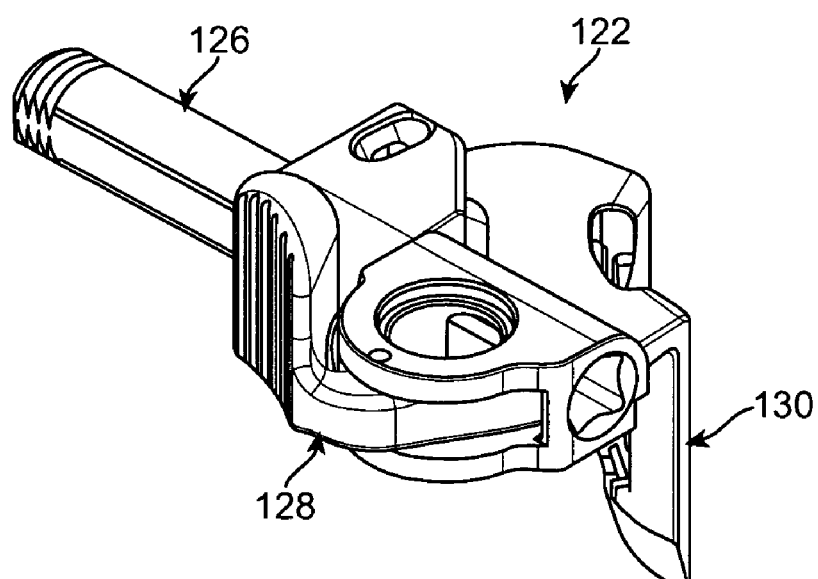
FIG. 11a illustrates a perspective view of an upper left blade support assembly according to the present invention.

Turning now to FIG. 11*a*, the upper left blade support assembly 122 will now be described. The upper left blade support assembly 122 includes a mounting arm 126 connected to a mounting arm sub-assembly 128 and blade support 130.

Figure 11E:
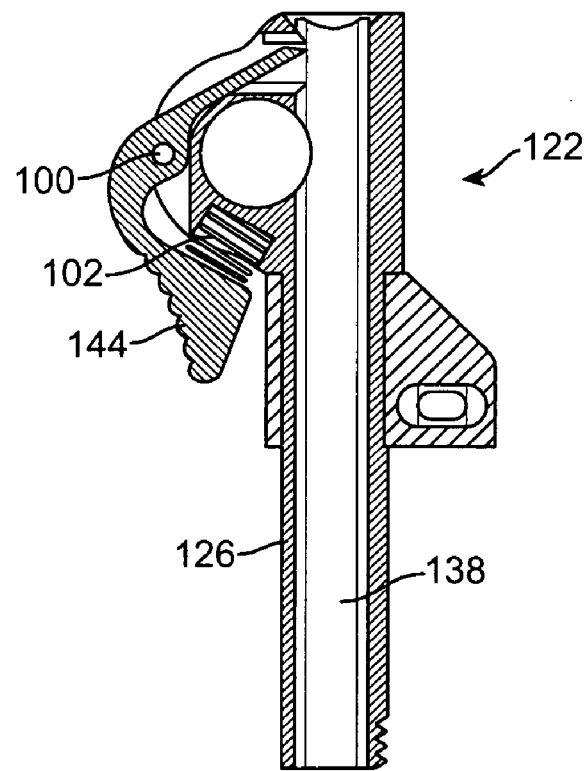
FIG. 11e illustrates a cross-sectional view of an upper left blade support assembly according to the present invention.
Figure 11B:
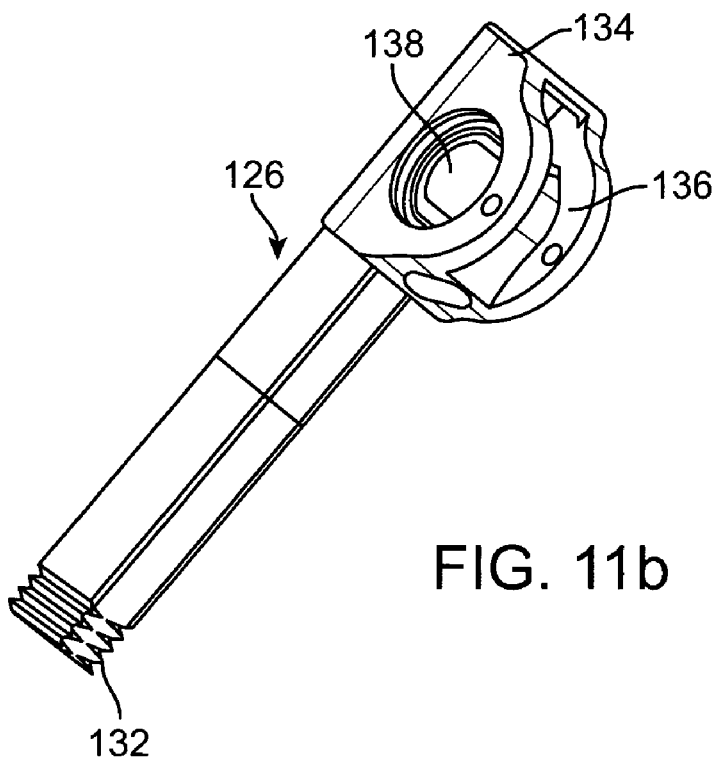
FIG. 11b illustrates a perspective view of a mounting arm of an upper left blade support assembly according to the present invention.
Figure 11C:
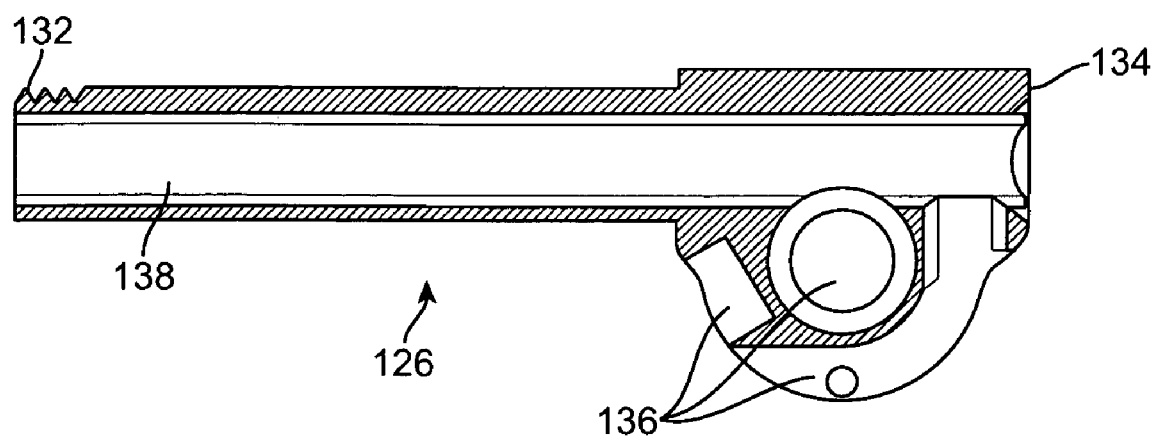
FIG. 11c illustrates a cross-sectional view of a mounting arm of an upper left blade support assembly according to the present invention.

Turning now to FIGS. 11*b* and 11*c*, the mounting arm 126 will now be described. The mounting arm 126 includes a mounting arm longitudinal axis, a threaded proximal end 132, a distal end 134, a mounting arm sub-assembly receiving portion 136 located near the distal end 134 and a central bore 138 extending between the proximal end 132 and distal end 134. The mounting arm 126 is configured to be received within second passageway 74 of the upper left rack assembly 16.

Figure 11D:
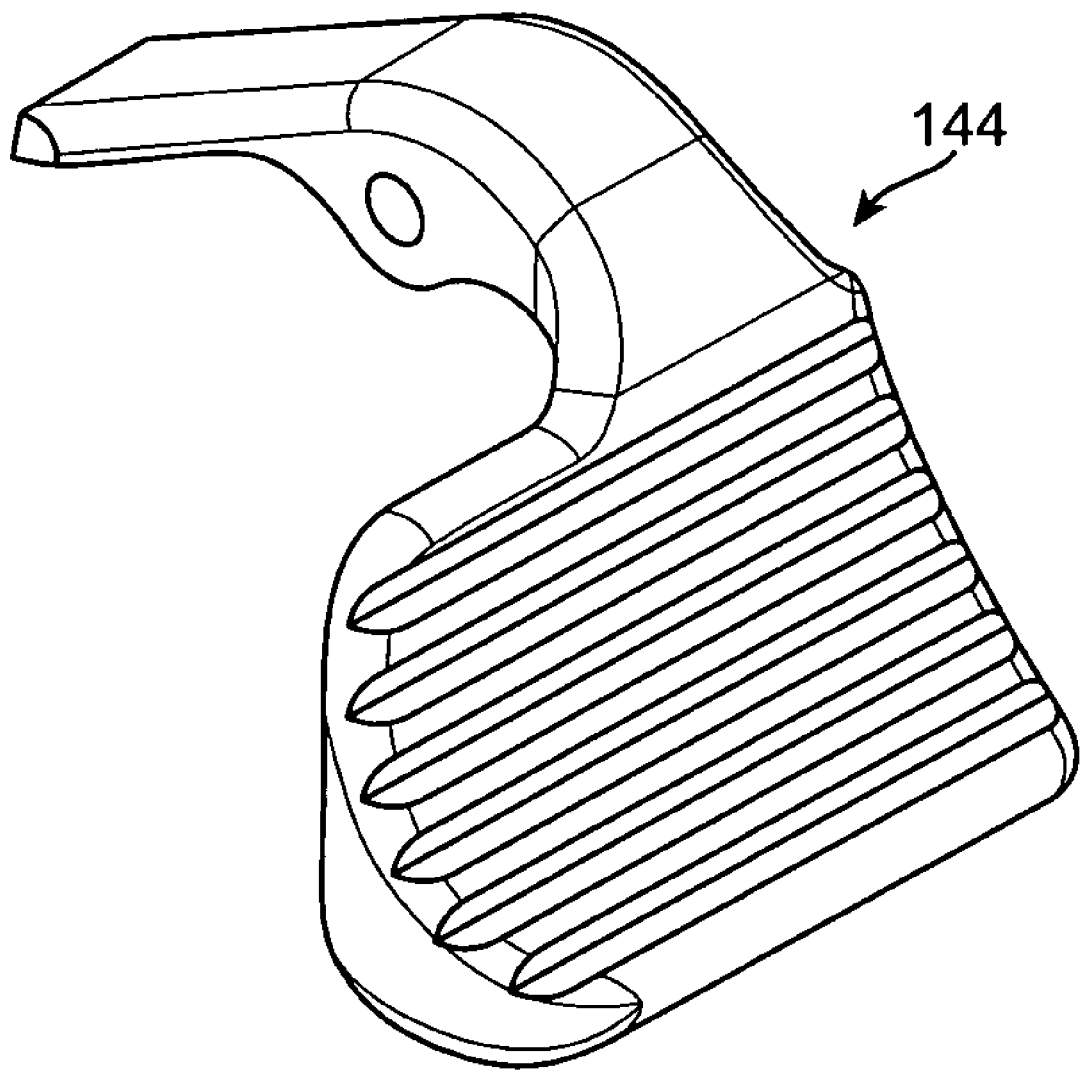
FIG. 11d illustrates a perspective view of a gear lock according to the present invention.

The mounting arm sub-assembly 128 will now be described. The mounting arm sub-assembly 128 includes a pinion (shown in FIG. 8*d*), retaining collar (shown in FIG. 8*e*), gear lock 144 (shown in FIG. 11*d*), and a pin (shown in FIG. 8*g*). The pinion is disposed inside the mounting arm 126 and retained therein with the retaining collar. With particular reference to FIG. 11*e*, the gear lock 144 is connected to the mounting arm 126 via a pin 100 and configured for contact with the pinion (not shown in FIG. 11*e*) via a ratcheting pin (not shown in FIG. 11*e*). A spring 102 is employed to bias the gear lock 144 against a ratcheting pin (not shown) in the central bore 138 to lock the ratcheting pin and the pinion in position. The gear lock 144 is configured such that the pinion is allowed to rotate in one direction locking it from rotation in an opposite direction. The gear lock 144 can be depressed to thereby unlock the pinion allowing it to rotate in the opposite direction.

Figure 11F:
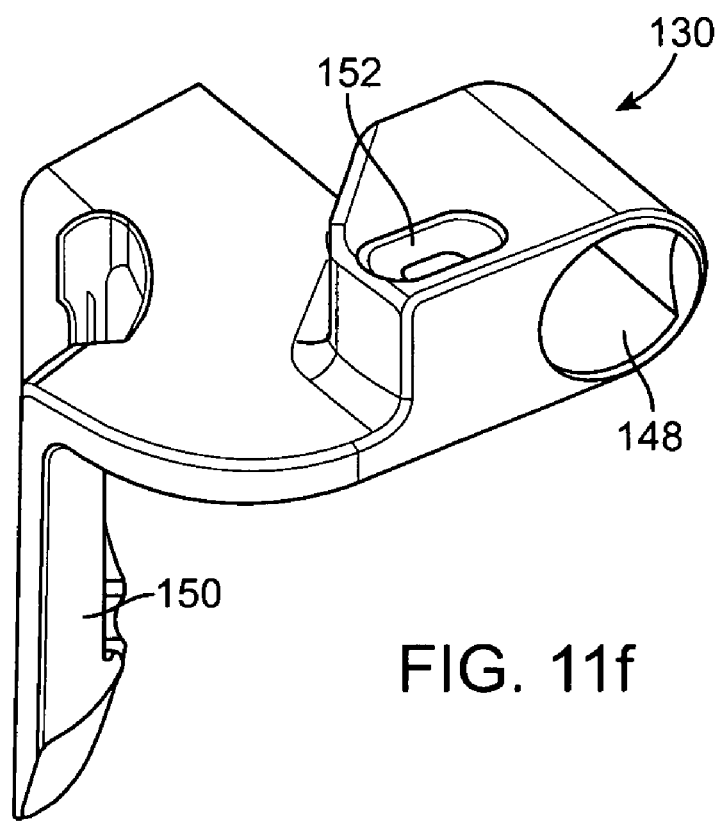
FIG. 11f illustrates a perspective view of a blade support according to the present invention.
Figure 11G:
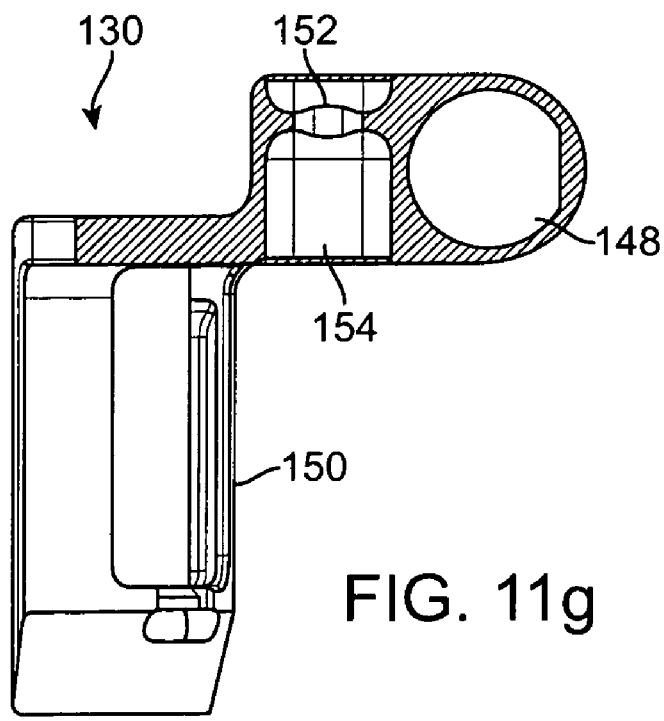
FIG. 11g illustrates a partial cross-sectional view of a blade support according to the present invention.

Turning now to FIGS. 11*f* and 11*g*, the blade support 130 will now be described. The blade support 130 includes a mounting arm receiving portion 148, a blade flange 150 configured for attachment to a blade 22, a tow angle post receiving portion 152 and a tow angle return receiving portion 154 (shown in FIG. 11*g*), both the tow angle post receiving portion 152 and the tow angle return receiving portion 154 comprising a bore extending through the blade support 130.

Assembly of the upper left blade support assembly 122 will now be described. The mounting arm 126 is inserted into the mounting arm receiving portion 148 and the mounting arm 126 is inserted into the second passageway 74 of the upper left rack assembly 16. The threaded proximal end 132 is capped with an internally threaded end cap of the like shown in FIG. 8*k*. The mounting arm 126 is oriented and the tow angle post is inserted into the tow angle post receiving portion 152. The tow angle return is inserted into the tow angle return receiving portion 154 and threaded into the tow angle post capturing the blade support 130 therebetween.

Figure 12A:
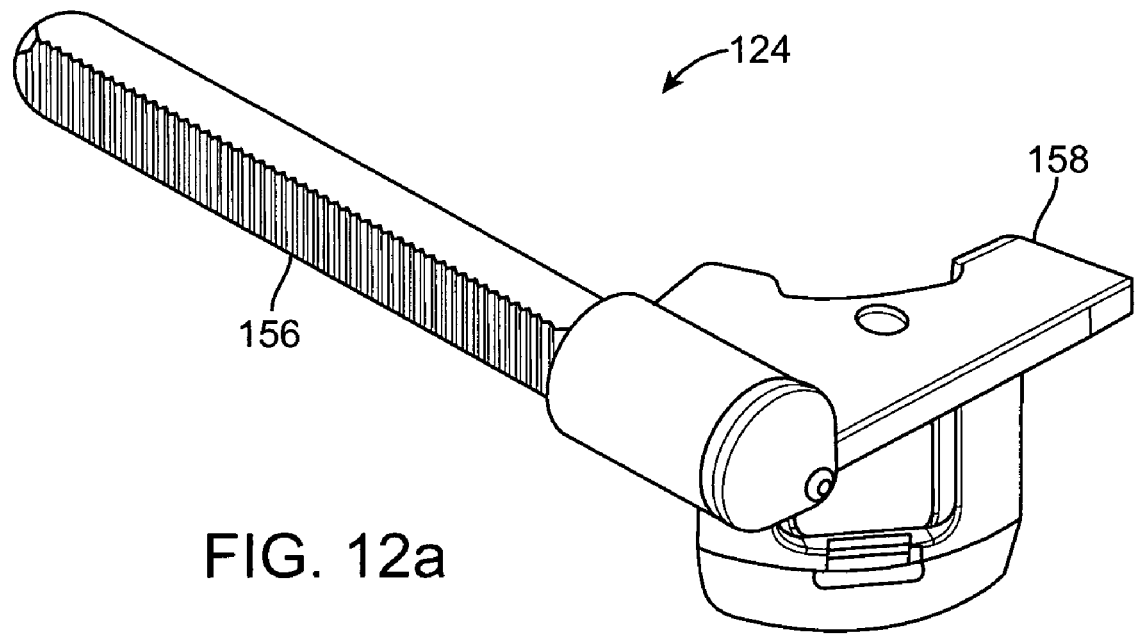
FIG. 12a illustrates a perspective view of a lower left blade support assembly according to the present invention.
Figure 12B:
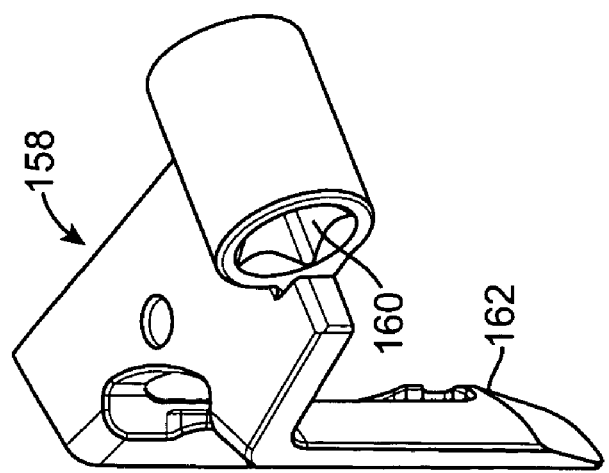
FIG. 12b illustrates a perspective view of a lower left blade support according to the present invention.

Turning now to FIGS. 12*a* and 12*b*, there is shown the lower left blade support assembly 124. The lower left blade support assembly 124 includes a toothed ratcheting pin 156 of the like shown in FIG. 9*b* connected to a lower left blade support 158 (shown in FIG. 12*b*).

With particular reference to FIG. 12*b*, the lower left blade support 158 includes a ratcheting pin receiving portion 160 connected to a blade flange 162 configured for attachment to a blade 22. The ratcheting pin 156 is inserted into the ratcheting pin receiving portion 160, one end of ratcheting pin 156 including a stop and the other end being inserted into the central bore 138 of the mounting arm 126 such that the toothed ratcheting pin 156 engages the teeth of the pinion and is permitted to slide with respect to the upper left blade support assembly 122.

As seen in the figures, the left assembly 20 is a mirror image of the right assembly 18.

Figure 13B:
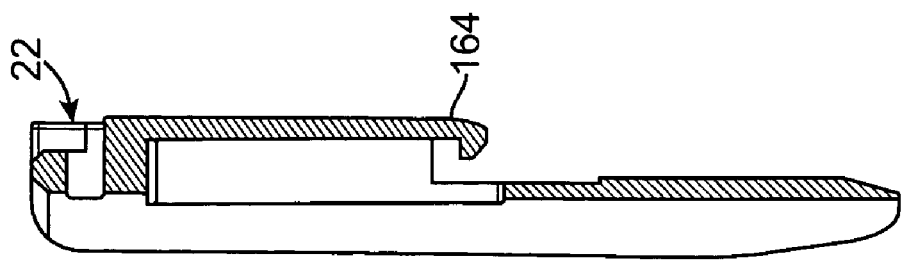
FIG. 13b illustrates a cross-sectional view of a blade according to the present invention.
Figure 13A:
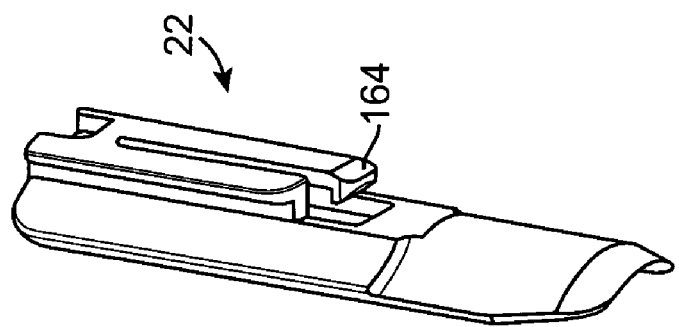
FIG. 13a illustrates a perspective view of a blade according to the present invention.

Turning now to FIGS. 13*a* and 13*b*, there is shown a retractor blade 22 that is configured to be removably attached to the blade supports 84, 116, 130, 158 making the blades 22 interchangeable with other blades of different length(s). The blade 22 includes a hook or tang 164 for connecting with the blade supports. The hook 164 is capable of deflection to capture and release a retractor blade 22.

Figure 14:
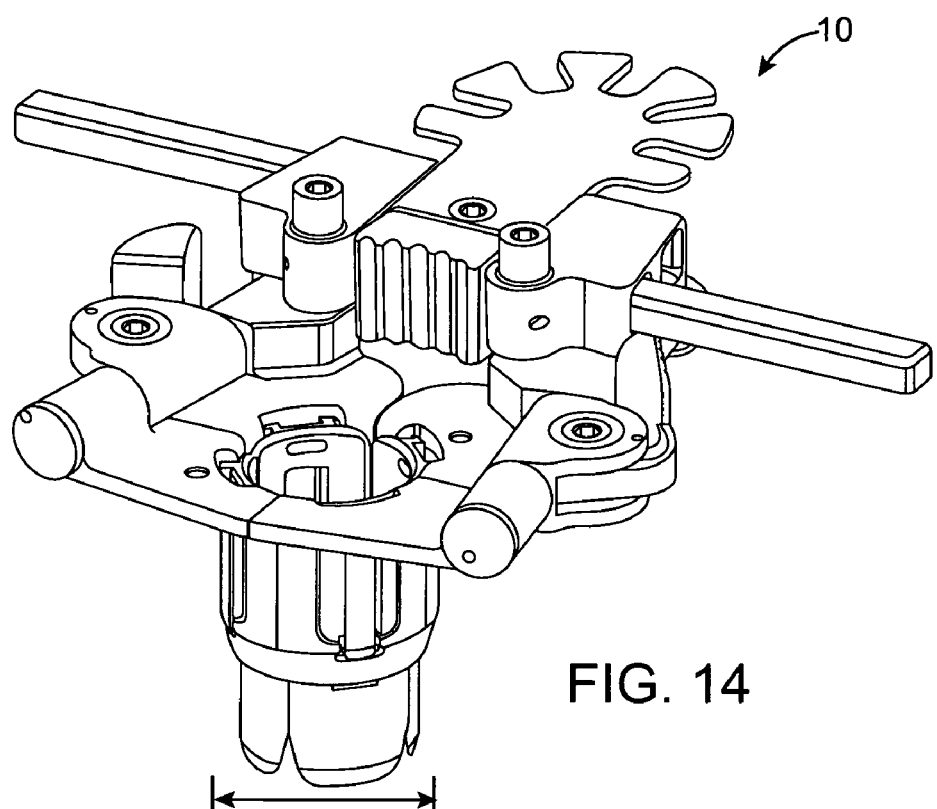
FIG. 14 illustrates a retractor in a closed configuration according to the present invention.

The use of the retractor will now be discussed. With reference to FIG. 14, the entry point for the retractor 10 into the patient is determined with anterior, posterior and lateral fluoroscopy. An incision is made in the patient that is slightly larger than the width dimension W of the closed retractor base. The closed retractor base dimension W is shown in FIG. 14 to be approximately 2.0 to 5.0 centimeters in one variation and in another variation approximately 2.6 centimeters.

Figure 15:
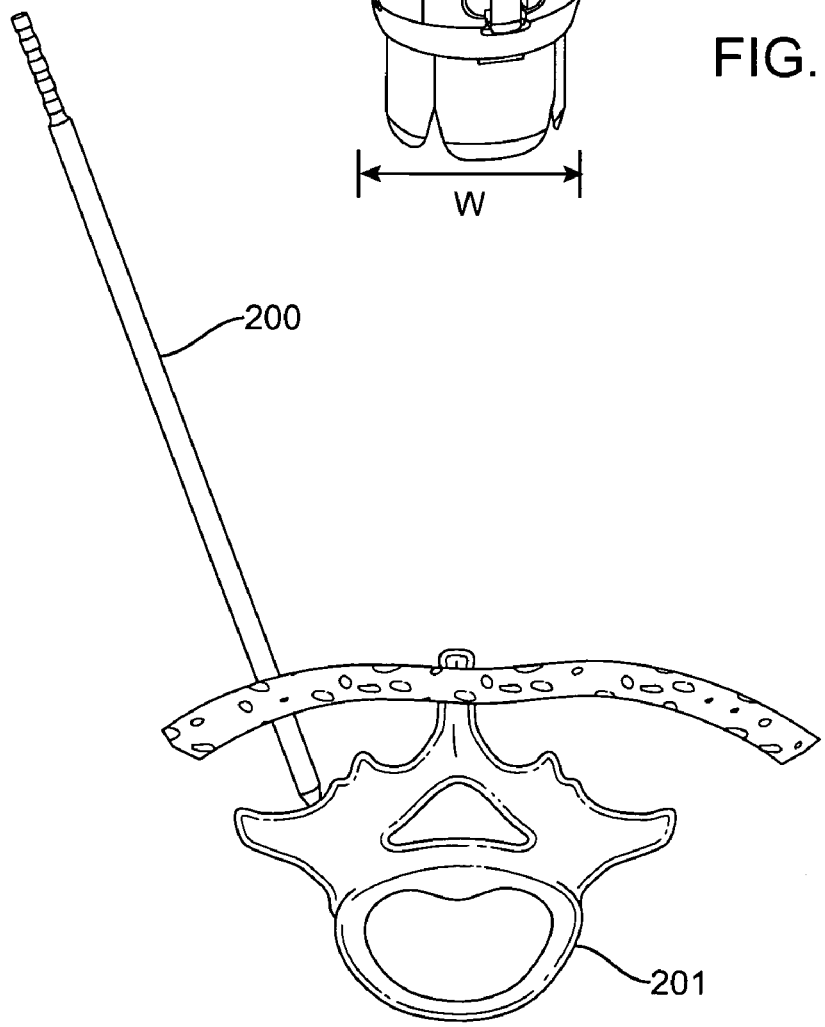
FIG. 15 illustrates a first dilator inserted to a patient's spine.
Figure 16:
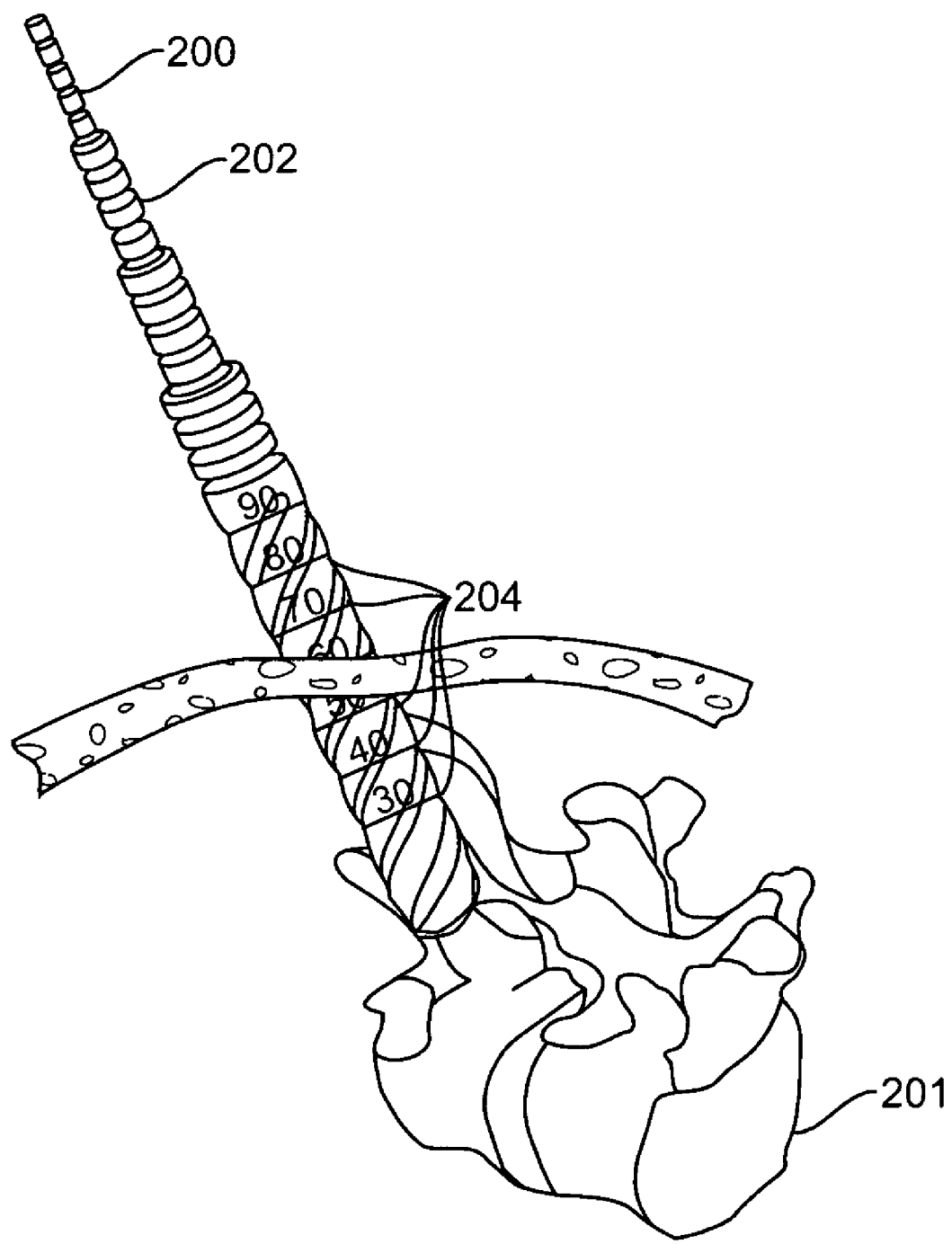
FIG. 16 illustrates a sequentially-dilated incision with access to a patient's spine.
Figure 17A:
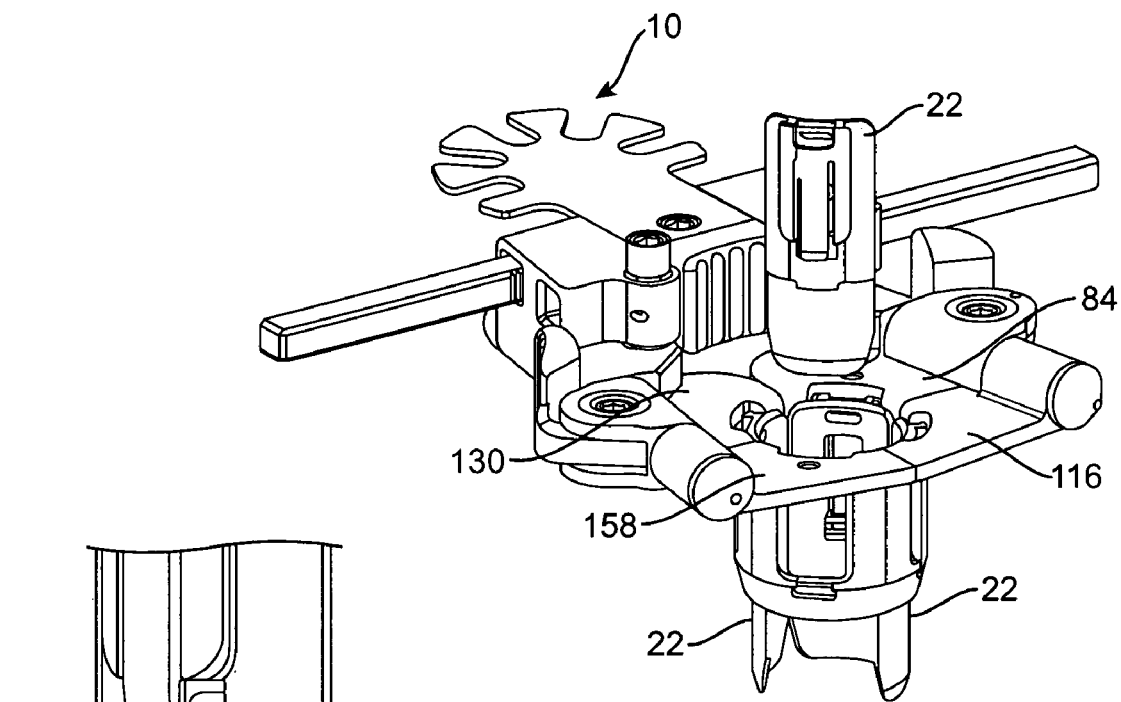
FIG. 17a illustrates a perspective view of a retractor blade in juxtaposition to a retractor according to the present invention.
Figure 17B:
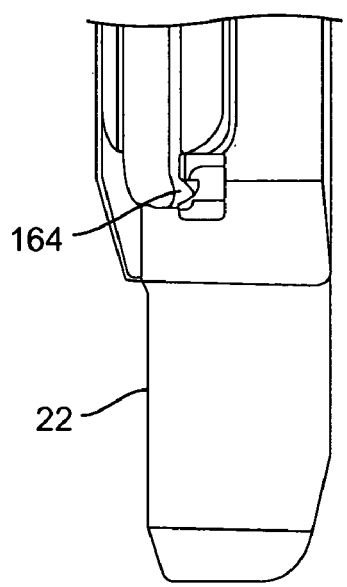
FIG. 17b illustrates a partial perspective view of a retractor blade hooked to a blade support according to the present invention.
Figure 17C:
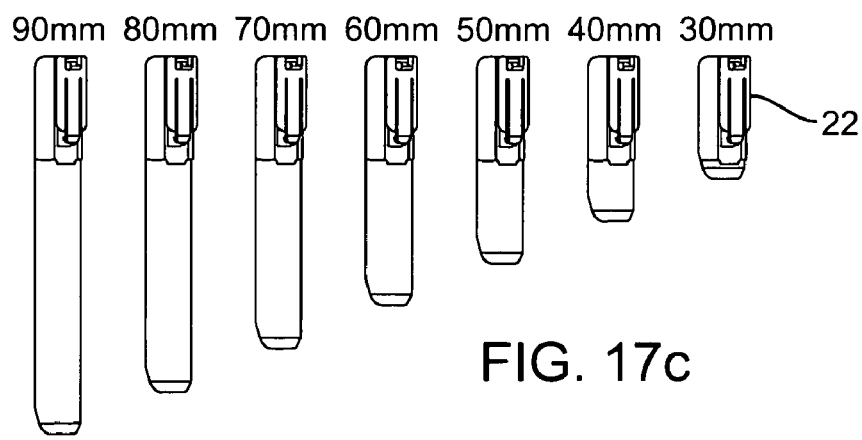
FIG. 17c illustrates retractor blades of various lengths according to the present invention.

Referring now to FIG. 15, a first dilator 200 is inserted into the incision and advanced through the fascia and muscle tissue. Placement of the first dilator 200 is confirmed with fluoroscopy and by palpating the bony anatomy 201. Additional dilators two-through-four 202 are placed sequentially by passing the next largest dilator over the previously inserted dilator as shown in FIG. 16. If resistance is met, a scalpel is used to further incise the skin and fascia. Retractor blade length is selected by measuring the tissue depth from the etch markings 204 on the last dilator as shown in FIG. 16. The tissue depth read from the etch markings 204 directly corresponds to the suggested retractor blade length for use with the retractor 10. The selected blades are inserted into the four blade supports 84, 116, 130, 158 as shown in FIG. 17*a*. When a blade 22 is fully seated within a blade support there is an audible and tactile "click". Also, when the blade 22 is fully engaged with the blade supports, the hook 164 of the retractor blade 22 is clipped over the blade support as shown in FIG. 17*b*. Various retractor blades 22 of different lengths are shown in FIG. 17*c* ranging from approximately 30 mm to 120 mm. Each length being coded to a different retractor blade color for ease of selection and installation into the retractor 10.

Figure 18A:
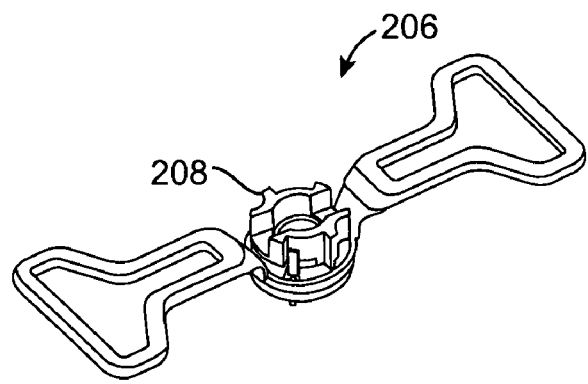
FIG. 18a illustrates a perspective view of a retractor inserter according to the present invention.
Figure 18B:
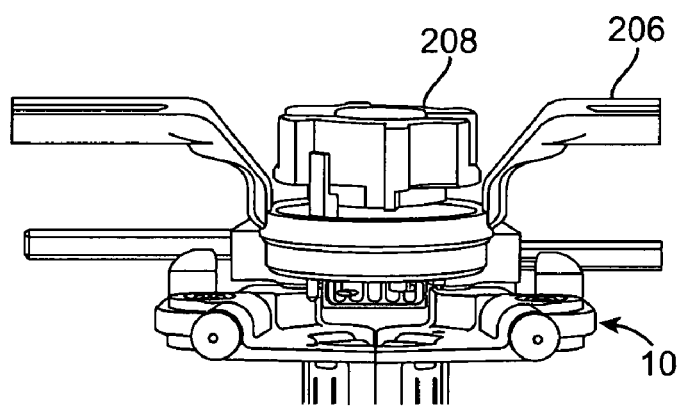
FIG. 18b illustrates a side view of a retractor inserter connected to a retractor according to the present invention.
Figure 18C:
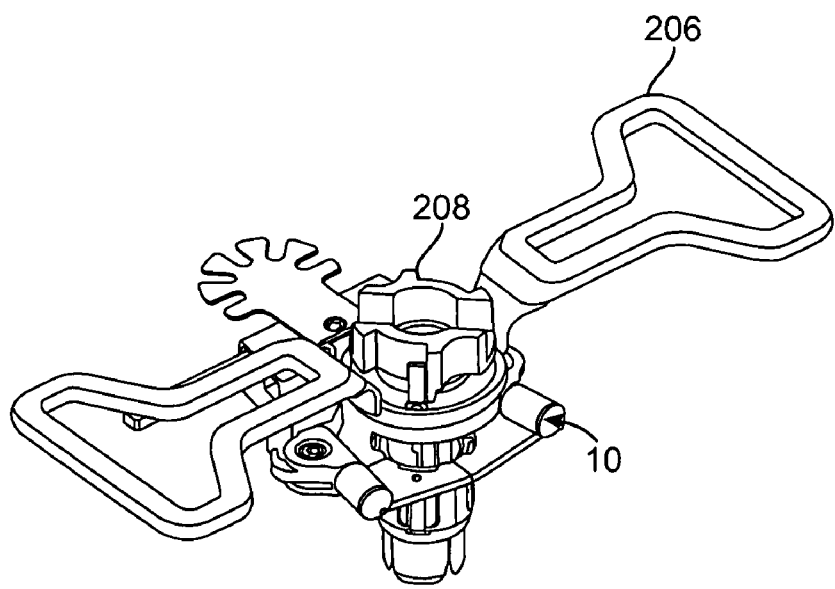
FIG. 18c illustrates a top perspective view of a retractor inserter connected to a retractor according to the present invention.

Turning now to FIG. 18*a*, to facilitate placement, a retractor inserter 206 having a knob 208 is provided. The knob 208 is oriented into an unlocked position and the retractor inserter 206 is placed over the retractor 10 aligning the holes on the retractor with the holes on the inserter as shown in FIGS. 18*b* and 18*c*. To secure the inserter onto the retractor, the knob is turned clockwise until a mechanical stop is reached and the etch markings on the inserter indicate the locked position.

Figure 19A:
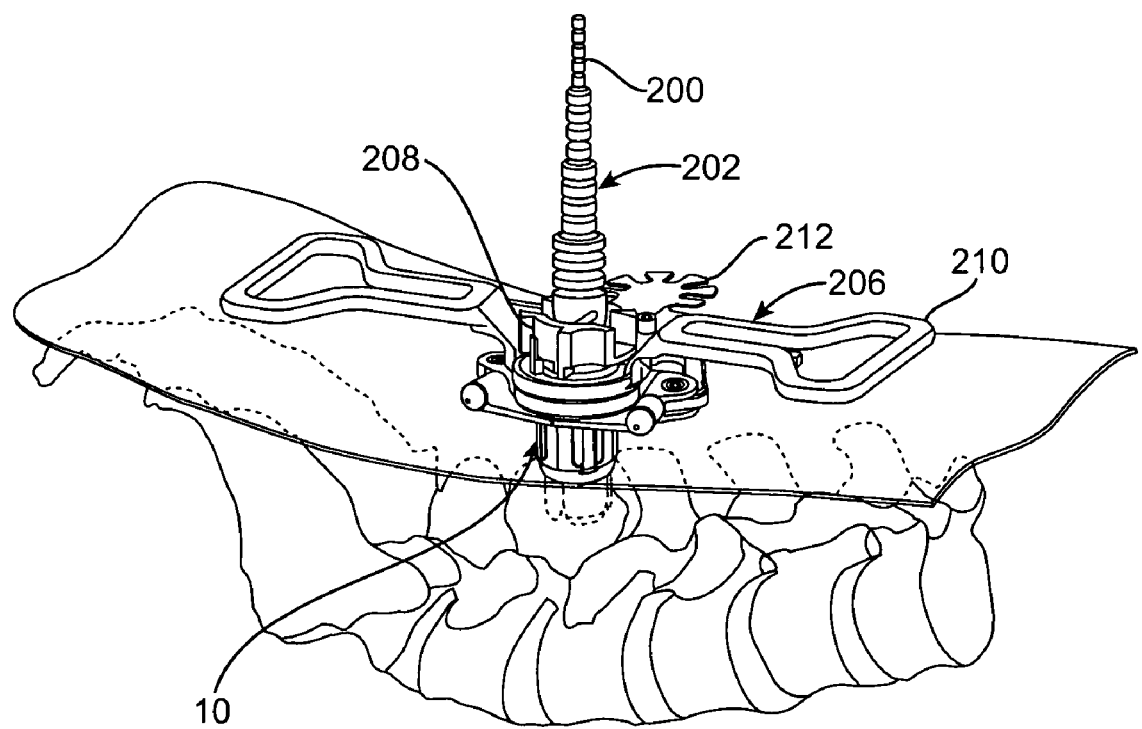
FIG. 19a illustrates dilators, a retractor and retractor inserter placed in a spinal surgical opening according to the present invention.
Figure 19B:
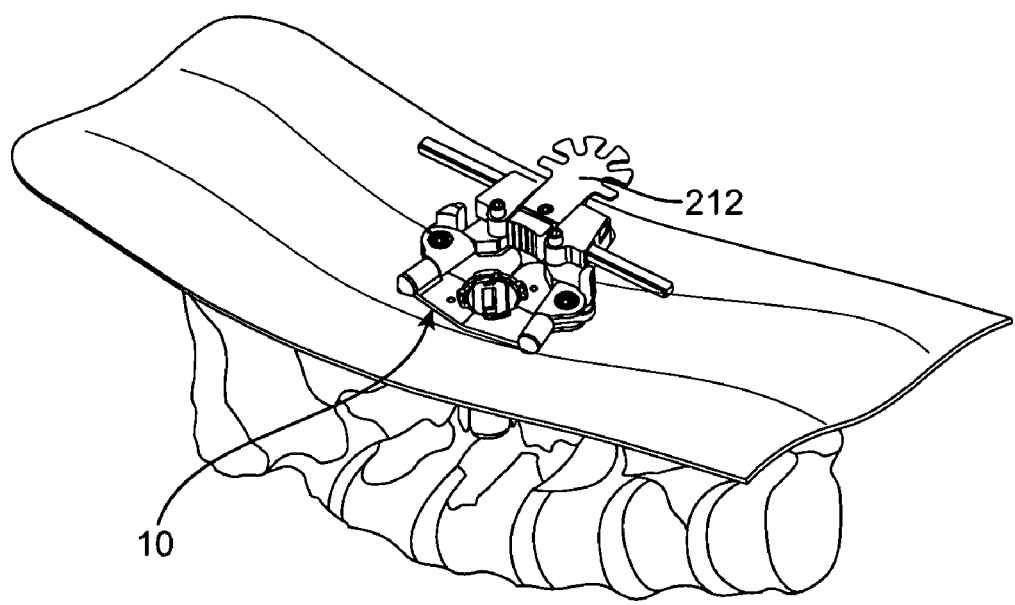
FIG. 19b illustrates the retractor placed in a spinal surgical opening according to the present invention.

Turning now to FIGS. 19*a* and 19*b*, retractor placement is shown. With the dilators 200, 202 in place in the patient and the retractor 10 connected to the inserter 206, the handles 210 of the retractor inserter 206 are used to toggle the retractor 10 through the tissue opening the dilators 200, 202 into position over the bony anatomy with the fanned support base 212 positioned next to the midline. After placement of the retractor 10 is confirmed with fluoroscopy, the dilators 200, 202 are removed and the retractor inserter 206 is disengaged by turning the knob 208 counterclockwise to the unlocked position and pulling it upwardly to remove the retractor inserter 206. The retractor 10 is secured to a rigid arm (not shown) at the fanned support base 212 which accommodates both flat and pin style clamps.

Turning now to FIGS. 20*a*, 20*b* and 20*c*, translation of the retractor 10 will now be discussed. A T-shaped handle hex driver 214 is inserted into the hex socket of the middle pinion 34 as shown in FIG. 20*a*. When the pinion 34 is rotated, the retractor 10 expands from the configuration shown in FIG. 20*a* into the configuration shown in FIG. 20*b*. The maximum cephalad-caudal span is shown by the distance C in FIG. 20*c*. C is any dimension in the range of 5.0 and 20 centimeters. In one variation, C is approximately 8 centimeters. Although dimension C is called a cephalad-caudal span, the invention is not so limited as the retractor can be oriented in a number of other orientations with respect to patient anatomy and the dimension is not limited thereby. Distance C is the distance of maximum expansion attainable between the right and left assemblies 18, 20.

Turning now to FIGS. 21*a* and 21*b*, for medial-lateral translation, or upper-to-lower translation, the hex driver 214 is inserted into one or more of the two hex sockets of pinions 94, 140 as shown in FIG. 21*a*. Each click with turning of the hex driver expands the lower right and left blade support assemblies 78, 122 outwardly in the medial-lateral direction by approximately 1.0 mm and up to a maximum span L in the range of between approximately 2.0 centimeters and approximately 10.0 centimeters and in one variation approximately 4.5 centimeters as shown in FIG. 21*b*. The hex driver 214 can be switched back and forth between hex sockets of pinions 34, 94 and 140 expanding a few millimeters each time until the optimal working channel is achieved according to surgeon preference. Of course, although dimension L is referred to as the medial-lateral translation distance, the invention is not limited to the orientation of the instrument with respect to the patient anatomy. The distance L is the distance between the upper and lower units of the right and left assemblies 18, 20.

Figure 22B:
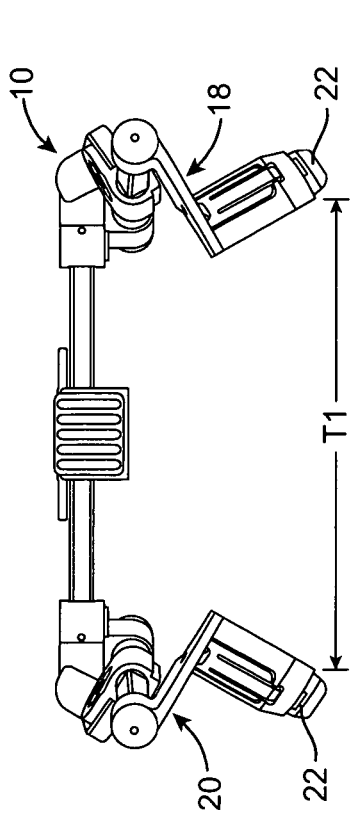
FIG. 22b illustrates front view of a retractor with the right and left assemblies angled outwardly to a distance T1 according to the present invention.
Figure 22C:
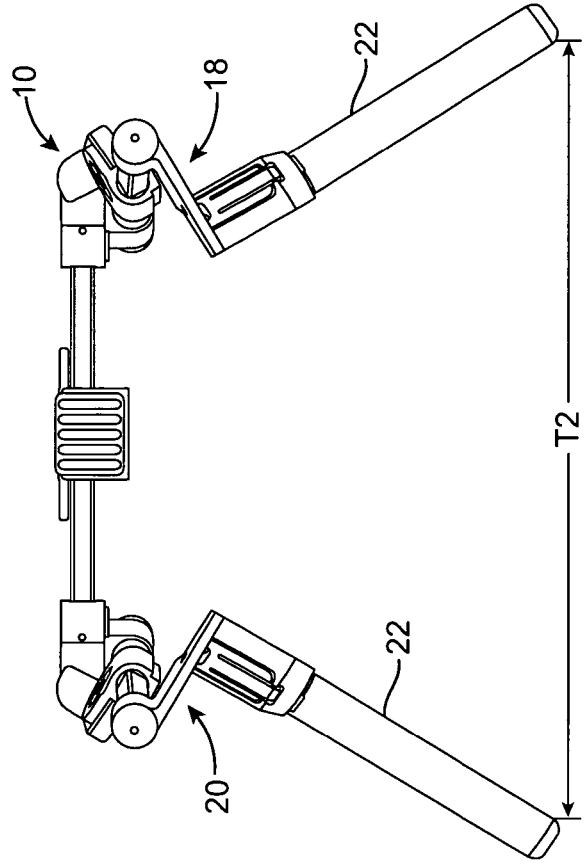
FIG. 22c illustrates a front view of a retractor with the right and left assemblies angled outwardly to a distance T2 according to the present invention.
Figure 22A:
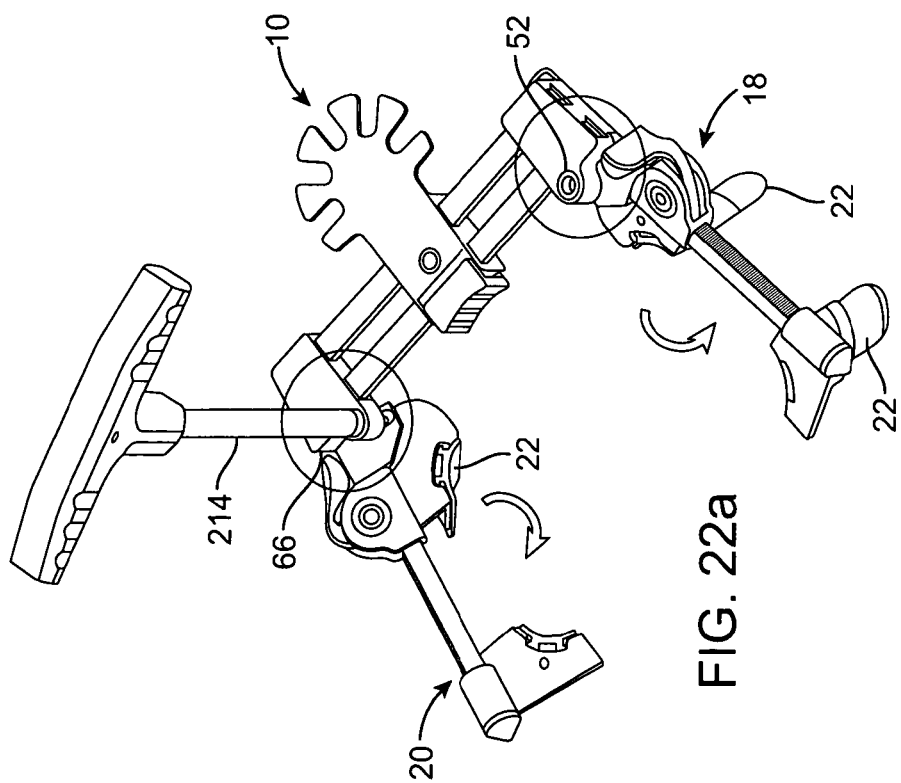
FIG. 22a illustrates a perspective view of a T-shaped driver connected to a tow angle post of an upper left rack assembly of the retractor with the right and left assemblies angled outwardly according to the present invention.

Turning now to FIGS. 22a, 22b and 22c, angulation of the retractor blades 22 is shown. To angle the retractor blades 22, the hex driver 214 is inserted into the one or more of the two hex sockets of the tow angle posts 52, 66. Turning the right tow angle post 52 angles the blades of the right assembly 18 and turning the left tow angle post 66 angles the blades of the left assembly 20. The blades 22 angle up to a maximum of approximately 30 degrees in one variation. Maximum anglation is between approximately 5 and 80 degrees. The size of the opening at the distal end of the blades depends upon blade length. If blades 22 of a first length are employed, the maximum distal span is distance T1 which for a 30 millimeter long blade is approximately 11 centimeters as shown in FIG. 22b. If blades of a second length are employed, the maximum distal span is distance T2 which for a 90 millimeter long blade is approximately 17 centimeters as shown in FIG. 22c. A table of approximate maximum distal spans corresponding to certain blade lengths is shown in FIG. 23.

Figure 24A:
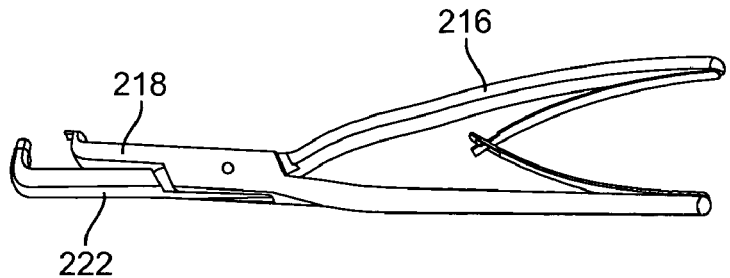
FIG. 24a illustrates a perspective view of a blade removal tool according to the present invention.
Figure 24B:
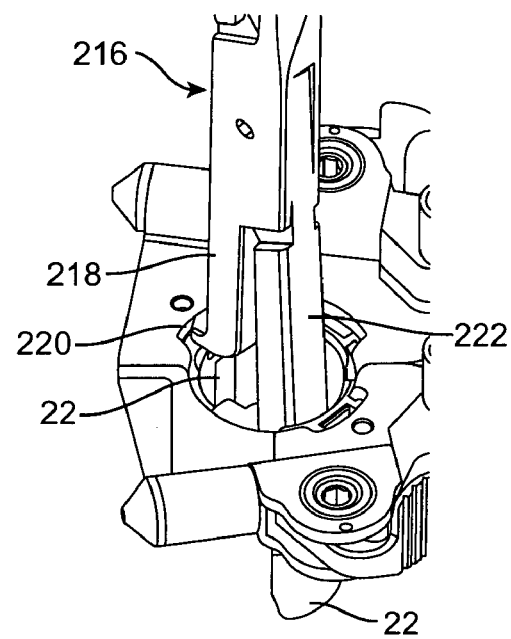
FIG. 24b illustrates a perspective view of a blade removal tool engaged with a blade in a retractor according to the present invention.
Figure 24C:
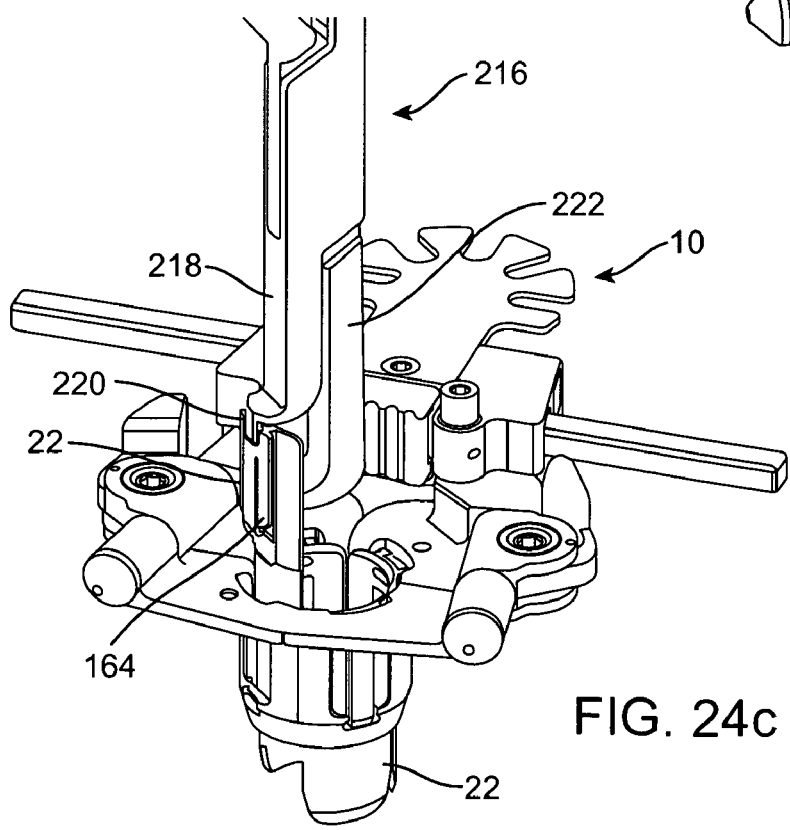
FIG. 24c illustrates a perspective view of a blade removal tool removing a blade from a retractor according to the present invention.

Turning now to FIGS. 24a, 24b and 24c, blade removal will now be described. If a smaller or larger blade length is required after the retractor has been placed inside the patient, a blade removal tool 216 is employed. The blade 22 to be removed is first identified and then the blade removal tool 216 is held in one hand and aligned such that the proximal leg 218 of the tool 216 is in line with the corresponding slot 220 on top of the blade 22 as shown in FIG. 24b. The blade removal tool 216 is pushed down into the slot 220 and then the handles of the blade removal tool 216 are squeezed together to release the blade 22. When the handles are squeezed, the proximal leg 218 of the tool contacts the blade 22 while the distal leg 222 of the tool depresses the hook 164 on the blade 22 deflecting it to release the blade from the retractor 10 as the tool is pulled up as shown in FIG. 24c.

Figure 25B:
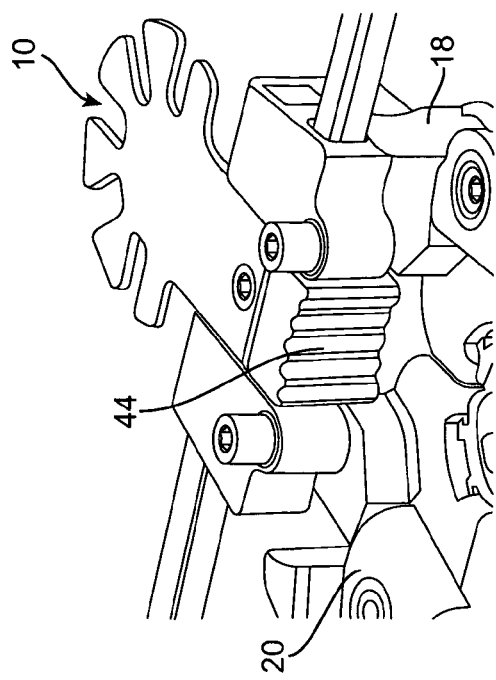
FIG. 25b illustrates a partial perspective view of a retractor illustrating the release body according to the present invention.
Figure 25C:
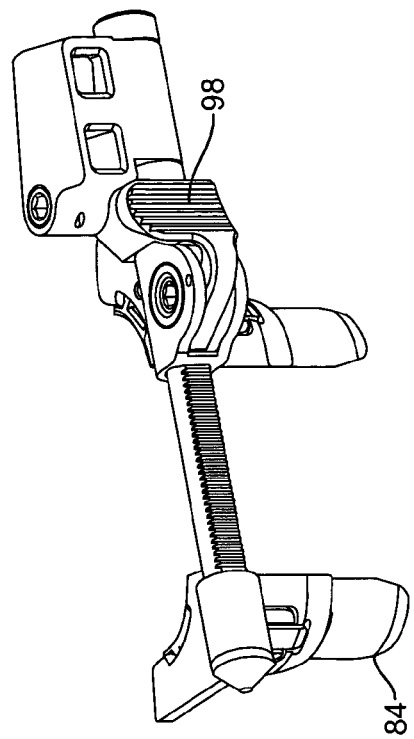
FIG. 25c illustrates a partial perspective view of a retractor illustrating the gear lock of the right upper and lower blade supports according to the present invention.
Figure 25A:
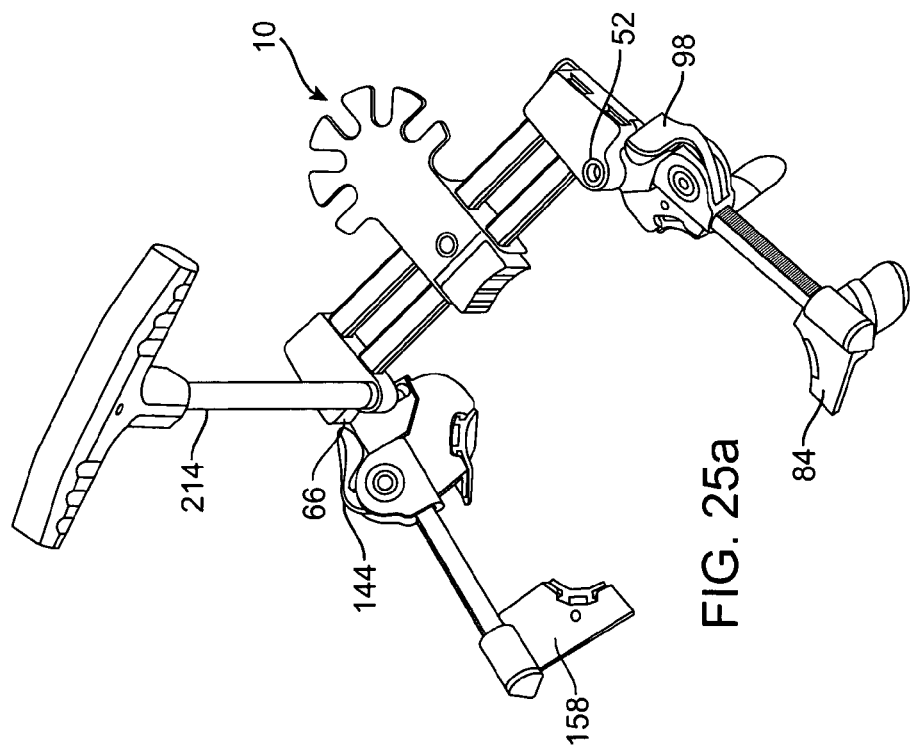
FIG. 25a illustrates a perspective view of a T-shaped driver connected to a tow angle post of an upper left rack assembly of the retractor with the right and left assemblies angled outwardly according to the present invention.

Turning now to FIGS. 25a, 25b and 25c, removal of the retractor 10 will now be described. To remove the retractor 10 from the patient, any of the blades that are angled are reset to zero degrees by turning the one or more of the two hex sockets of the tow angle posts 52, 66 with the hex driver 214 as shown in FIG. 25a. To retract the extended right and left assemblies 18, 20, the release body 44 is depressed as shown in FIG. 25b effecting cephalad-caudal release. To retract the extended lower right blade support 84, the gear lock 98 is depressed as shown in FIG. 25c effecting medial-lateral release of the right side. With reference back to FIG. 25a, to retract the extended lower left blade support 158, the gear lock 144 is depressed effecting medial lateral release of the left side.

Figure 26A:
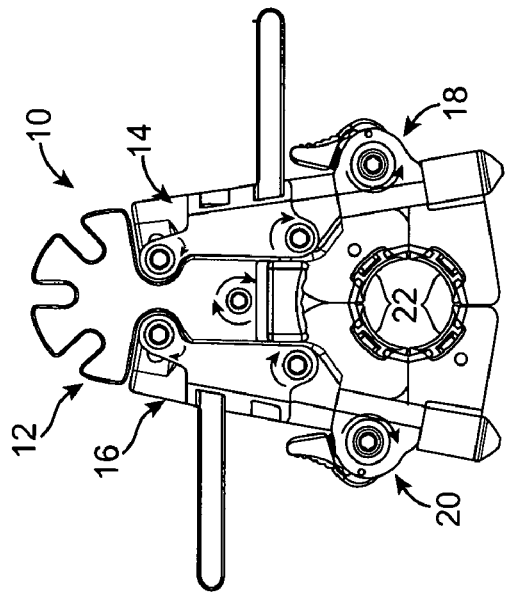
FIGS. 26a-26c illustrate various views of the retractor according to the present invention.
Figure 26B:
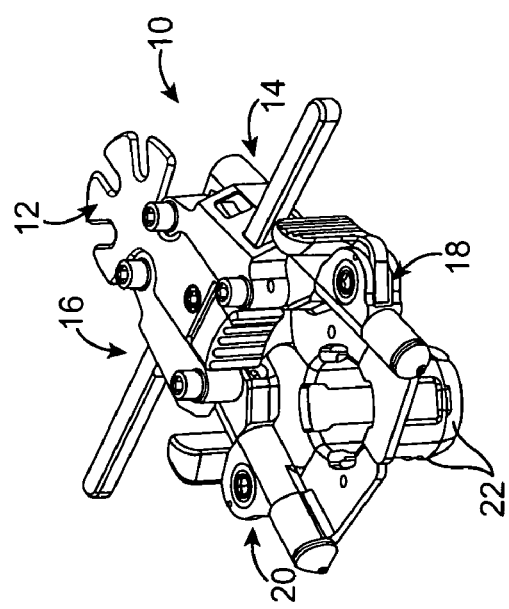

Turning now to FIGS. 26a and 26b, there is shown another variation of the retractor according to the present invention. Like reference numbers will be used to describe like parts with respect to this variation of the retractor. The retractor 10 includes a middle assembly 12, an upper right rack assembly 14, an upper left rack assembly 16, a right assembly 18, a left assembly 20 and blades 22. The upper right and left rack assemblies 14, 16 are connected to the middle assembly 12. Blades 22 are connected to the right and left assemblies 18, 20. The right and left assemblies 18, 20 are connected to the upper right and left rack assemblies 14, 16, respectively.

Figure 27A:
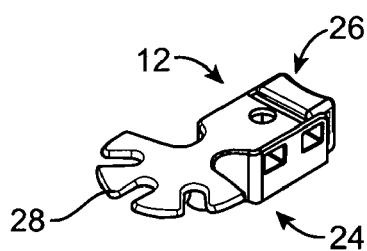
FIGS. 27a-27d illustrate the middle assembly of the retractor according to the present invention.
Figure 27B:
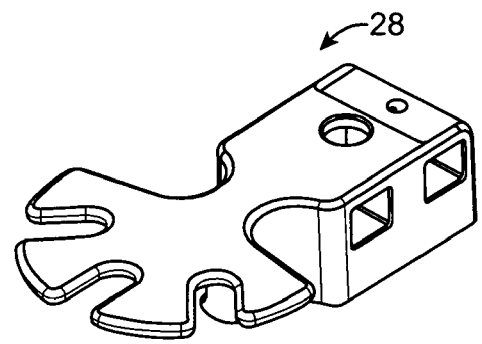
Figure 27C:
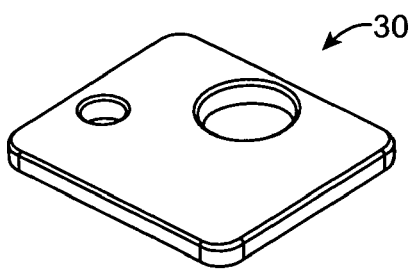
Figure 27D:
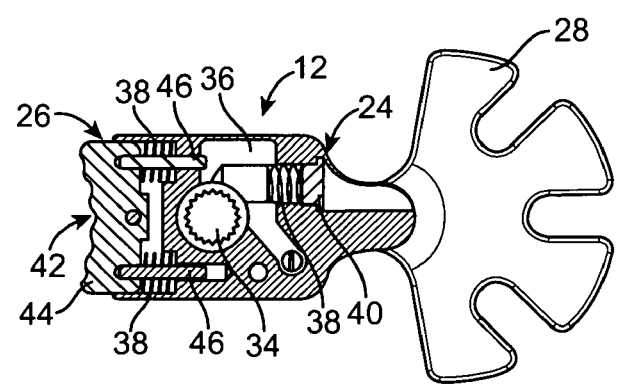

Referring now to FIGS. 27a, 27b, 27c, and 27d, the middle assembly 12 includes a main body assembly 24 and a main body sub-assembly 26. The main body assembly 24 includes a main body 28 (shown in FIGS. 27a and 27b) and cover 30 (shown in FIG. 27c) with fastener. The main body assembly 24 houses the main body sub-assembly 26 as shown in FIG. 27d. The main body includes a main body plane which is coincident with the plane of the paper in which FIG. 26b is drawn.

Referring particular reference now to FIG. 27a, the components of the main body sub-assembly 26 will now be described. The main body sub-assembly 26 includes a middle pinion 34 (of a type shown in FIG. 4b), a middle pinion lock 36 (of a type shown in FIG. 4c), springs 38 (one shown in FIG. 4d), a spring cap 40 (of a type shown in FIG. 4e), and a middle housing release assembly 42 (shown in FIGS. 4f, 4g, and 4h). The middle housing release assembly 42 includes a release body 44 and pins 46 connected thereto as also shown in FIGS. 4f and 4g. The main body sub-assembly 26 is substantially the same as that described above with respect to FIGS. 4a-4h. Also, the assembly of the main body sub-assembly 26 inside the main body 28 is substantially the same as described above with respect to FIGS. 4a-4h and will now be described. The middle pinion 34 is disposed inside the main body 28 and the middle pinion lock 36 is configured to engage the middle pinion 34. The middle pinion lock 36 is biased by a spring 38 which is held in position by the spring cap 40 inside the main body 28. The lock 36 permits rotation of the middle pinion 34 in one direction locking it from rotation in an opposite direction. The middle housing release assembly 42 is connected to the main body assembly 24 and configured such that two springs 38 bias the release body 44 outwardly and such one of the pins 46 engage the lock 36 when the release body 44 is depressed to thereby unlock the middle pinion 34 allowing it to rotate in the opposite direction. The cover 30 and fasteners are used to contain the main body sub-assembly 26 inside the main body assembly 24.

Figure 28A:
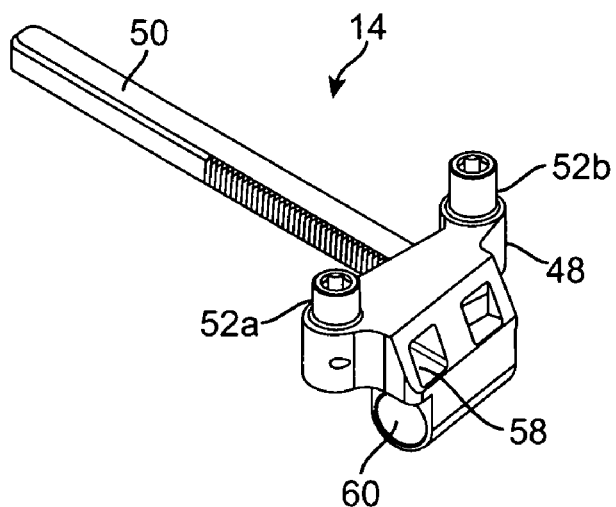
FIGS. 28a-28d illustrate the upper right rack assembly of the retractor according to the present invention.
Figure 28B:
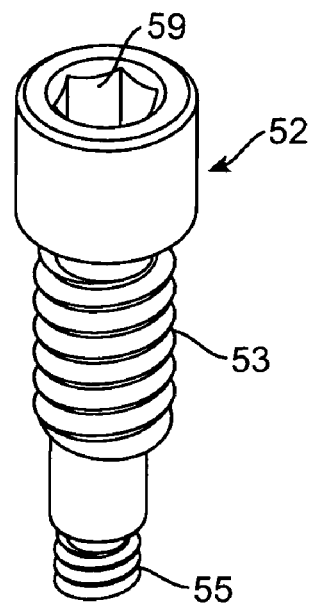
Figure 28C:
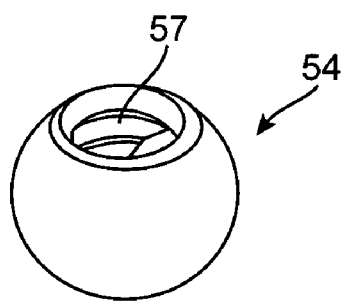
Figure 28D:
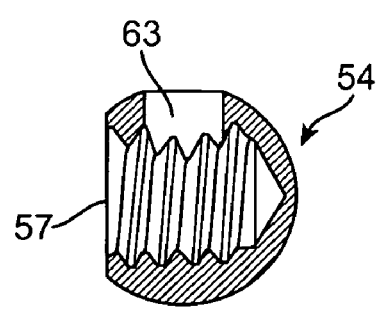

Referring now to FIGS. 28a, 28b, 28c and 28d, the upper right rack assembly 14 will now be described. The upper right rack assembly 14 includes a rack support 48, a straight rack 50, a first tow angle post 52a, a second tow angle post 52b (wherein the first and second tow angle post are the same and shown in FIG. 28b) and tow angle return 54 connected to each of the tow angle posts 52a, 52b. A tow angle return 54 is shown in FIG. 28c. The straight rack 50 is inserted into the rack support 48 and connected by a pin (not shown). As shown in FIG. 28a, the rack support 48 includes a passageway 58 for receiving a straight rack 50 of the upper left rack assembly 16. The rack support 48 also includes a second passageway 60 for receiving and connecting to the right assembly 18. The first and second tow angle posts are inserted into respective threaded apertures in the rack support 48 and threadingly connected thereto. The tow angle post 52 includes a hex socket 59 and a first threaded portion 53 and a second threaded portion 55 as shown in FIG. 28b. The first threaded portion 53 connects with the rack support 48 and the second threaded portion 55 connects with the threaded portion 57 (FIGS. 28c and 28d) on the tow angle return 54. The tow angle return 54 includes an access portal 63 (shown in FIG. 28d) for delivery and assembly of the tow angle return, holding it in place as it is threaded to the tow angle post, and injecting weld material or adhesive to connect the tow angle post to the tow angle return. The tow angle return 54 is threaded onto to the distal end of the tow angle post 52 at the second threaded portion 55. As such, the first tow angle post 52a and the tow angle return 54 are configured to capture a first portion of the right assembly 18 therebetween to control the angulation and rotation of said first portion of the right assembly 18 with respect to the upper right rack assembly 14. The second tow angle post 52b and tow angle return 54 are connected and configured to capture a second portion of the right assembly 18 as will be described in greater detail below.

Turning now to FIG. 29, the upper left rack assembly 16 will now be described. The upper left rack assembly 16 includes a rack support 62, a straight rack 64, a first tow angle post 66a, a second tow angle post 66b, and a tow angle return of the type shown in FIGS. 28b and 28c connected to each of the tow angle posts 66a, 66b. The straight rack 64 is inserted into the rack support 62 and connected by a pin (not shown). The rack support 62 includes a passageway 72 for receiving the straight rack 50 of the upper right rack assembly 14. The rack support 62 also includes a second passageway 74 for receiving and connecting to the left assembly 20. The first and second tow angle posts are inserted into respective threaded apertures in the rack support 62 and threadingly connected thereto. The tow angle returns are inserted into and threadingly connected to the distal ends of the tow angle posts 66a and 66b similarly as described above with respect the upper right rack assembly 14. As such, the first tow angle post 66a and the tow angle return are configured to capture a first portion of the left assembly 20 therebetween to control the angulation and rotation of said first portion of the left assembly 20 with respect to the upper left rack assembly 16. The second tow angle post 66b and the tow angle return are configured to capture a second portion of the left assembly 20 therebetween to control the angulation and rotation of said second portion of the left assembly 20 as will be described in greater detail below.

Turning now to FIGS. 30a, 30b, 30c and 30d, the upper right track assembly 14 is shown connected to the right assembly 18. The right assembly 18 will now be described. The right assembly 18 includes an upper right blade support assembly 76 connected to a lower right blade support assembly 78.

Figure 31A:
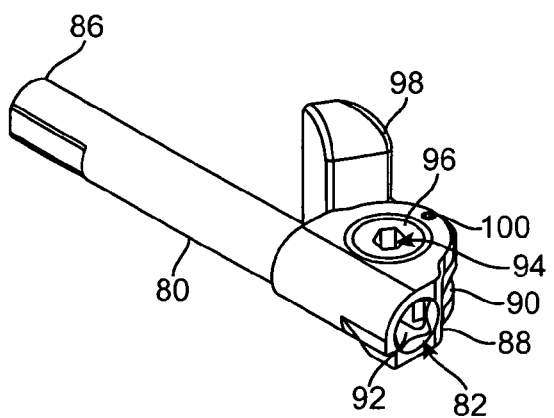
FIGS. 31a-31c illustrate the upper right blade support assembly of the retractor according to the present invention.
Figure 31B:
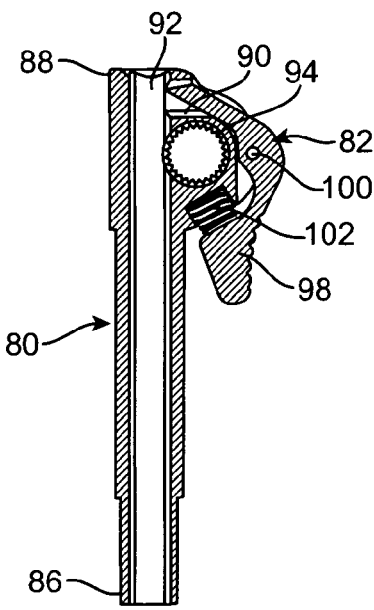
Figure 31C:
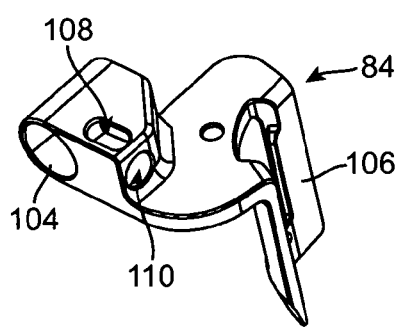

Turning now to FIGS. 31a, 31b, and 31c the upper right blade support assembly 76 will now be described. The upper right blade support assembly 76 includes a mounting arm 80 (FIGS. 31a and 31b) connected to a mounting arm sub-assembly 82 (FIGS. 31a and 31b) and blade support 84 (FIG. 31c).

Turning now to FIGS. 31a and 31b, there is shown a mounting arm 80 according to the present invention. The mounting arm 80 includes a longitudinal axis, a proximal end 86, a distal end 88, a mounting arm sub-assembly receiving portion 90 located near the distal end 88 and a central bore 92 extending between the proximal end 86 and distal end 88. The mounting arm 80 is configured to be received within passageway 60 of the upper right rack assembly 14 and connected thereto.

Still referencing FIGS. 31a and 31b, the mounting arm sub-assembly 82 will now be described. The mounting arm sub-assembly 82 includes a pinion 94 (of the type shown in FIG. 8d), retaining collar 96 (shown in FIG. 8e), gear lock 98 (also shown in FIG. 8f), and a pin 100 (shown in FIG. 8g). The pinion 94 is disposed inside the mounting arm 80 and retained therein with the retaining collar 96. The gear lock 98 is connected to the mounting arm 80 via pin 100 and configured for contact with a ratcheting pin (not shown) and in turn with the pinion 94. A spring 102 is employed to bias the gear lock 98 against a ratcheting pin (not shown) in the central bore 92 to lock the ratcheting pin and pinion 94 in position. The gear lock 98 is configured such that pinion which is interconnected to the ratcheting pin via teeth is allowed to rotate in one direction locking it from rotation in an opposite direction in a manner such that incremental extension of the ratcheting pin is locked in place with turning of the pinion 94. The gear lock 98 can be depressed to thereby unlock the pinion 94 allowing it to rotate in the opposite direction thereby permitting retraction of the ratcheting pin.

Turning now to FIG. 31c, there is shown the blade support 84 according to the present invention. The blade support 84 includes a mounting arm receiving portion 104, a blade flange 106 configured for attachment to a blade 22, a tow angle post receiving portion 108 and a tow angle return receiving portion 110, both the tow angle post receiving portion 108 and the tow angle return receiving portion 110 are interconnected.

The mounting arm 80 is inserted into the mounting arm receiving portion 104 and the mounting arm 80 is inserted into the second passageway 60 of the upper right rack assembly 14. The threaded proximal end 86 is capped with an internally threaded end cap 112 like the one shown in FIG. 8k. The mounting arm 80 is oriented and the first tow angle post 52a is inserted into the first tow angle post receiving portion 108. The tow angle return 54 is inserted into the tow angle return receiving portion 110 and threaded onto the first tow angle post 52a and connected thereto with adhesive or welding material injected through the tow angle return access portal 63 capturing the blade support 84 therebetween as shown in FIG. 30b.

Figure 26C:
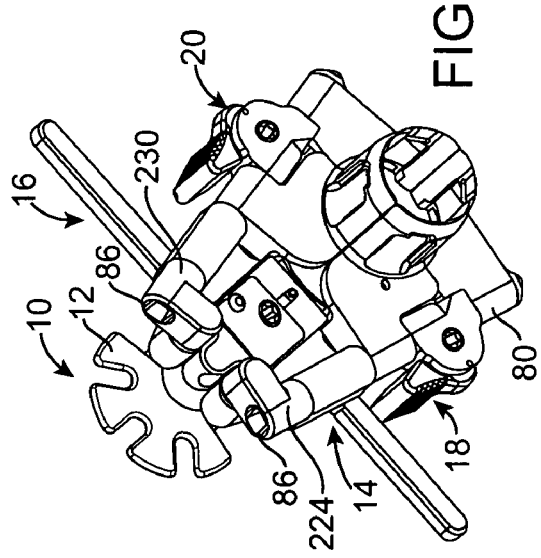
Figure 32:
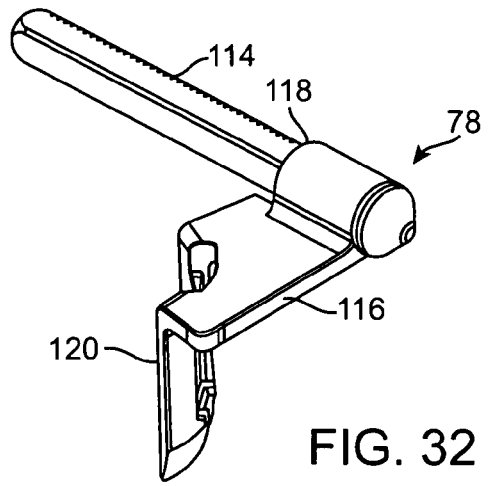
FIG. 32 illustrates the lower right blade support assembly of the retractor according to the present invention.

Turning now to FIG. 32, there is shown the lower right blade support assembly 78. The lower right blade support assembly 78 includes a toothed ratcheting pin 114 connected to a lower right blade support 116. The lower right blade support includes a ratcheting pin receiving portion 118 connected to a blade flange 120 configured for attachment to a blade 22. The ratcheting pin 114 is inserted into the ratcheting pin receiving portion 118, one end of which includes a stop and the other end being inserted into the central bore 92 of the mounting arm 80 such that the toothed ratcheting pin 114 engages the teeth of the pinion 94 and is permitted to slide with respect to the upper right blade support assembly 76 upon turning of the pinion 94. A second tow angle post 52b is inserted into a second tow angle post receiving portion 232 of a first end piece 224 and threaded to the second tow angle post return inserted through a tow angle post receiving portion 234 of the first end piece 224 (shown in FIG. 30d) and connected thereto with adhesive or welding material injected through the tow angle return access portal 63 capturing the first end piece 224 therebetween as shown in FIGS. 26c and 30c.

Figure 33C:
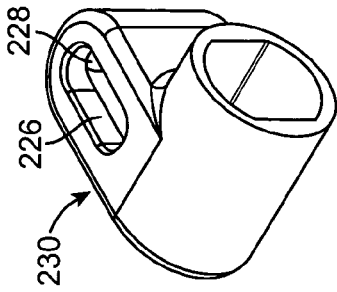
FIGS. 33a-33c illustrate the various views of the upper left track assembly connected to the left assembly of the retractor according to the present invention.
Figure 33D:
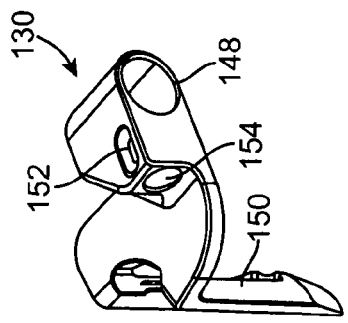
FIG. 33d illustrates a second end piece of the retractor according to the present invention.
Figure 33B:
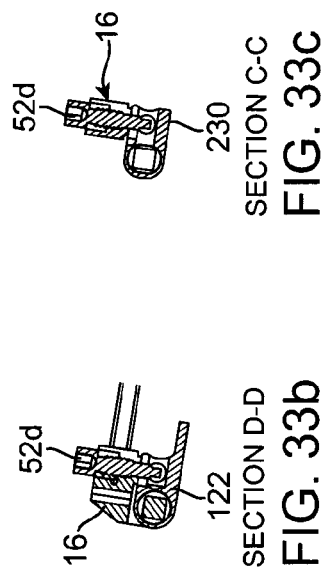
Figure 33A:
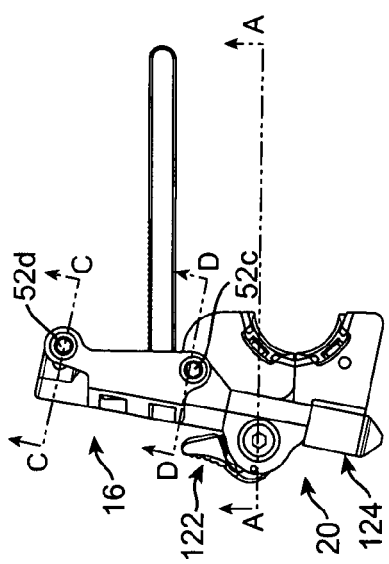

Turning now to FIGS. 33a, 33b and 33c, the upper left track assembly 16 is shown connected to the left assembly 20. The left assembly 20 will now be described. The left assembly 20 includes an upper left blade support assembly 122 connected to a lower left blade support assembly 124.

Figure 34B:
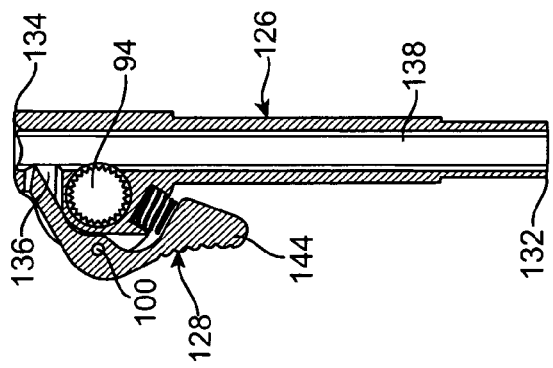
Figure 34A:
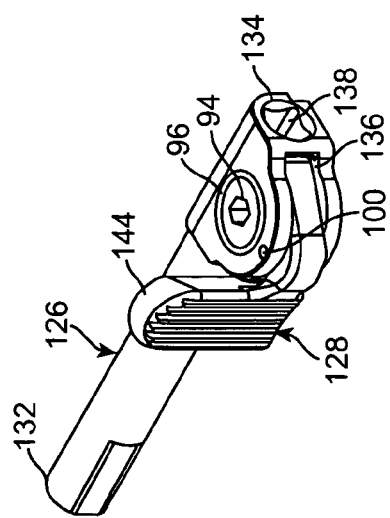

Turning now to FIGS. 34a, 34b, and 34c, the upper left blade support assembly 122 will now be described. The upper left blade support assembly 122 includes a mounting arm 126 (FIGS. 34a and 34b) connected to a mounting arm sub-assembly 128 (FIGS. 34a and 34b) and blade support 130 (FIG. 34c).

Turning now to FIGS. 34a and 34c, the mounting arm 126 will now be described. The mounting arm 126 includes a longitudinal axis, a proximal end 132, a distal end 134, a mounting arm sub-assembly receiving portion 136 located near the distal end 134 and a central bore 138 extending between the proximal end 132 and distal end 134. The mounting arm 126 is configured to be received within second passageway 74 of the upper left rack assembly 16 and connected thereto.

Still referencing FIGS. 34a and 34b, the mounting arm sub-assembly 128 will now be described. The mounting arm sub-assembly 128 includes a pinion 94 (shown in FIG. 8d), retaining collar 96 (shown in FIG. 8e), gear lock 144 (shown in FIG. 11d), and a pin 100 (shown in FIG. 8g). The pinion 94 is disposed inside the mounting arm 126 and retained therein with the retaining collar 96. The gear lock 144 is connected to the mounting arm 126 via a pin 100 and configured for contact with the pinion 94 via a ratcheting pin (not shown). A spring 102 is employed to bias the gear lock 144 against a ratcheting pin (not shown) in the central bore 138 to lock the ratcheting pin and the pinion in position. The gear lock 144 is configured such that the pinion is allowed to rotate in one direction locking it from rotation in an opposite direction in a manner such that incremental extension of the ratcheting pin is locked in place with turning of the pinion. The gear lock 144 can be depressed to thereby unlock the pinion allowing it to rotate in the opposite direction thereby permitting retraction of the ratcheting pin.

Turning now to FIG. 31c, there is shown the blade support 130 according to the present invention. The blade support 130 includes a mounting arm receiving portion 148, a blade flange 150 configured for attachment to a blade 22, a tow angle post receiving portion 152 and a tow angle return receiving portion 154, both the tow angle post receiving portion 152 and the tow angle return receiving portion 154 comprising interconnected bores through the blade support 130.

The mounting arm 126 is inserted into the mounting arm receiving portion 148 and the mounting arm 126 is inserted into the second passageway 74 of the upper left rack assembly 16. The threaded proximal end 132 is capped with an internally threaded end cap of the like shown in FIG. 8k. The mounting arm 126 is oriented and a third tow angle post 52c is inserted into the tow angle post receiving portion 152. The tow angle return is inserted into the tow angle return receiving portion 154 and threaded into the tow angle post capturing the blade support 130 therebetween as shown in FIG. 33b.

Figure 35:
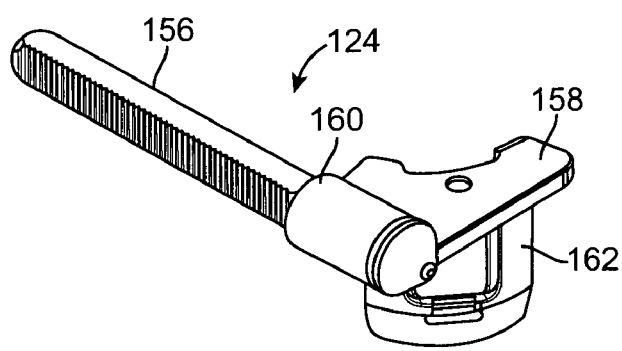
FIG. 35 illustrates the lower left blade support assembly of the retractor according to the present invention.

Turning now to FIG. 35, there is shown the lower left blade support assembly 124. The lower left blade support assembly 124 includes a toothed ratcheting pin 156 connected to a lower left blade support 158. The lower left blade support 158 includes a ratcheting pin receiving portion 160 connected to a blade flange 162 configured for attachment to a blade 22. The ratcheting pin 156 is inserted into the ratcheting pin receiving portion 160, one end of ratcheting pin 156 including a stop and the other end being inserted into the central bore 138 of the mounting arm 126 such that the toothed ratcheting pin 156 engages the teeth of the pinion and is permitted to slide with respect to the upper left blade support assembly 122 upon turning of the pinion 94. A fourth tow angle post 52d is inserted into a fourth tow angle post receiving portion 226 of a second end piece 230 and threaded to a third to a tow angle post return inserted through a tow angle post return receiving portion 228 (shown in FIG. 33d) and connected thereto with adhesive or welding material injected through the tow angle return access portal capturing the end piece 230 therebetween as shown in FIGS. 26c and 33c.

As seen in the figures, the left assembly 20 is a mirror image of the right assembly 18.

Figure 36A:
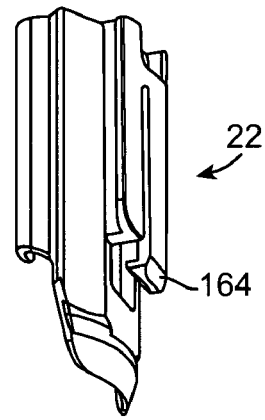
FIGS. 36a-36b illustrate a blade of the retractor according to the present invention.
Figure 36B:
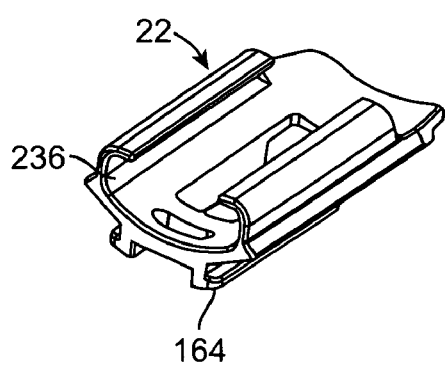
Figure 36C:
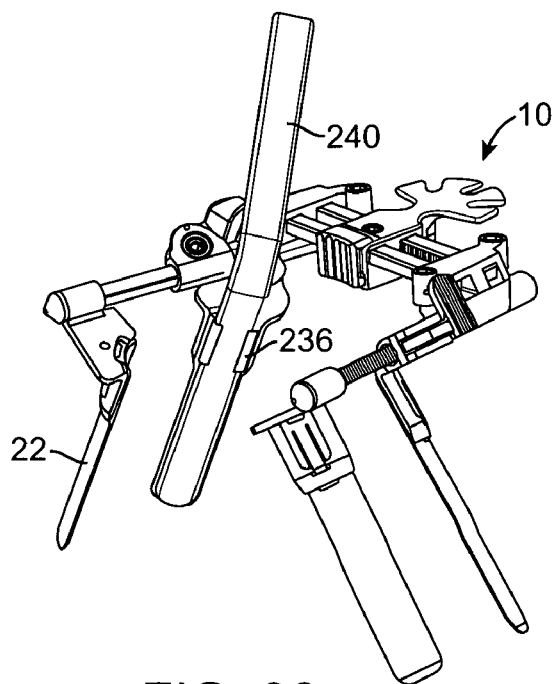
FIG. 36c illustrates an illuminator connected to a retractor blade according to the present invention.

Turning now to FIGS. 36a and 36b, there is shown an other variation of a retractor blade 22 that is configured to be removably attached to the blade supports 84, 116, 130, 158 making the blades 22 interchangeable with other blades of different length(s). The blade 22 includes a hook or tang 164 for connecting with the blade supports. The hook 164 is capable of deflection to capture and release a retractor blade 22. The blade further includes a channel 236 for receiving the blade supports. The blade channels 236 are configured to support an illuminator 240 as shown in FIG. 36c. As seen in the figures, the retractor blades are connected to the blade supports such that the blades extend perpendicularly with respect to the general plane in which right and left assemblies 18, 20 lie. The blades comprise elongate bodies having an inner face and an outer face and a longitudinal axis expending from a proximal end to a distal end. The inner face is generally concave such that the inner faces of four blades placed together form a circular inner perimeter.

The use of the retractor is substantially the same as described above with reference to FIGS. 14-19.

Figure 37:
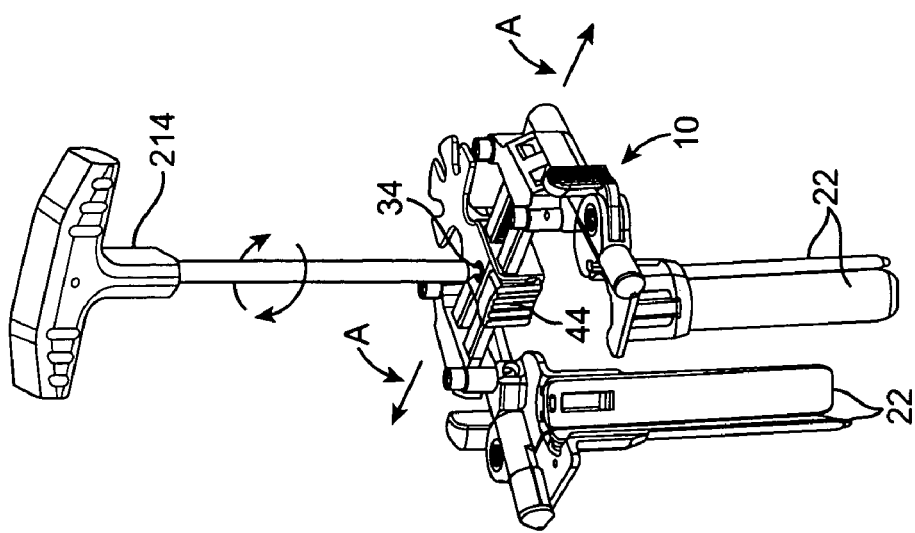

Turning now to FIG. 37, translation of the retractor 10 will now be discussed. With blades 22 attached and the retractor 10 positioned inside the operative site, a T-shaped handle hex driver 214 is inserted into the hex socket of the middle pinion 34 as shown in FIG. 37. When the pinion 34 is rotated, the retractor 10 expands into the configuration shown in FIG. 20 along the direction shown by the arrows A. As the T-shaped hex driver 214 is incrementally turned, the expanded position is locked in position. Reversal of the expansion is accomplished by depressing the release body 44 which unlocks the position for retraction.

Figure 38:
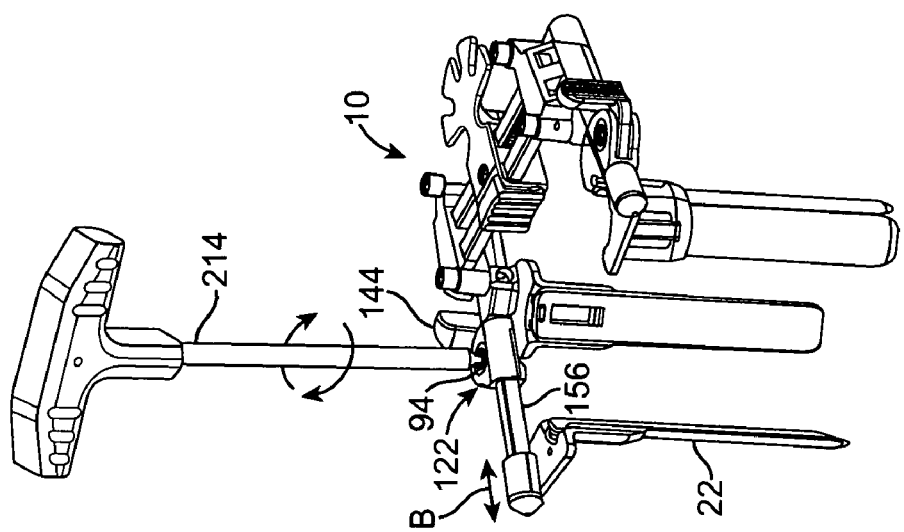

Turning now to FIG. 38, the hex driver 214 is shown inserted into the hex socket of the pinion 94 in the upper left blade support 122 and rotated to drive the ratcheting pin 156 to extend outwardly the lower left blade support 158 as shown by the arrows B. In one variation, reversal of the extension of the lower left blade support 158 is accomplished by rotating the hex driver 214 in the opposite direction. In an alternative variation, the gear lock 144 is employed as a quick release of the extension of the lower left blade support 158 into a relatively retracted position.

Figure 39:
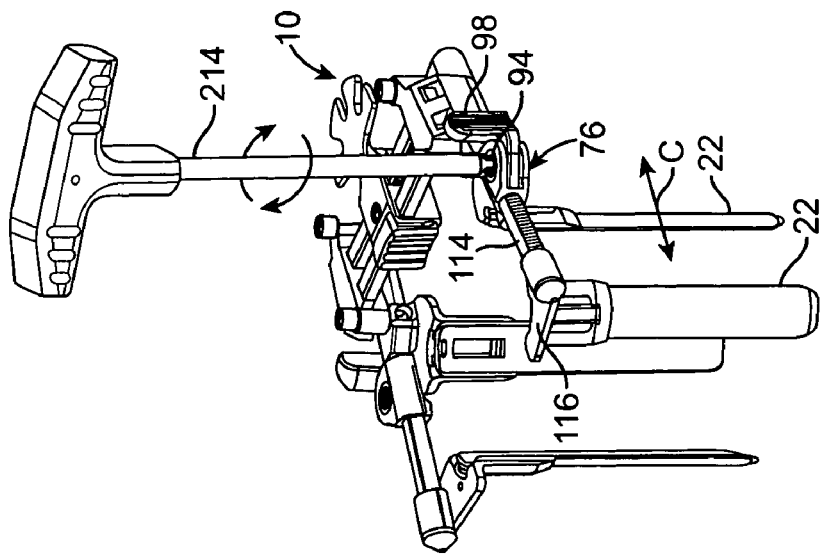
FIGS. 37-43 illustrate translation and angulation of the blades of the retractor according to the present invention.

Turning now to FIG. 39, the hex driver 214 is shown inserted into the hex socket of the pinion 94 in the upper right blade support 76 and rotated to drive the ratcheting pin 114 to extend outwardly the lower right blade support 116 as shown by the arrows C. In one variation, reversal of the extension of the lower right blade support 116 is accomplished by rotating the hex driver 214 in the opposite direction. In an alternative variation, the gear lock 98 is depressed to quickly release the lock and permit quick retraction of the lower right blade support 116.

Figure 40:
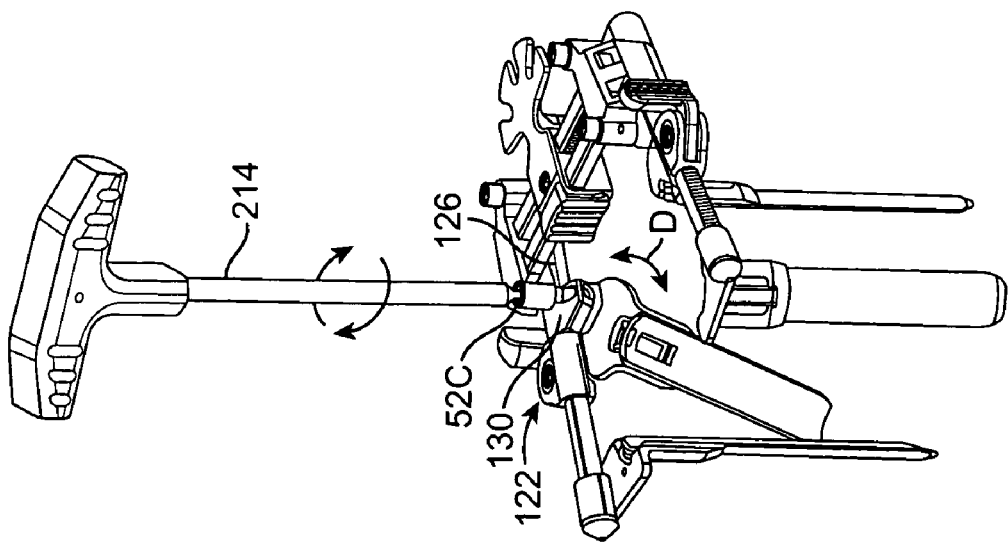

Turning now to FIG. 40, the hex driver 214 is shown inserted into the hex socket of tow angle post 52c and rotated to pivot the upper left blade support 130 with respect to the mounting arm 126 of the upper left blade support assembly 122 as shown by the arrows D. Reversal of the pivoting is accomplished by rotating the hex driver within the tow angle post 52c in the opposite direction to an angle desired by the surgeon.

Figure 41:
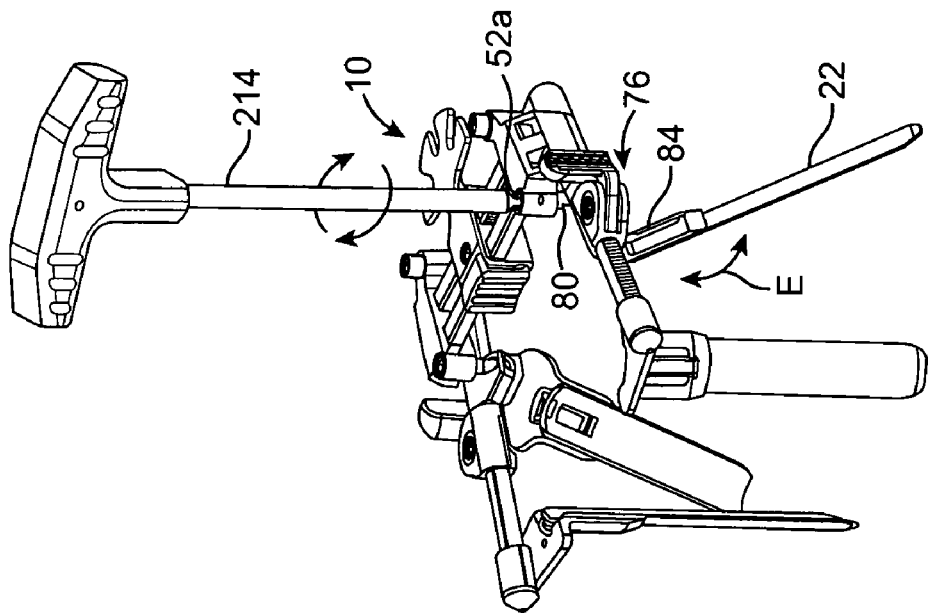

Turning now to FIG. 41, the hex driver 214 is shown inserted into the hex socket of tow angle post 52a and rotated to pivot the upper right blade support 84 with respect to the mounting arm 80 of the upper right blade support assembly 76 as shown by the arrows E. Reversal of the pivoting is accomplished by rotating the hex driver within the tow angle post 52a in the opposite direction to an angle desired by the surgeon.

Figure 42:
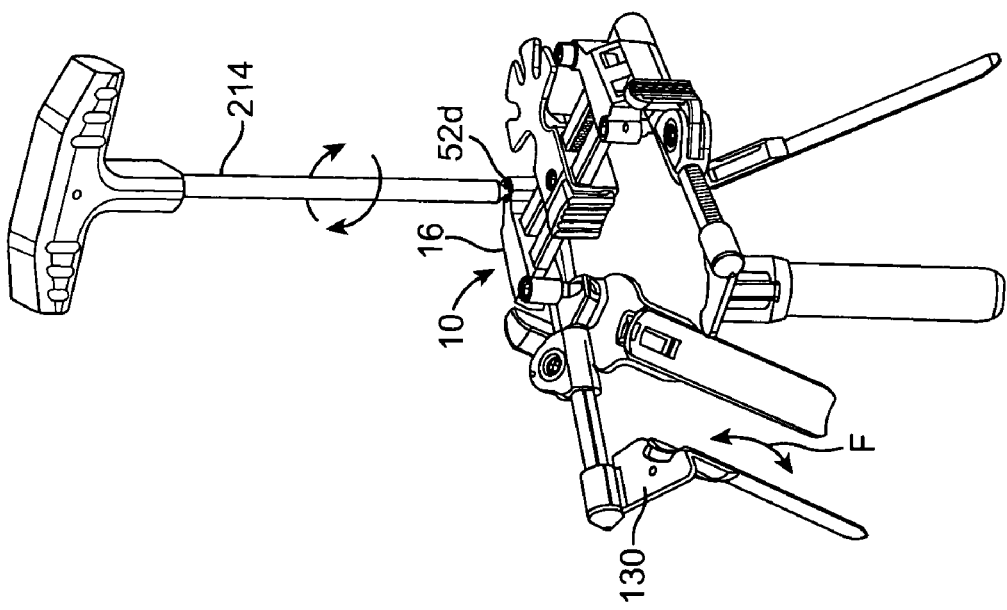

Turning now to FIG. 42, the hex driver 214 is shown inserted into the hex socket of tow angle post 52d and rotated to pivot the lower left blade support 130 with respect to the upper left rack assembly 16 as shown by the arrows F. Reversal of the pivoting is accomplished by rotating the hex driver within the tow angle post 52d in the opposite direction to a desired angle.

Figure 43:
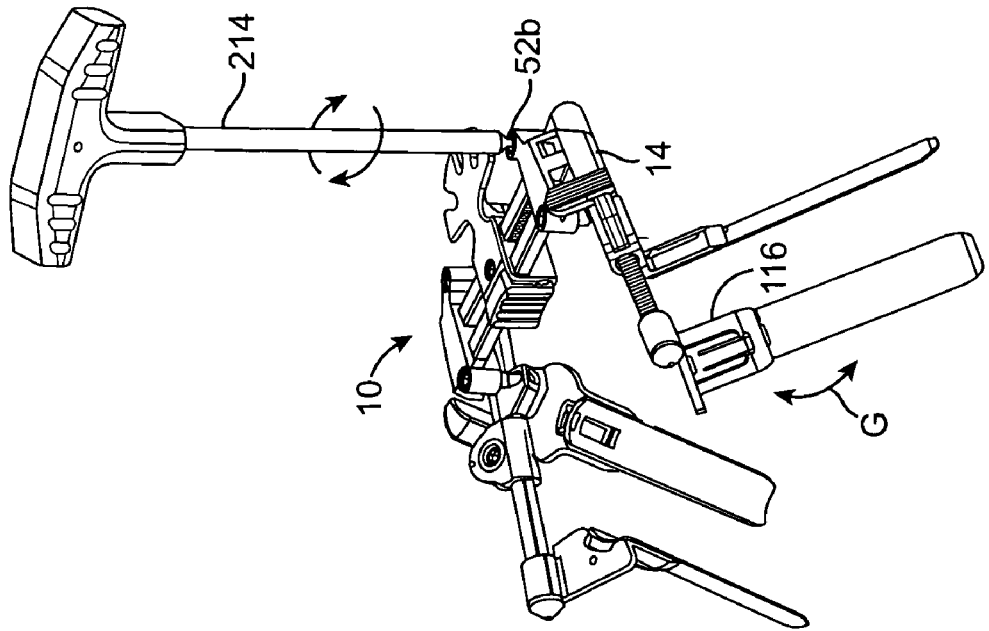

Turning now to FIG. 43, the hex driver 214 is shown inserted into the hex socket of tow angle post 52b and rotated to pivot the lower right blade support 116. with respect to the upper right rack assembly 14 as shown by arrows G. Reversal of the pivoting is accomplished by rotating the hex driver within the tow angle post 52b in the opposite direction to a desired angle.

Turning now to FIGS. 44a, 44b, 44c and 44d, there is shown a medial blade 250 configured for placement between blade supports 84, 116, 130, 158 for additional tissue retraction capability. The medial blade 250 includes a channel 252 for hooking onto one of the ratcheting pins and movable into a desired position along the ratcheting pin as shown in FIG. 44b. Another variation of the medial blade 250 is shown in FIGS. 44c and 44d where the medial blade is shown hooked on one of the straight racks 50, 64. One variation of the medial blade 250 shown in FIG. 44d includes an angled portion 254 configured to angle the blade into the working space for tissue retraction.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A surgical retractor, comprising:
a main body having a main body plane;
a right track assembly connected to the right side of the main body and configured to be movable inwardly and outwardly with respect to the main body;
a left track assembly connected to the left side of the main body and configured to be movable inwardly and outwardly with respect to the main body;
a right blade assembly comprising a right upper blade assembly connected to a right lower blade assembly; the right blade assembly connected to the right track assembly such that right blade assembly moves when the right track assembly moves; the right upper blade assembly including a first blade support and a first removable blade connected to the first blade support such that the first removable blade extends perpendicularly to the main body plane; the right lower blade assembly includes a second blade support and a second removable blade connected to the second blade support such that the second removable blade extends perpendicularly to the main body plane;
a left blade assembly comprising a left upper blade assembly connected to a left lower blade assembly; the left blade assembly connected to the left track assembly such that the left blade assembly moves when the left track assembly moves; the left upper blade assembly including a third blade support and a third removable blade connected to the third blade support such that the third removable blade extends perpendicularly to the main body plane in which the left blade assembly lies; the left lower blade assembly includes a fourth blade support and a fourth removable blade connected to the fourth blade support such that the fourth removable blade extends perpendicularly to the main body plane in which the left blade assembly lies;
wherein the right upper blade assembly includes a right mounting arm having a longitudinal axis and the right lower blade assembly is movable inwardly and outwardly with respect to the right upper blade along the longitudinal axis of the right mounting arm; and
wherein the left upper blade assembly includes a left mounting arm having a longitudinal axis and the left lower blade assembly is movable inwardly and outwardly with respect to the left upper blade along the longitudinal axis of the left mounting arm.

2. The retractor of claim 1 wherein each of the first, second, third and fourth blade supports are independently pivotable such that the attached blades are angled outwardly from their perpendicular orientation and back inwardly to their perpendicular orientation.

3. The retractor of claim 1 wherein the first and second blade supports are simultaneously pivotable such that the attached blades are angled outwardly from their perpendicular orientation and back inwardly to their perpendicular orientation; and the third and fourth blade supports are simultaneously pivotable such that the attached blades are angled outwardly from their perpendicular orientation and back inwardly to their perpendicular orientation.

4. The retractor of claim 3 wherein the pivoting of the first and second blade supports is independent from the pivoting of the third and fourth blade supports.

5. The retractor of claim 1 wherein one of the first, second, third, or fourth removable blades includes a channel for receiving an illuminator.

6. The retractor of claim 1 further including at least one medial blade.

7. The retractor of claim 1 wherein the at least one medial blade is angled.

8. The retractor of claim 1 wherein the right and left mounting arms are angled within the general plane in which the right and left blade assemblies lie.

9. The retractor of claim 1 further including a first pinion configured to incrementally extend the right lower blade assembly with turning of the pinion in one direction.

10. The retractor of claim 9 further including a first gear lock configured to lock the incremental extension of the right lower blade assembly and to release the incremental extension for retracting the right lower blade assembly.

11. The retractor of claim 9 further including a second pinion configured to incrementally extend the left lower blade assembly with turning of the second pinion in one direction.

12. The retractor of claim 11 further including a second gear lock configured to lock the incremental extension of the left lower blade assembly and to release the incremental extension for retracting the left lower blade assembly.

13. The retractor of claim 1 wherein the right track assembly is coupled to the main body using a first track such that the main body moves along the first track, and wherein the left track assembly is coupled to the main body using a second track such that the main body moves along the second track.

14. The retractor of claim 1 wherein the main body comprises a pinion which moves the right track assembly and the left track assembly when activated.

15. The retractor of claim 1 wherein the main body comprises:
a pinion which moves the right track assembly and the left track assembly when activated; and
a pinion lock which allows movement of the right track assembly and the left track assembly in a direction away from the main body using the pinion, wherein the pinion lock inhibits movement of the right track assembly and the left track assembly in a direction toward the main body using the pinion.

16. The retractor of claim 1 wherein the main body comprises:
   a pinion which moves the right track assembly and the left track assembly when activated; and
   a pinion lock which allows movement of the right track assembly and the left track assembly in a direction away from the main body using the pinion, wherein the pinion lock inhibits movement of the right track assembly and the left track assembly in a direction toward the main body using the pinion, and wherein when the pinion lock is activated the pinion lock allows movement of the right track assembly and the left track assembly in a direction toward the main body using the pinion.

* * * * *